(12) United States Patent
Haines et al.

(10) Patent No.: US 7,344,541 B2
(45) Date of Patent: Mar. 18, 2008

(54) METHODS AND APPARATUS FOR FEMORAL AND TIBIAL RESECTION

(75) Inventors: Timothy G. Haines, New Brighton, MN (US); David B. Goldstein, Cream Ridge, NJ (US)

(73) Assignee: Hudson Surgical Design, Inc., Cream Ridge, NJ (US)

( * ) Notice: Subject to any disclaimer, the term of this patent is extended or adjusted under 35 U.S.C. 154(b) by 478 days.

(21) Appl. No.: 10/756,817

(22) Filed: Jan. 13, 2004

(65) Prior Publication Data

US 2005/0055028 A1 Mar. 10, 2005

Related U.S. Application Data

(60) Continuation of application No. 09/799,325, filed on Mar. 5, 2001, now Pat. No. 6,695,848, which is a continuation-in-part of application No. 09/261,528, filed on Mar. 3, 1999, now Pat. No. 6,197,064, which is a continuation of application No. 08/892,286, filed on Jul. 14, 1997, now Pat. No. 5,879,354, which is a division of application No. 08/649,465, filed on May 17, 1996, now Pat. No. 5,755,803, which is a continuation-in-part of application No. 08/603,582, filed on Feb. 20, 1996, now Pat. No. 5,810,827, and a continuation-in-part of application No. 08/479,363, filed on Jun. 7, 1995, now Pat. No. 5,643,272, which is a continuation-in-part of application No. 08/342,143, filed on Nov. 18, 1994, now Pat. No. 5,597,379, which is a continuation-in-part of application No. 08/300,379, filed on Sep. 2, 1994, now Pat. No. 5,514,139.

(51) Int. Cl.
*A61B 17/58* (2006.01)
*A61B 5/00* (2006.01)

(52) U.S. Cl. ............................. 606/88; 606/86; 606/87
(58) Field of Classification Search ................. 606/79, 606/82, 86, 88; 623/20.14–20.36
See application file for complete search history.

(56) References Cited

U.S. PATENT DOCUMENTS 3,739,662 A 6/1973 Windelman et al.

(Continued)

FOREIGN PATENT DOCUMENTS

EP 0189253 7/1986

(Continued)

*Primary Examiner*—Eduardo C. Robert
*Assistant Examiner*—Mary Hoffman
(74) *Attorney, Agent, or Firm*—Patterson, Thuente, Skaar & Christensen, P.A.

(57) ABSTRACT

Methods and apparatus for knee arthroplasty utilize components including an alignment device, a single medially or laterally located guidance device, and a cutting device for use in preparing the bones of a knee joint to receive knee arthroplasty implants. The alignment device is used to locate and orient the guidance device adjacent the medial or lateral side of a long bone of a knee joint. The cutting device is engaged with the guidance device and plunged across the end of the long bone to create a resected surface with respect to which a knee arthroplasty implant will be fixed. In one embodiment, the cutting tool guidance device extends less than about half way across the end of a long bone of a knee joint.

54 Claims, 40 Drawing Sheets

U.S. PATENT DOCUMENTS

| | | | |
|---|---|---|---|
| 3,774,244 A | 11/1973 | Walker | |
| 3,798,679 A | 3/1974 | Ewald | |
| 3,816,855 A | 6/1974 | Saleh | |
| 4,178,641 A | 12/1979 | Grundei et al. | |
| 4,353,135 A | 10/1982 | Forte et al. | |
| 4,358,859 A | 11/1982 | Schurman et al. | |
| 4,421,112 A | 12/1983 | Mains et al. | |
| 4,457,307 A | 7/1984 | Stillwell | |
| 4,474,177 A | 10/1984 | Whiteside | |
| 4,487,203 A | 12/1984 | Androphy | |
| 4,501,266 A | 2/1985 | McDaniel | |
| 4,502,483 A | 3/1985 | Lacey | |
| 4,524,766 A | 6/1985 | Petersen | |
| 4,566,448 A | 1/1986 | Rohr, Jr. | |
| 4,567,886 A | 2/1986 | Petersen | |
| 4,568,348 A | 2/1986 | Johnson et al. | |
| 4,586,496 A | 5/1986 | Keller | |
| 4,586,933 A | 5/1986 | Shoji et al. | |
| 4,653,488 A | 3/1987 | Kenna | |
| 4,662,889 A | 5/1987 | Zichner et al. | |
| 4,721,104 A | 1/1988 | Kaufman et al. | |
| 4,722,330 A | 2/1988 | Russell et al. | |
| 4,736,737 A * | 4/1988 | Fargie et al. | 606/88 |
| 4,738,256 A | 4/1988 | Freeman et al. | |
| 4,770,663 A | 9/1988 | Hanslik et al. | |
| 4,787,383 A | 11/1988 | Kenna | |
| 4,822,365 A | 4/1989 | Walker et al. | |
| 4,841,975 A | 6/1989 | Woolson | |
| 4,892,093 A | 1/1990 | Zarnowski et al. | |
| 4,896,663 A | 1/1990 | Vandewalls | |
| 4,938,762 A | 7/1990 | Wehrli | |
| 4,952,213 A | 8/1990 | Bowman et al. | |
| 5,002,545 A | 3/1991 | Whiteside et al. | |
| 5,021,056 A * | 6/1991 | Hofmann et al. | 606/86 |
| 5,047,032 A | 9/1991 | Jellicoe | |
| 5,049,149 A | 9/1991 | Schmidt | |
| 5,053,037 A | 10/1991 | Lackey | |
| 5,098,436 A | 3/1992 | Ferrante et al. | |
| 5,100,409 A | 3/1992 | Coates et al. | |
| 5,129,909 A | 7/1992 | Sutherland | |
| 5,147,365 A | 9/1992 | Whitlock et al. | |
| 5,226,916 A | 7/1993 | Goodfellow et al. | |
| 5,228,459 A | 7/1993 | Caspari et al. | |
| 5,234,432 A | 8/1993 | Brown | |
| 5,234,433 A * | 8/1993 | Bert et al. | 606/88 |
| 5,250,050 A | 10/1993 | Poggie et al. | |
| 5,263,498 A | 11/1993 | Caspari et al. | |
| 5,269,786 A | 12/1993 | Morgan | |
| 5,284,482 A | 2/1994 | Mikhail | |
| 5,304,181 A | 4/1994 | Caspari et al. | |
| 5,306,276 A | 4/1994 | Johnson et al. | |
| 5,314,482 A | 5/1994 | Goodfellow et al. | |
| 5,342,368 A | 8/1994 | Petersen | |
| 5,364,401 A | 11/1994 | Ferrante et al. | |
| 5,454,816 A | 10/1995 | Ashby | |
| 5,474,559 A | 12/1995 | Bertin et al. | |
| 5,514,139 A | 5/1996 | Goldstein et al. | |
| 5,514,143 A | 5/1996 | Bonutti et al. | |
| 5,542,947 A | 8/1996 | Treacy | |
| 5,578,039 A | 11/1996 | Vendrely et al. | |
| 5,593,411 A | 1/1997 | Stalcup et al. | |
| 5,597,379 A | 1/1997 | Haines et al. | |
| 5,601,563 A | 2/1997 | Burke et al. | |
| 5,611,802 A | 3/1997 | Samuelson et al. | |
| 5,628,749 A | 5/1997 | Vendrely et al. | |
| 5,643,272 A | 7/1997 | Haines et al. | |
| 5,653,714 A | 8/1997 | Dietz et al. | |
| 5,667,511 A | 9/1997 | Vendrely et al. | |
| 5,682,886 A | 11/1997 | Delp et al. | |
| 5,690,635 A | 11/1997 | Matsen, III et al. | |
| 5,690,637 A | 11/1997 | Wen et al. | |
| 5,755,803 A | 5/1998 | Haines et al. | |
| 5,810,827 A | 9/1998 | Haines et al. | |
| 5,879,354 A | 3/1999 | Haines et al. | |
| 5,980,526 A | 11/1999 | Johnson et al. | |
| 6,056,754 A | 5/2000 | Haines et al. | |
| 6,197,064 B1 | 3/2001 | Haines et al. | |
| 6,695,848 B2 | 2/2004 | Haines | |
| 2005/0149038 A1 | 7/2005 | Haines et al. | |
| 2005/0149039 A1 | 7/2005 | Haines et al. | |
| 2005/0149040 A1 | 7/2005 | Haines et al. | |

FOREIGN PATENT DOCUMENTS

| | | |
|---|---|---|
| EP | 0466659 A2 | 1/1992 |
| EP | 0538153 A1 | 4/1993 |
| EP | 0682916 A2 | 11/1995 |
| FR | 2664157 A1 | 1/1992 |
| SU | 577020 | 10/1977 |
| WO | WO/9601588 | 1/1996 |
| WO | WO 09607361 A1 | 3/1996 |
| WO | WO 9729703 A1 | 8/1997 |
| WO | WO 9729704 A1 | 8/1997 |

* cited by examiner

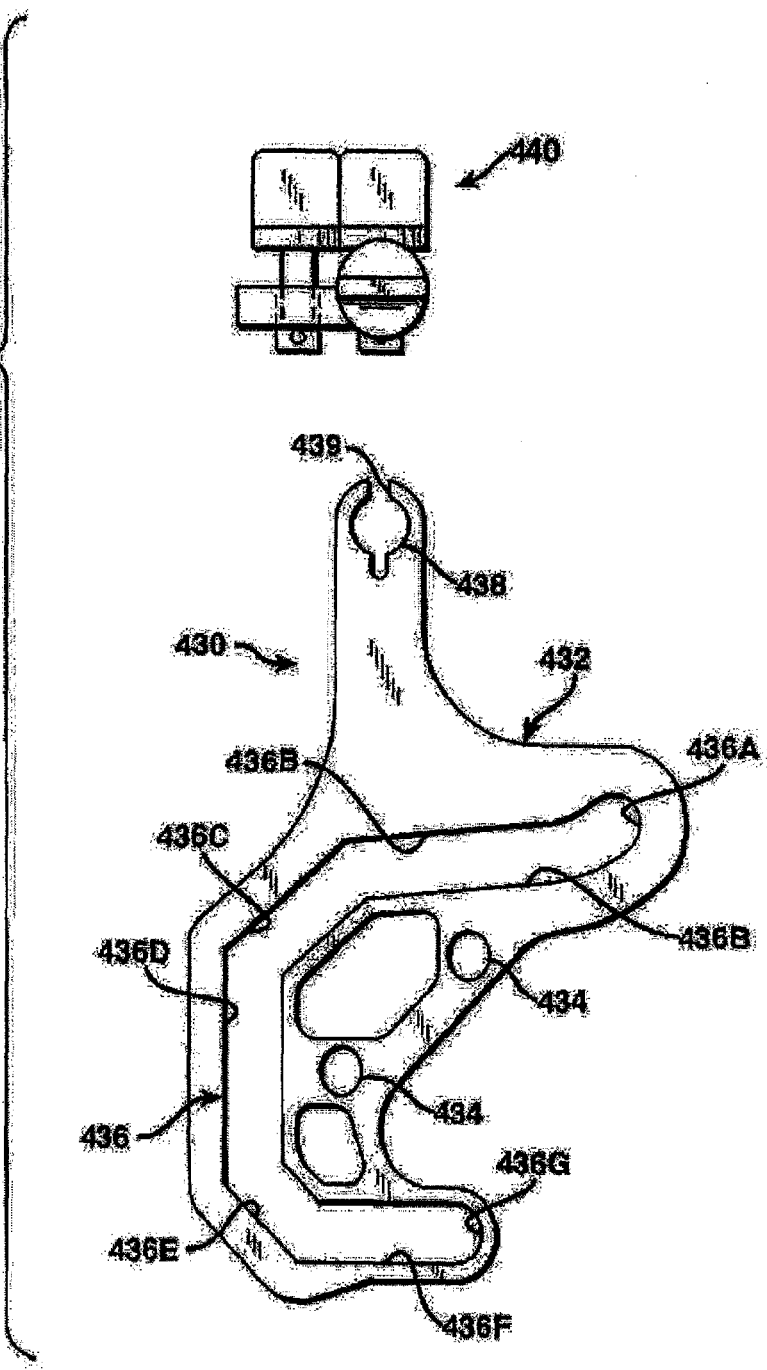

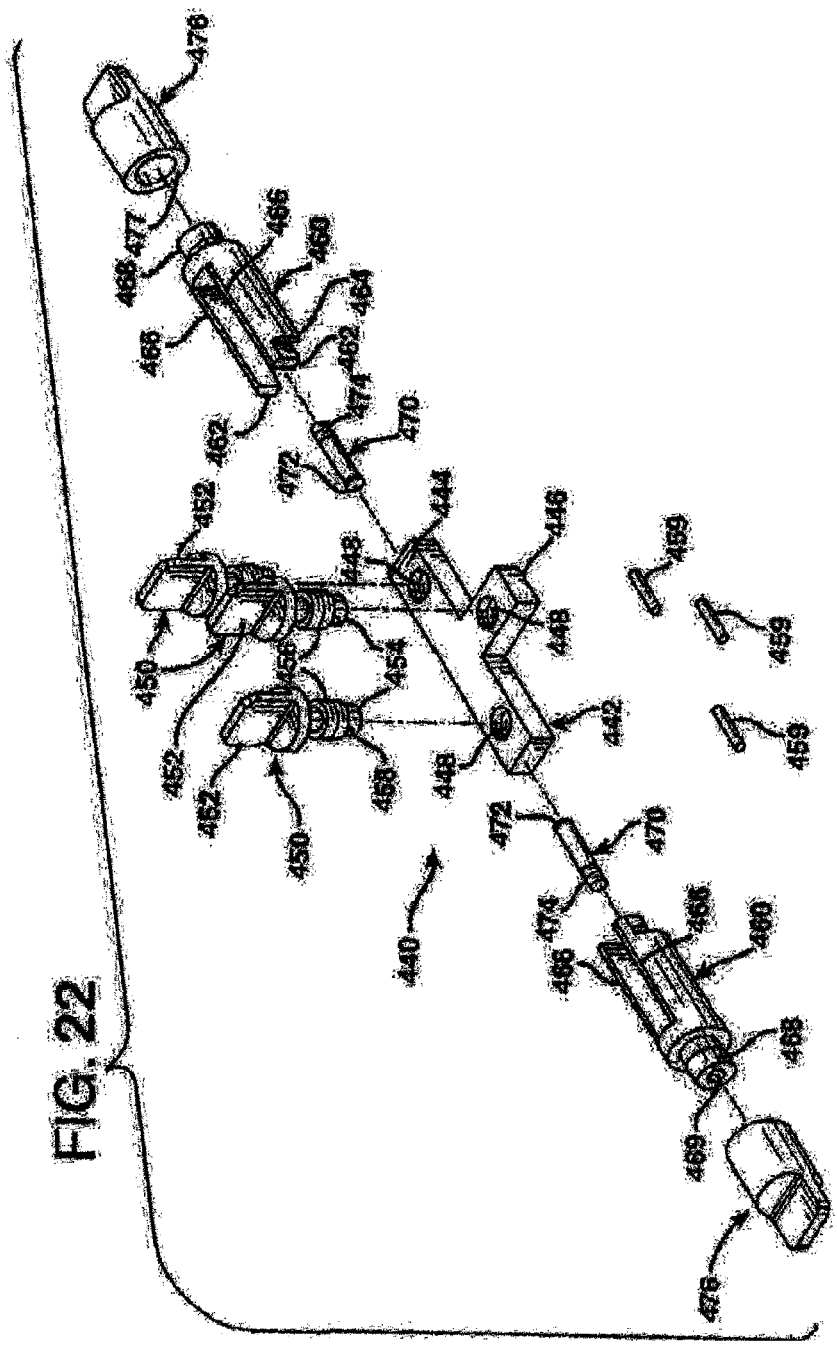

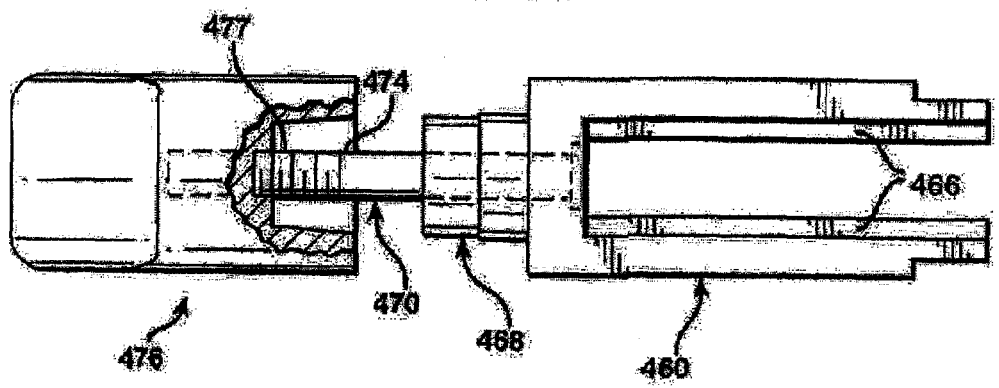
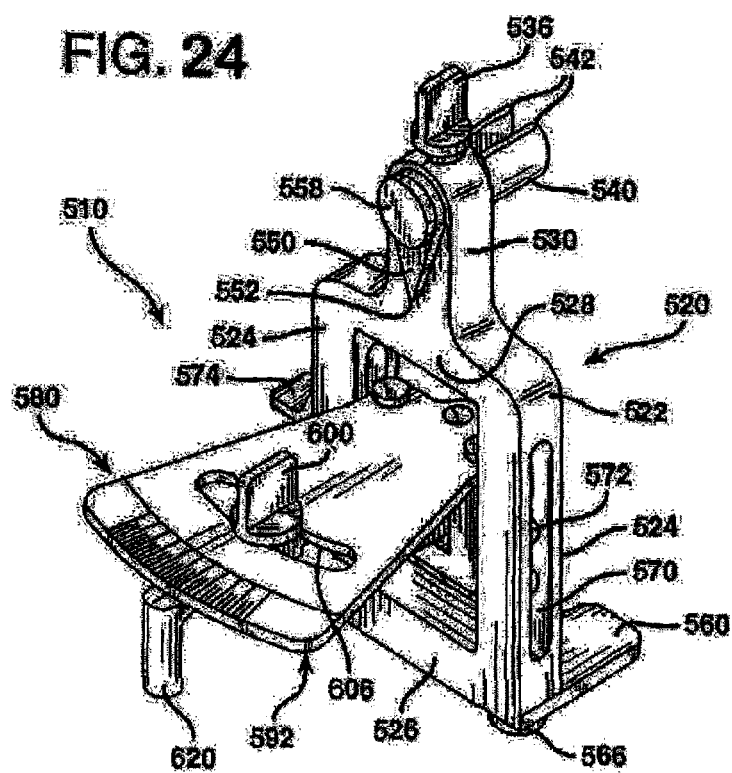

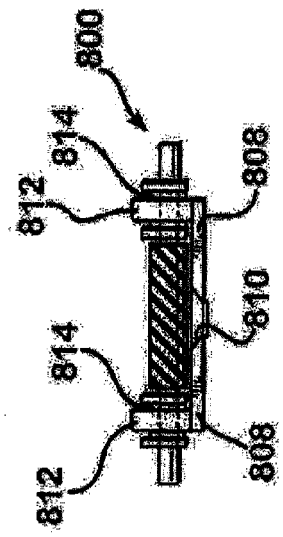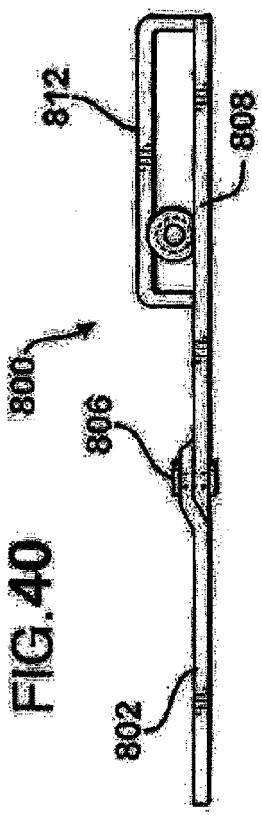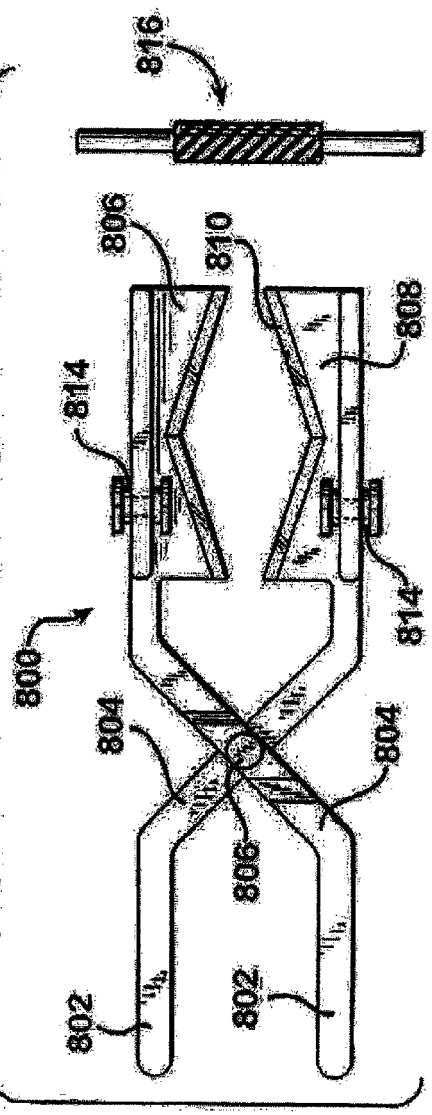

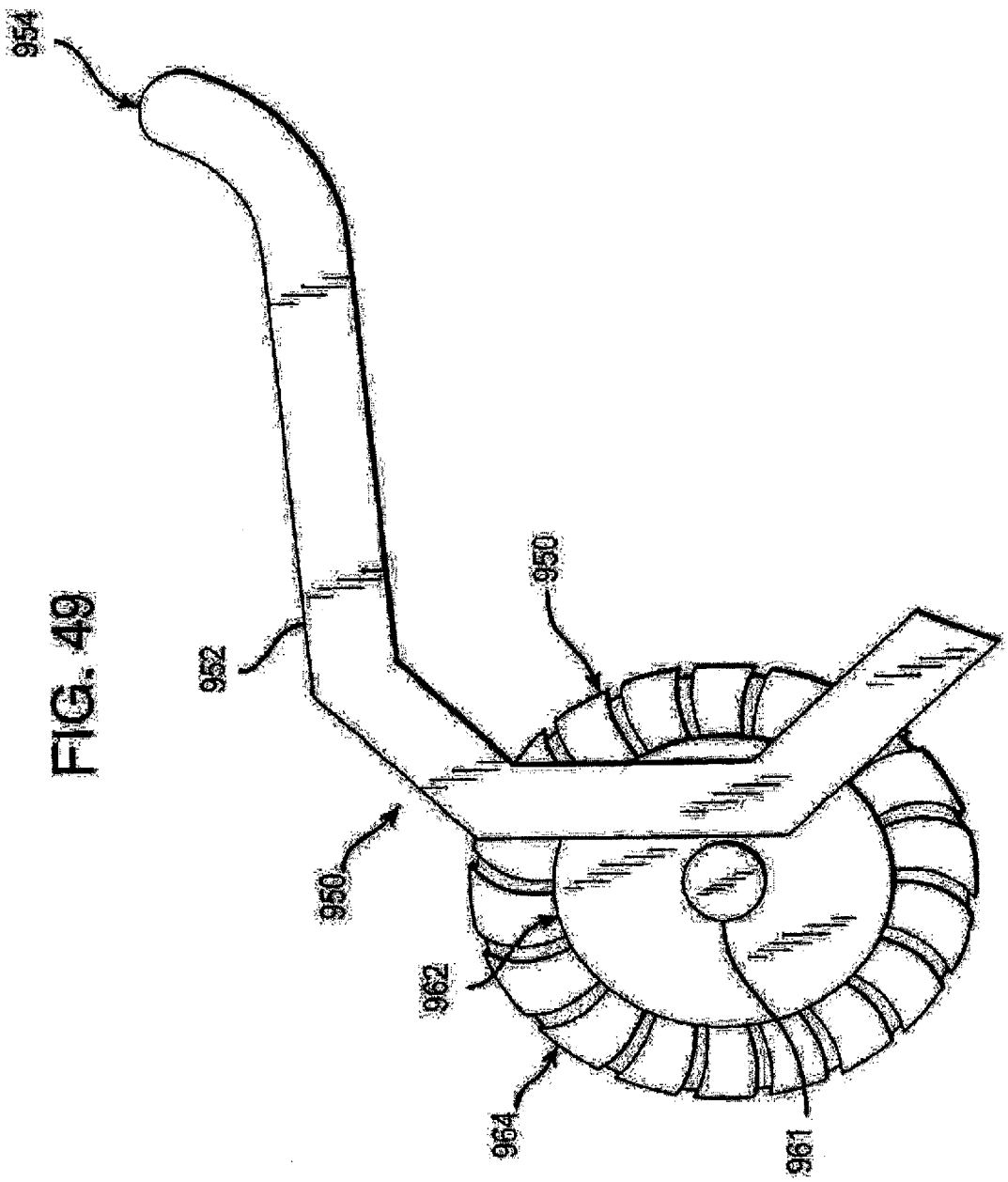

METHODS AND APPARATUS FOR FEMORAL AND TIBIAL RESECTION

RELATED APPLICATIONS

This application is a continuation of U.S. application Ser. No. 09/799,325 filed Mar. 5, 2001 now U.S. Pat. No. 6,695,848, which is a continuation-in-part of U.S. application Ser. No. 09/261,528, filed Mar. 3, 1999, now U.S. Pat. No. 6,197,064, which was a continuation of U.S. application Ser. No. 08/892,286 filed Jul. 14, 1997, now U.S. Pat. No. 5,879,354, which was a divisional of U.S. application Ser. No. 08/649,465, filed May 17, 1996, now U.S. Pat. No. 5,755,803, which was a continuation-in-part application of U.S. application Ser. No. 08/603,582, filed Feb. 20, 1996, now U.S. Pat. No. 5,810,827, which was a continuation-in-part application of U.S. application Ser. No. 08/300,379, filed Sep. 2, 1994, now U.S. Pat. No. 5,514,139, dated May 7, 1996, and which was also a continuation-in-part application of U.S. application Ser. No. 08/479,363, now U.S. Pat. No. 5,643,272, which is a continuation-in-part of U.S. application Ser. No. 08/342,143, filed Nov. 18, 1994, now U.S. Pat. No. 5,597,379, which is a continuation-in-part application of U.S. application Ser. No. 08/300,379, filed Sep. 2, 1994, now U.S. Pat. No. 5,514,139, dated May 7, 1996. U.S. Ser. No. 479,363. The entire disclosures of these related applications are expressly incorporated herein by reference.

BACKGROUND OF THE INVENTION

1. Field of the Invention

This invention generally relates to methods and apparatus for femoral and tibial resection to allow for the interconnection or attachment of various prosthetic devices.

2. Related Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating sawblade based resection systems has been the standard in total knee replacement for over 30 years. Due to their use of this sub-optimal cutting tool, the instrumentation systems all possess certain limitations and liabilities.

Perhaps the most critical factor in the clinical success of TKA is the accuracy of the implant's placement. This can be described by the degrees of freedom associated with each implant; for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of ⅛ or 3/16 inch diameter pin or drill placement in the anterior or distal faces of the femur for placement of cutting guides. In the case of posterior referencing systems, the distal resection cutting guide is positioned by drilling two long drill bits into the anterior cortex. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking," inherent in the use of multiple alignment guides and cutting guides. Another error inherent in these systems further adding to mal-alignment is deflection of the oscillating sawblade during the cutting process. The use of an oscillating sawblade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA for more than 30 years, orthopedic salespeople still report incidences where poor cuts result in significant gaps in the fit between the implant and the bone.

It is an often repeated rule of thumb for orthopedic surgeons that a "Well placed, but poorly designed implant will perform well clinically, while a poorly placed, well designed implant will perform poorly clinically." One of the primary goals of the invention described herein is to eliminate errors of this kind to create more reproducible, consistently excellent clinical results in a manner that requires minimal manual skill on the part of the surgeon.

None of the previous efforts of others disclose all of the benefits and advantages of the present invention, nor do the previous efforts of others teach or suggest all the elements of the present invention.

OBJECTS AND SUMMARY OF THE INVENTION

Many of the specific applications of the method and apparatus of the present invention described herein apply to total knee replacement, a surgical procedure wherein planar surfaces and/or curvilinear surfaces must be created in or on bone to allow for proper attachment or implantation of prosthetic devices. However, it should be noted that it is within the scope of the present invention to apply the methods and apparatus herein described to the removal of any kind of material from bones in any other application where it is necessary, desirable or useful to remove material from bones.

The apparatus of the present invention comprises a number of components including a positioning apparatus, a pattern apparatus and a cutting apparatus.

The pattern apparatus is oriented and located by the use of the positioning apparatus which references the geometry of a bone to be resected and/or other anatomic landmarks. When used to resect a distal femur, the positioning apparatus also references the long axis of the femur. Once the positioning apparatus has been properly located, aligned, and initially fixed in place, the pattern apparatus may be attached thereto, and then adjusted according to the preferences of the surgeon utilizing the apparatus, and then the pattern apparatus can be rigidly fixed to a bone to be resected. This ensures the pattern apparatus is properly located and oriented prior to the use of the cutting apparatus to remove material from the bone.

More specifically, when the method and apparatus of the present invention are used in connection with resecting a distal femur, the positioning apparatus is located and aligned utilizing the intramedullary canal of the femur, (thereby approximating the long axis of the femur), the distal surfaces of the femoral condyles, the anterior surface of the distal femur, and the posterior surfaces of the femoral condyles, which are referenced to indicate the appropriate location and orientation of the pattern apparatus. Fixation means may be used to fix the positioning apparatus, as well as the pattern apparatus to the distal femur. Means may be present in the positioning apparatus and/or pattern device for allowing the following additional adjustments in the location and orientation of the pattern device:

1. internal and external rotational adjustment;
2. varus and valgus angular adjustment;
3. anterior and posterior location adjustments;
4. proximal and distal location adjustment; and
5. flexion and extension angular adjustment.

Cannulated screws, fixation nails or other fixation means may then be used to firmly fix the pattern apparatus to the distal femur. The positioning apparatus may then be disconnected from the pattern apparatus and removed from the distal femur. Thus, the location and orientation of the pattern apparatus is established.

The pattern device possesses slot-like features, or a cutting path, having geometry that matches or relates to the desired geometry of the cut. When used in connection with resecting a knee, the cutting path resembles the interior profile of the distal femoral prosthesis. The cutting path guides the cutting apparatus to precisely and accurately remove material from the distal femur. Thus, the distal femur is thereby properly prepared to accept a properly aligned and located distal prosthesis.

In preparing a patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

The apparatus of the present invention comprises a number of components including an ankle clamp, an alignment rod, a fixation head, cutting guide clamps having an integral attachment mechanism, and a milling bit.

The method of present invention includes the steps of attaching the ankle clamp about the ankle, interconnecting the distal end of the alignment rod with the ankle clamp, interconnecting the fixation head with the proximal end of the alignment rod, partially attaching the fixation head to the proximal tibia, aligning the alignment rod, completely attaching the fixation head to the proximal tibia, interconnecting the cutting guide clamps with the alignment rod, positioning the cutting guide clamps about the proximal tibia, securing the cutting guide clamps to the tibia at a proper location, removing the fixation head, and cutting the proximal tibia with the milling bit.

The implant of the present invention has an outer bearing surface and an inner attachment surface. The outer bearing surface functions as a joint contact surface for the reconstructed bone. The inner attachment surface contacts a bone and is attached thereto. The inner attachment surface of the implant is curvilinear from an anterior to a posterior area of the femur, as is conventionally known, and is also curvilinear from a medial to a lateral area of the femur to approximate the shape of natural femur. The resection of the femur for accommodating the implant can be properly performed by a milling device employing one or more curvilinear milling bits.

There are numerous advantages associated with the curvilinear implant of the present invention. First, it will allow for a very thin implant cross-section and therefore necessitate the removal of the least amount of viable osseous tissue. Accordingly, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs.

This curvilinear implant of the present invention could also result in a less expensive femoral implant because of the reduced amount of material needed for the implant, as well as an improved, more natural, and even stronger knee replacement. The cross-section of the implant could be varied to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces.

The resected surfaces of a femur or other bone to accept the implant of the present invention could be prepared by the apparatus and method for resection shown and described in the prior related applications set forth herein, the entire disclosures of which are expressly incorporated herein by reference.

The apparatus of the present invention comprises a number of components including a positioning and drill guide, a cutting guide and a cutting apparatus. The drill guide is used to create holes in the medial and lateral sides of the femur that correspond to the fixation features of the cutting guide. The cutting guide is oriented and located by inserting fixation nubs connected to the cutting guide into the medial and lateral holes in the femur. The cutting guide can then be further affixed to the femur. The cutting apparatus can then be used with the cutting guide to resect the femur. A conventional cutting block used with a conventional oscillating saw can also be positioned and interconnected with a femur in a similar manner using the drill guide of the present invention to create medial and lateral holes. A cutting guide can then be attached to the holes. A conventional cutting block can be interconnected with the cutting guide for attachment of the block to the femur. This invention can also be used in connection with a cortical milling system, i.e., a cutting system for providing a curvilinear cutting path and curvilinear cutting profile. Likewise, a tibial cutting guide can similarly be positioned on a tibia with a drill guide.

It is a primary object of the present invention to provide an apparatus for properly resecting the distal human femur.

It is also an object of this invention to provide an apparatus for properly orienting a resection of the distal human femur.

It is an additional object of the resection apparatus of the present invention to properly locate the resection apparatus with respect to the distal human femur.

It is even another object of the resection apparatus of the present invention to properly orient the resection apparatus with respect to the distal human femur.

It is another object of the resection apparatus of the present invention to provide a guide device for establishing the location and orientation of the resection apparatus with respect to the distal human femur.

It is still a further object of the resection apparatus of the present invention to lessen the chances of fatty embolisms.

It is even a further object of this invention is to provide a resection apparatus capable of forming some or all of the resected surfaces of the distal human femur.

It is another object of the resection apparatus of the present invention to provide an apparatus which is simple in design and precise and accurate in operation.

It is also an intention of the resection apparatus of the present invention to provide a guide device for determining the location of the long axis of the femur while lessening the chances of fatty embolism.

It is also an object of the resection apparatus of the present invention to provide a device to physically remove material from the distal femur in a pattern dictated by the pattern device.

It is even another object of the resection apparatus of the present invention to provide a circular cutting blade for removing bone from the distal human femur to resection the distal human femur.

It is also an object of the present invention to provide a method for easily and accurately resecting a distal human femur.

These objects and others are met by the resection method and apparatus of the present invention.

It is a primary object of the present invention to provide methods and apparatus for femoral and tibial resection.

It is another object of the present invention to provide a method and apparatus for properly, accurately and quickly resecting a bone.

It is also an object of this invention to provide a method and apparatus for properly orienting and locating a resection of a bone.

It is a further object of the present invention to provide a method and apparatus to properly locate and orient the resection apparatus with respect to a bone.

It is another object of the present invention to provide methods and apparatus for femoral and tibial resection which are simple in design and precise and accurate in operation.

It is an additional object of the present invention to provide a method and apparatus to physically remove material from a bone in a pattern dictated by a pattern device and/or the geometry of a cutting device.

It is a further object of the present invention to provide methods and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is a further object of the present invention to provide methods and apparatus for femoral and tibial resection wherein the apparatus can be located on a bone to be cut in a quick, safe and accurate manner.

It is a primary object of the present invention to provide a method and apparatus for properly resecting the proximal human tibia in connection with knee replacement surgery.

It is also an object of the present invention to provide a method and apparatus for resecting the proximal human tibia which minimizes the skill necessary to complete the procedure.

It is another object of the present invention to provide a method and apparatus for resecting the proximal human tibia which properly orients the resection of the proximal tibia.

It is even another object of the present invention to provide a method and apparatus for resecting the proximal human tibia which is easy to use.

It is yet another object of the present invention to provide a method and apparatus for resecting the proximal human tibia which orients the resection in accordance with what is desired in the art.

It is still yet another object of the present invention to provide a method and apparatus for resecting the proximal human tibia which minimizes the amount of bone cut.

It is a further object of the present invention to provide a method and apparatus for resecting the proximal human tibia which allows one to visually inspect the location of the cut prior to making the cut.

It is even a further object of the present invention to provide a method and apparatus for resecting the proximal human tibia which is simple in design and precise and accurate in operation.

It is yet a further object of the present invention to provide a method and apparatus for resecting the proximal human tibia which physically removes material from the proximal tibia along a surface dictated by a guide device.

It is still a further object of the present invention to provide a method and apparatus for resecting the proximal human tibia which employs a milling bit for removing material from the proximal tibia.

It is also an object of the present invention to provide a method and apparatus for resecting the proximal human tibia which includes a component which is operated, and looks and functions, like pliers or clamps.

It is even another object of the present invention to provide an alternate embodiment of the method and apparatus for resecting the proximal human tibia which includes a component that resembles a U-shaped device for placing about the tibia.

It is even a further object of the present invention to provide an alternate embodiment of the method and apparatus for resecting the proximal human tibia which includes a component that resembles an adjustable, square, U-shaped device for placing about the tibia.

These objects and others are met and accomplished by the method and apparatus of the present invention for resecting the proximal tibia.

It is a primary object of the present invention to provide a method and apparatus for removing material from bones.

It is another object of the present invention to provide a method and apparatus for properly resecting bone.

It is also an object of this invention to provide a method and apparatus for properly orienting a resection of a bone.

It is a further object of the present invention to provide a method and apparatus to properly orient the resection apparatus with respect to a bone.

It is an additional object of the present invention to provide a method and apparatus for properly locating a bone resection.

It is a further object of the present invention to provide a method and apparatus to properly locate the resection apparatus with respect to a bone.

It is even another object of the resection apparatus of the present invention to provide a guide device and method of use thereof for establishing the location and orientation of the resection apparatus with respect to a bone.

It is an additional object of the present invention to provide a method and apparatus for making a curvilinear bone resection.

It is still a further object of the resection apparatus of the present invention to lessen the chances of fatty embolisms.

It is even further object of this invention to provide a method and apparatus capable of forming or re-forming some or all of the surfaces or resected surfaces of a bone.

It is another object of the present invention to provide a method and apparatus which is simple in design and precise and accurate in operation.

It is also an intention of the present invention to provide a method and apparatus for determining the location of the long axis of a bone while lessening the chances of fatty embolisms.

It is also an object of the present invention to provide a method and apparatus to physically remove material from a bone in a pattern.

It is an additional object of the present invention to provide a method and apparatus to physically remove material from a bone in a pattern dictated by a pattern device and/or the geometry of a cutting device.

It is even another object of the resection apparatus of the present invention to provide a cylindrical or semi-cylindrical cutting device and method of use thereof for removing material from a bone.

It is also an object of the present invention to provide a method and apparatus for easily and accurately resecting a bone.

It is also an object of the present invention to provide a method and apparatus for resecting a bone which minimizes the manual skill necessary to complete the procedure.

It is even another object of the present invention to provide a method and apparatus for resecting a bone which is easy to use.

It is still yet another object of the present invention to provide a method and apparatus for resecting a bone which minimizes the amount of bone removed.

It is a further object of the present invention to provide a method and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is even another object of the present invention to provide a method and apparatus for removing material from a bone such that both the cutting path and cutting profile are predominantly curvilinear.

It is a primary object of the present invention to provide an apparatus to properly replace damaged bony tissues.

It is also an object of this invention to provide an apparatus to properly replace damaged bony tissues in joint replacement surgery.

It is also an object of the present invention to provide an implant for the attachment to a distal femur in the context of knee replacement surgery.

It is an additional object of the present invention to provide a method and apparatus for making a curvilinear implant.

It is another object of the present invention to provide an implant having a reduced thickness to reduce the amount of material required to make the implant.

It is even another object of the present invention to provide an implant having curvilinear fixation surfaces for increasing the strength of the implant.

It is another object of the present invention to provide an implant having a fixation surface that is anterior-posterior curvilinear and mediolateral curvilinear.

It is another object of the present invention to provide an implant that has a fixation surface that is shaped to resemble a natural distal femur.

It is also an object of the present invention to provide an implant apparatus for allowing proper patellofemoral articulation.

It is a further object of the present invention to provide for minimal stress shielding of living bone through reduction of flexural rigidity.

It is an additional object of the present invention to provide an implant apparatus having internal fixation surfaces which allow for minimal bony material removal.

It is another object of the present invention to provide an implant apparatus with internal fixation surfaces that minimize stress risers.

It is another object of the present invention to provide an implant apparatus having internal fixation surfaces for precise fixation to curvilinear body resections.

It is another object of the present invention to provide an implant apparatus having internal fixation surfaces for precise apposition to curvilinear body resections.

It is another object of the present invention to provide an implant apparatus having internal fixation surfaces for curvilinear interior fixation geometries closely resembling the geometry of the external or articular geometry of the implant apparatus.

It is also an object of this invention to provide a method and apparatus for properly locating and orienting a prosthetic implant with respect to a bone.

It is another object of the present invention to provide an implant which is simple in design and precise and accurate in operation.

It is also an object of the present invention to provide an implant which minimizes the manual skill necessary to complete the procedure.

It is still yet another object of the present invention to provide an implant which minimizes the amount of bone removed.

It is even another object of the present invention to provide a method and apparatus for removing material from a bone such that both the cutting path and cutting profile are predominantly curvilinear.

BRIEF DESCRIPTION OF THE DRAWINGS

Other important objects and features of the invention will be apparent from the following detailed description of the invention taken in connection with the accompanying drawings in which:

FIG. 21 is a partially exploded side plan view of the positioning apparatus shown in FIG. 19.

FIG. 22 is an exploded perspective view of the cross-bar of the pattern apparatus shown in FIG. 19.

FIG. 23 is a partially cut away side plan view of the pattern plate/cross-bar attachment linkage for interconnecting the pattern plate to the cross-bar as shown in FIG. 19.

FIG. 24 is a perspective view of the positioning apparatus of the present invention.

FIG. 40 is a side plan view of another embodiment of the pattern apparatus and positioning apparatus of the present invention for resecting a patella.

FIG. 41 is a top plan view of the patella resection apparatus shown in FIG. 40.

FIG. 42 is a front plan view of the patella resection apparatus shown in FIG. 40.

FIG. 49 is a side plan view of the curvilinear milling bit and resection guide shown in FIG. 35.

DETAILED DESCRIPTION OF THE PREFERRED EMBODIMENTS

As shown generally in FIGS. 1-6, the resecting apparatus of the present invention comprises a number of components, namely positioning apparatus generally indicated at 10 comprising positioning body generally indicated at 12, angular adjustment block generally indicated at 32, rotational alignment device generally indicated at 50, pattern device generally indicated at 59 and cutting means generally indicated at 90.

Figure 1:
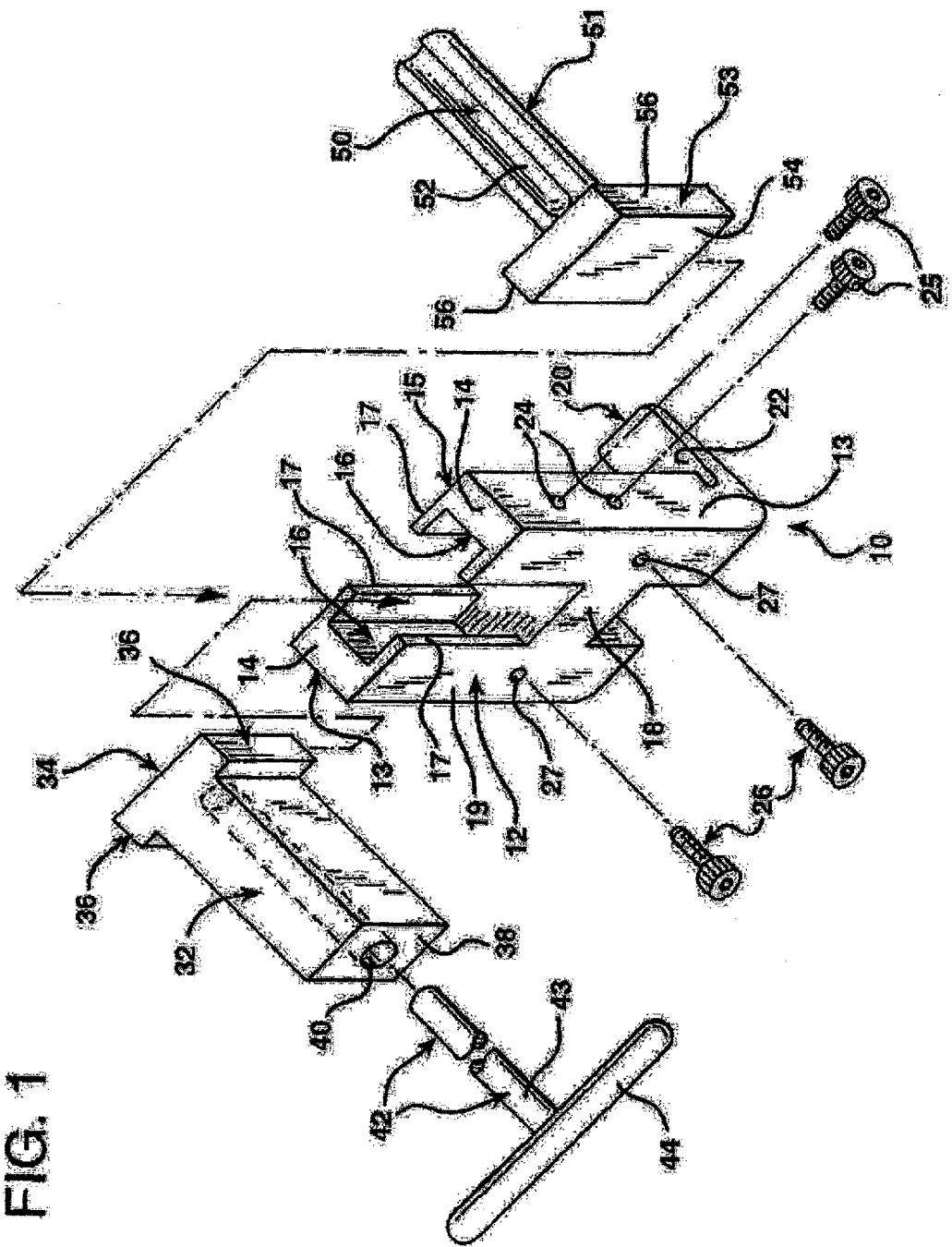
FIG. 1. is an exploded view of the resection apparatus of the present invention showing the positioning apparatus body, the angular adjustment component and the rotational alignment component.

As shown in detail in FIG. 1, the positioning apparatus, generally indicated at 10, includes a positioning body generally indicated at 12 having sides 13, top surface 14, front surface 15, back surface 19 and cross member 18. Extending from a lower end of the positioning body 12 is positioning tongue 20 having an upper surface 22. Extending into the positioning body 12 from top surface 14 to the cross member 18 and through the front and back surfaces 15 and 19, is a gap generally defined by slots 16 and partial slot walls 17. Sides 13 include apertures 24 for receiving locking screws 25. Also extending through the body 12 from the back surface 19 to the front surface 15 are apertures 27 for receiving fixation screws 26.

The positioning apparatus 10 receives and holds angular adjustment block generally indicated at 32. Angular adjustment block 32 includes a front surface 34 having wings 36 sized to be received by the slots 16 in the positioning body 12 to hold the angular adjustment block 32. The angular adjustment block 32 is locked into place in the positioning body 12 by means of locking screws 25, which extend through apertures 24 in the positioning body 12 and contact the wings 36 of the angular adjustment block 32 to secure the angular adjustment block 32 to the positioning body 12. The angular adjustment block 32 establishes the angular alignment and anterior/posterior location of the positioning apparatus 10.

The angular adjustment block 32 also includes back surface 38 and an aperture 40 extending from the back surface 38 through the angular adjustment block 32 to the front surface 34. The aperture 40 receives an intermedullary rod 42 therethrough. The intermedullary rod 42 comprises a shaft 43 and a handle 44. The shaft 43 extends through the angular adjustment block 32 and into the intermedullary canal which extends along the axis of the femur to aid in establishing the orientation of the resection apparatus of the present invention as hereinafter described.

The rotational alignment device, generally indicated at 50, includes a shaft 51 having a groove 52 therealong and a block 53 having a back surface 54 and wings 56. The rotational alignment device 50 is interconnected with the positioning body 12 by means of the wings 56 received in slots 16 of the positioning body 12. The rotational alignment device 50 may be secured to the positioning body 12 by means of locking screws 25 which extend through apertures 24 in the positioning body 12 to contact the wings 56. The locking screws 25 may be made of various configurations depending upon their specific function. Importantly, the locking screws 25 are used to rigidly affix one component or device to another to ensure that the relative locations and orientations are maintained despite the rigors of surgery.

Figure 2:
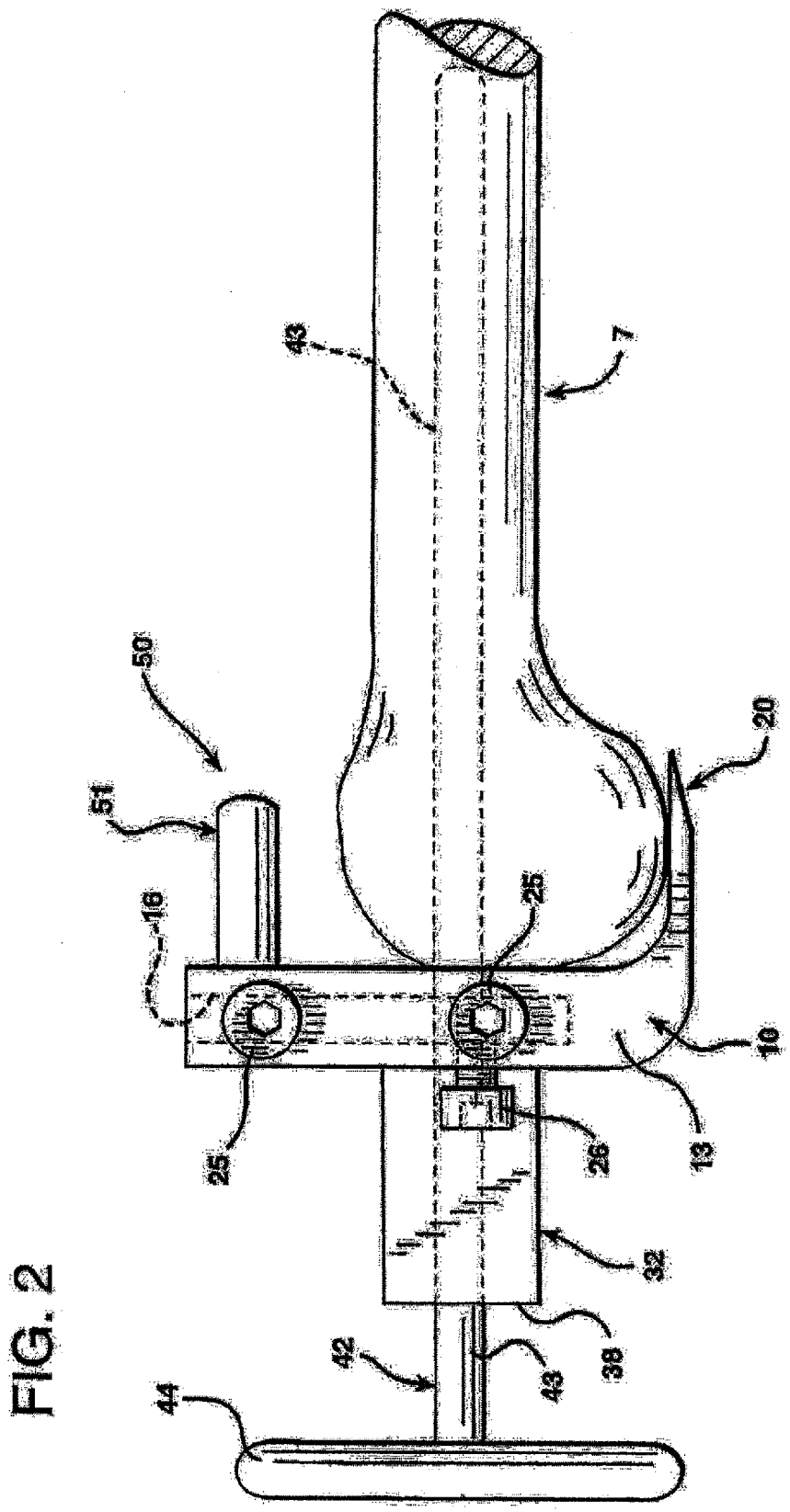
FIG. 2 is a side plan view of the guide device of the resection apparatus of FIG. 1 attached to a distal human femur.
Figure 7:
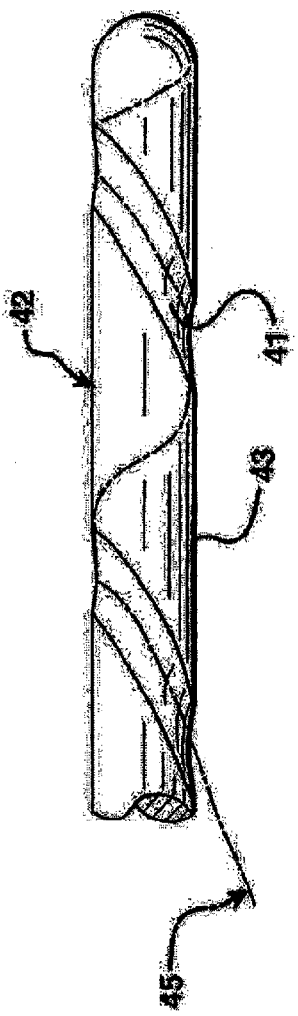
FIG. 7 is a side plan view of an intermedullary rod having a helical groove for use with the resection apparatus shown in FIG. 1.

As shown in FIG. 2, wherein the positioning body 12 is fitted with the angular adjustment block 32 and the rotational alignment device 50, the entire positioning apparatus 10 is connected to a human femur 7 by means of the shaft 43 of the intermedullary rod 42. The shaft 43 extends through the angular adjustment block 32, and thereby through the positioning body 12 into the intermedullary canal which extends along the axis of the femur 7. The intermedullary rod 42, shown in FIG. 7, has a groove 41 transversing a helical path 45 along the axis of the shaft 43. The groove 41 relieves intermedullary pressure that leads to fatty embolisms. The basic concept of the intermedullary rod 42 with the groove 41, is that as it is inserted into the femur, which contains liquid fatty tissue, the liquid fatty tissue is drawn up the groove 41 of the intermedullary rod 42 to draw the fatty liquid tissue out of the femur. Preferably, the intermedullary rod would have a hexagonal head, (not shown) to permit it to be driven by a powered device such as an electrical hand held tool. Importantly, the groove 41 does not have a cutting edge, which would risk perforation of the femoral cortex. Accordingly, the device does not cut solid material, but removes liquid material from the intermedullary canal. Therefore, the risk of fatty embolism is reduced.

After positioning body 12 is properly located against the femur 7 by means of the intermedullary rod 42 and the angular adjustment block 32, fixation screws 26 may be advanced through the apertures 27 in the positioning body 12 until they make contact with the distal femoral condyles of the femur 7, and are then driven into the distal femoral condyles of the femur 7 to initially affix the positioning apparatus to the distal femur 7. It should be noted that the fixation screws 26 may also be advanced and adjusted to make up for deficiencies in the distal femoral condyles. Accordingly, the positioning body 12 is positioned such that the front surface 15 is put into contact with the distal femoral condyles by direct contact, and the tongue 20 is positioned under the femur 7 and in contact therewith.

As can be seen in FIG. 2, the shaft 51 of the rotational alignment device 50 extends above the femur 7 and allows for rotation of the pattern device 59, hereinafter described, about the distal femur 7. Additionally, the rotational alignment device 50 allows for the anterior/posterior positioning of the pattern device 59 with respect to the femur 7. Importantly, the configurations of the positioning body 12, the angular adjustment block 32 and the rotational alignment device 50 are not limited to the structure set forth herein, but may be of different shapes and may interconnect in different ways. These components may even be formed as a unitary or partially unitary device.

Figure 3:
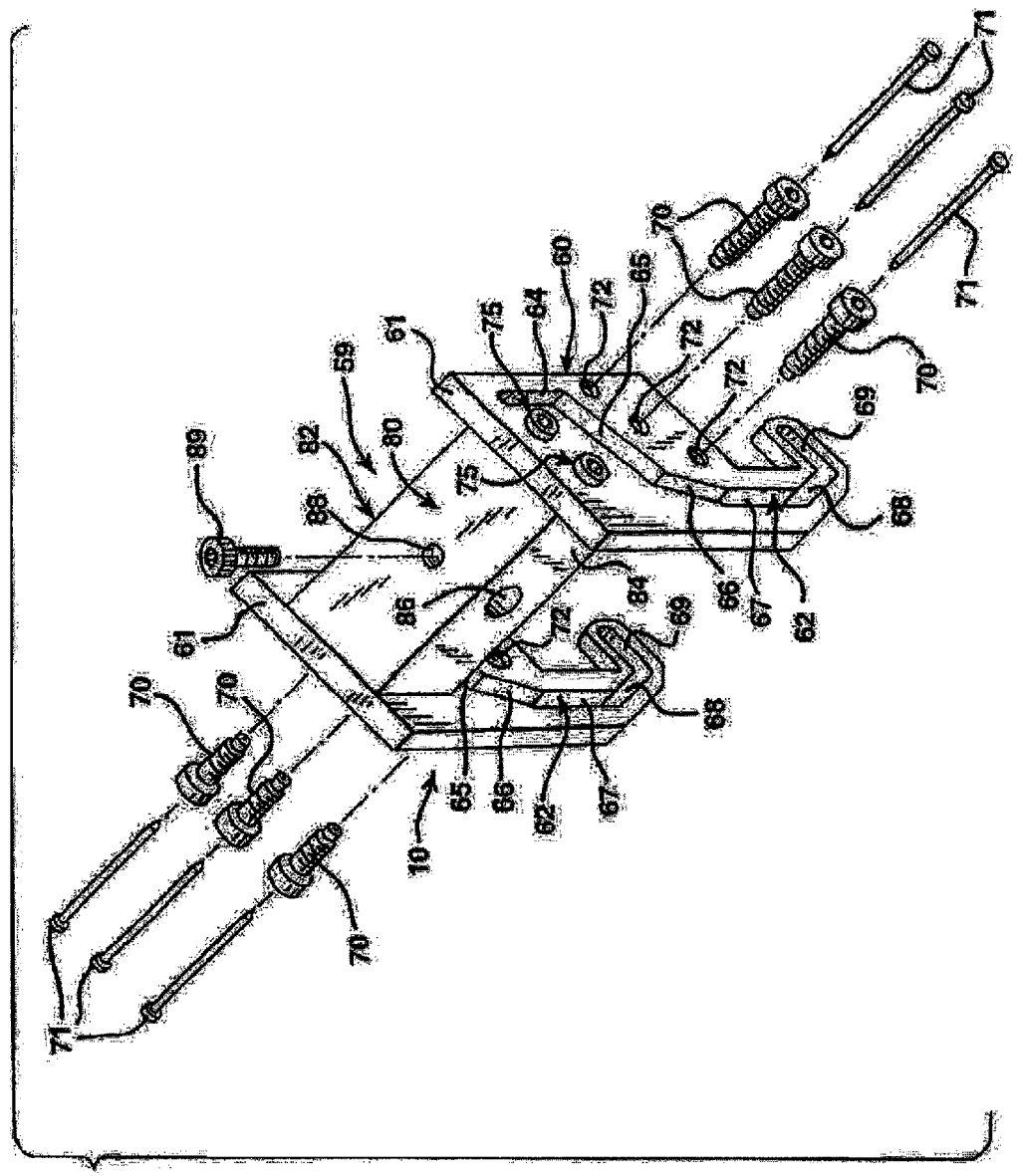
FIG. 3 is an exploded view of the pattern device of the resection apparatus of the present invention.

As shown in FIG. 3, the pattern device 59 includes pattern plates 60 having tops 61, and cutting paths, generally indicated at 62, extending therethrough. The cutting paths 62 outline the desired resection shape of the distal femur 7.

Generally, the cutting paths 62 could include a first vertical path 64, extending to a first diagonal path 65, extending to a second diagonal path 66, extending to a second vertical path 67, extending to a third diagonal path 68 and then extending to a horizontal path 69. Alternatively, the cutting paths 62 could describe any desired resection shape for the femur 7. The pattern plates 60 also include locking screws 75 for interconnecting the pattern plates 60 with a crossbar 80.

The pattern device 59 of the present invention preferably includes two pattern plates 60 held in a spaced apart relationship by crossbar 80. The crossbar 80 separates the pattern plates 60 sufficiently to permit the pattern plates 60 to extend along the sides of the distal femur 7. The crossbar 80 includes a front surface 82, back surface 84, a top surface 83, a central aperture 86 extending from the front surface 82 to the back surface 84, a lock aperture 88 extending through the top surface 83, and a lock screw 89. The central aperture 86 of the crossbar 80 receives the shaft 51 of the rotational alignment device 50. Accordingly, the pattern device 59 is interconnected with the positioning apparatus 10 so that the pattern device 59 is properly oriented with respect to the femur 7. Upon proper positioning of the crossbar 80, with respect to the shaft 51 of the rotational alignment device 50, lock screw 89 is extended through lock aperture 88 to contact the shaft 51 to lock the crossbar 80 and, accordingly, the pattern device 59, onto the shaft 51 of the rotational alignment device 50, and accordingly, to positioning apparatus 10. This completed assembly is attached to the femur 7, as shown in FIG. 4.

Figure 4:
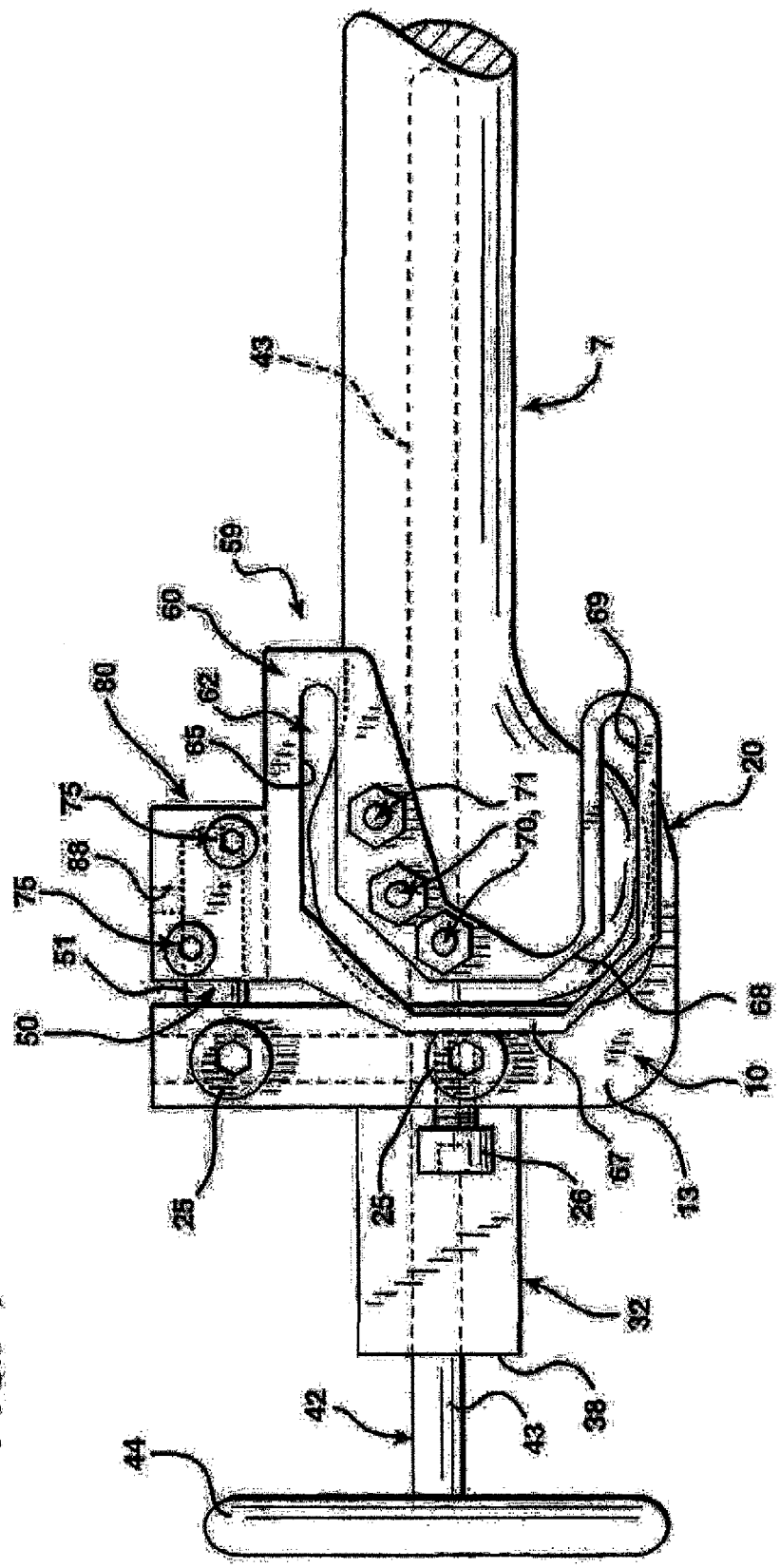
FIG. 4 is a side plan view of the resection apparatus shown in FIG. 2 with the pattern device fixed to the distal human femur.

As additionally shown in FIGS. 3 and 4, the pattern plates 60 include plate apertures 72 for receiving cannulated screws 70 which have apertures extending therethrough for receiving fixation nails 71 therethrough. Accordingly, after the pattern device 59 is interconnected with the positioning apparatus 10, and properly located and oriented with respect to the femur 7, the cannulated screws 70 are extended through the plate aperture 72 to contact the sides of the distal femur 7. Then, in order to fix the pattern plates 60 with respect to the femur 7, the fixation nails 71 are driven into the distal femur 7 to lock the pattern plate 60 into position on the distal femur 7. The cannulated screws 70 have sharp leading edges for allowing decisive purchase in the distal femur 7 before the introduction of the fixation nails 71 to complete fixation of the pattern device 59 to the distal femur 7.

The pattern plates 60 by virtue of the cutting paths 62, dictate the shape of the resection of the femur 7. The cutting paths 62 are essentially channels through the pattern plates 60. The cutting paths 62 receive the cutting device and guide it as it resects the surface of the distal femur 7. The pattern plates 60 straddle the distal femur 7 mediolaterally and are suspended by the crossbar 80. Likewise, crossbar 80 maintains the proper relationship between the pattern plates 60 before and during the resection of the distal femur 7. The location of the crossbar 80 and accordingly, the pattern plates 60, may be adjusted with respect to the positioning apparatus 10 by adjusting the position of the block 53 of the rotational alignment device 50 within the slots 16 of the positioning body 12, and locking the same with locking screws 25.

Figure 5:
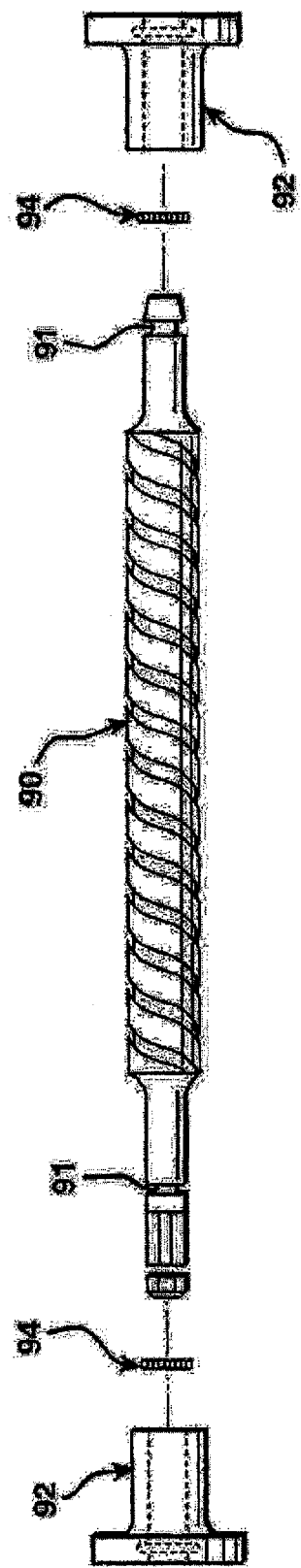
FIG. 5 is an exploded front view of the cutting device of the resection apparatus of the present invention.

The cutting paths 62 in the pattern plates 60 receive and guide the cutting device shown in FIG. 5 and generally indicated at 90. The cutting device 90 performs the actual cutting of the femur 7 to resect the femur 7. The cutting device may be of any known configuration. In a preferred embodiment, the cutting device is a drill. The drill 90 is generally cylindrical in shape and may possess helical cutting teeth along its length to cut the femur 7. The drill 90 includes a hexagonal end 95 to permit the use of an electric powered drive, typically an electric drill. Further, the drill 90 includes drill bushings 92 at the ends of the drill 90 to provide a non-metallic bearing between the cutting paths 62 in the pattern plates 60 to avoid galling and to ensure smooth articulation of the drill 90 along the cutting path 62. Positioned between the drill bushings 92 and the drill 90 are retention springs 94 which are essentially coil springs retained within the drill bushings 92 to allow the drill bushings 92 to be easily attached and removed from the drill 90. These retention springs 94 are commercially available in medical grade stainless steels. The drill bushings 92 retain the retention springs 94 which hold the drill bushings 92 in position 92 on the drill 90 while allowing the drill bushings 92 to rotate freely. The drill 90 may also include circumferential grooves 91 for allowing attachment and retention of the drill bushings 92 by means of the retention springs 94. Importantly, the configuration of the drill 90 can vary in accordance with what is known in the art, as long as the cutting device can follow the cutting paths 62 in the pattern plates 60 to resect the femur 7.

Figure 6:
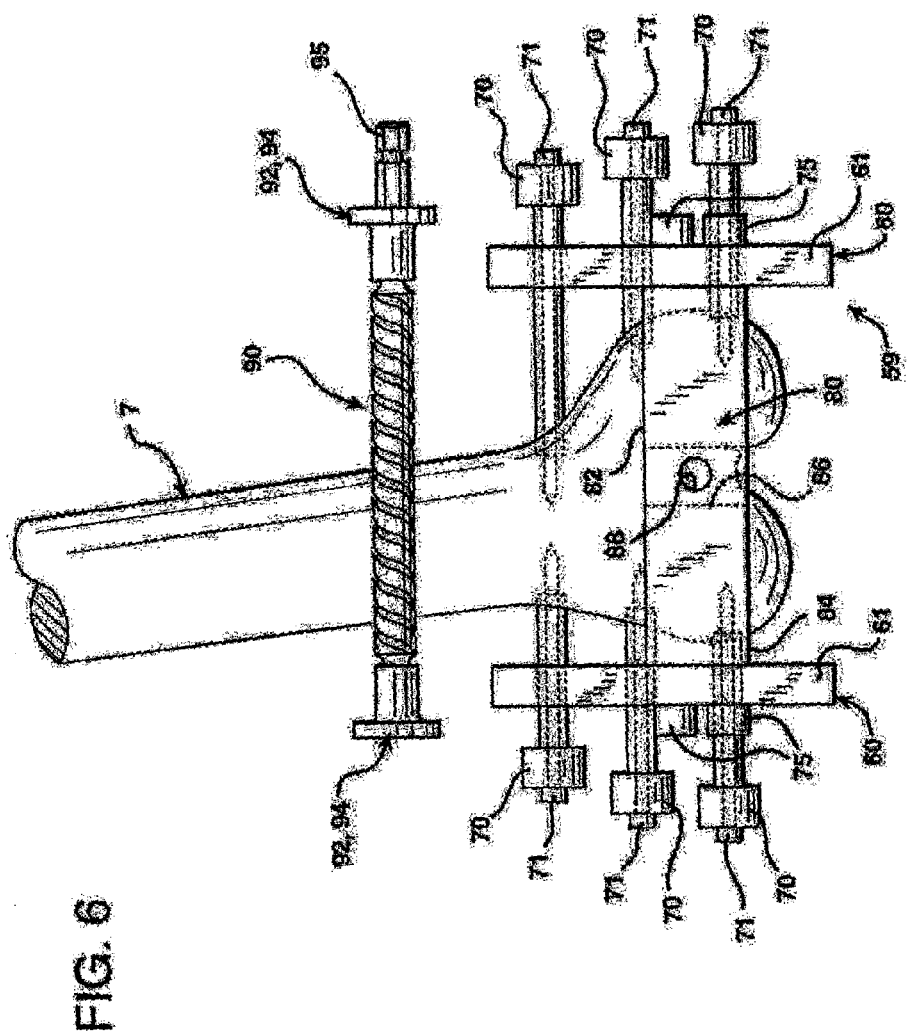
FIG. 6 is a top plan view of the pattern device and the cutting device of the resection apparatus of the present invention affixed to the distal human femur.

As shown in FIG. 6, after the pattern device 59 is attached to the distal femur 7, and positioned accordingly by means of the positioning apparatus 10, and secured to the distal femur 7 by means of cannulated screws 70 and fixation nails 71, positioning apparatus 10 may be removed from connection to the distal femur 7 leaving the pattern device 59 attached to the distal femur 7 to permit resecting of the distal femur. The drill 90 is then positioned within the cutting paths 62 between the pattern plates 60. Next the drill 90 is rotated by power means in connection with the hexagonal end 95, and is then moved along the cutting path 62 to resect the distal femur 7. It should also be noted that the cutting means could be operated by hand.

Instead of two pattern plates 60, a single pattern plate could be employed if it is sufficiently sturdy to support and guide the drill. The pattern plates 60 may also comprise plates having edges in the shape of the desired distal femoral resection pattern. Thus, the cutting device may be drawn along the edges of the pattern plates to resect the distal femur. Further, any cutting device that can be employed to follow the cutting paths in the pattern plates is considered to be within the scope of this invention.

The resection apparatus of the present invention, through proper use as previously described, provides extremely accurate and reproducible bone cuts. While the anterior and distal areas of the femur will almost always be able to be prepared in this manner, interference from soft tissue such as fat and ligaments may prohibit satisfactory preparation of the posterior femur. The preparation of any remaining femoral surfaces may be completed in any manner known in the art after using the instrumentation of the present invention.

Figure 8:
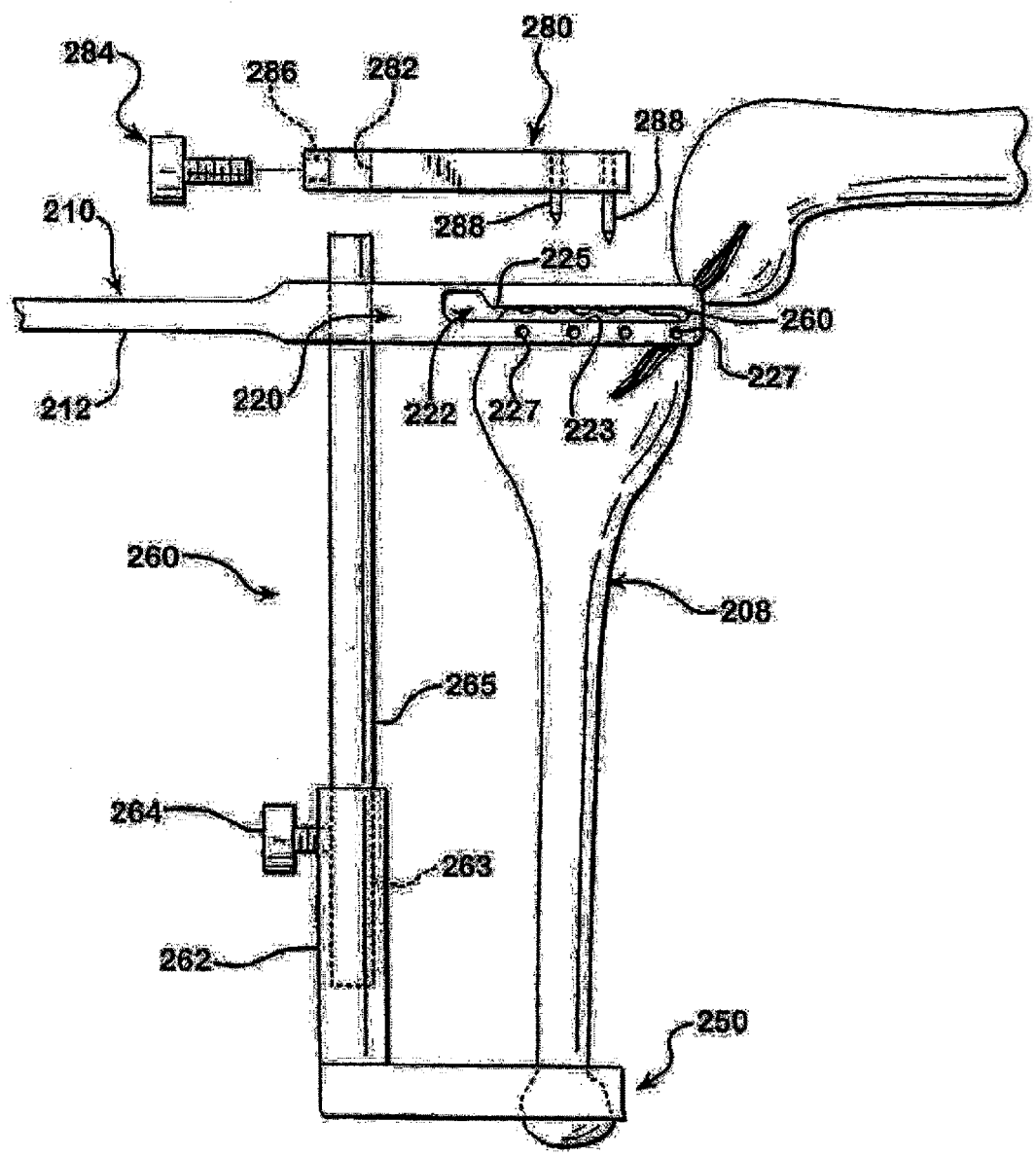
FIG. 8 is a partially exploded side plan view of an embodiment of the tibial resection apparatus of the present invention shown attached to the tibia, wherein the cutting guide clamps are of a fixed size and directly interconnect with the alignment rod.
Figure 9:
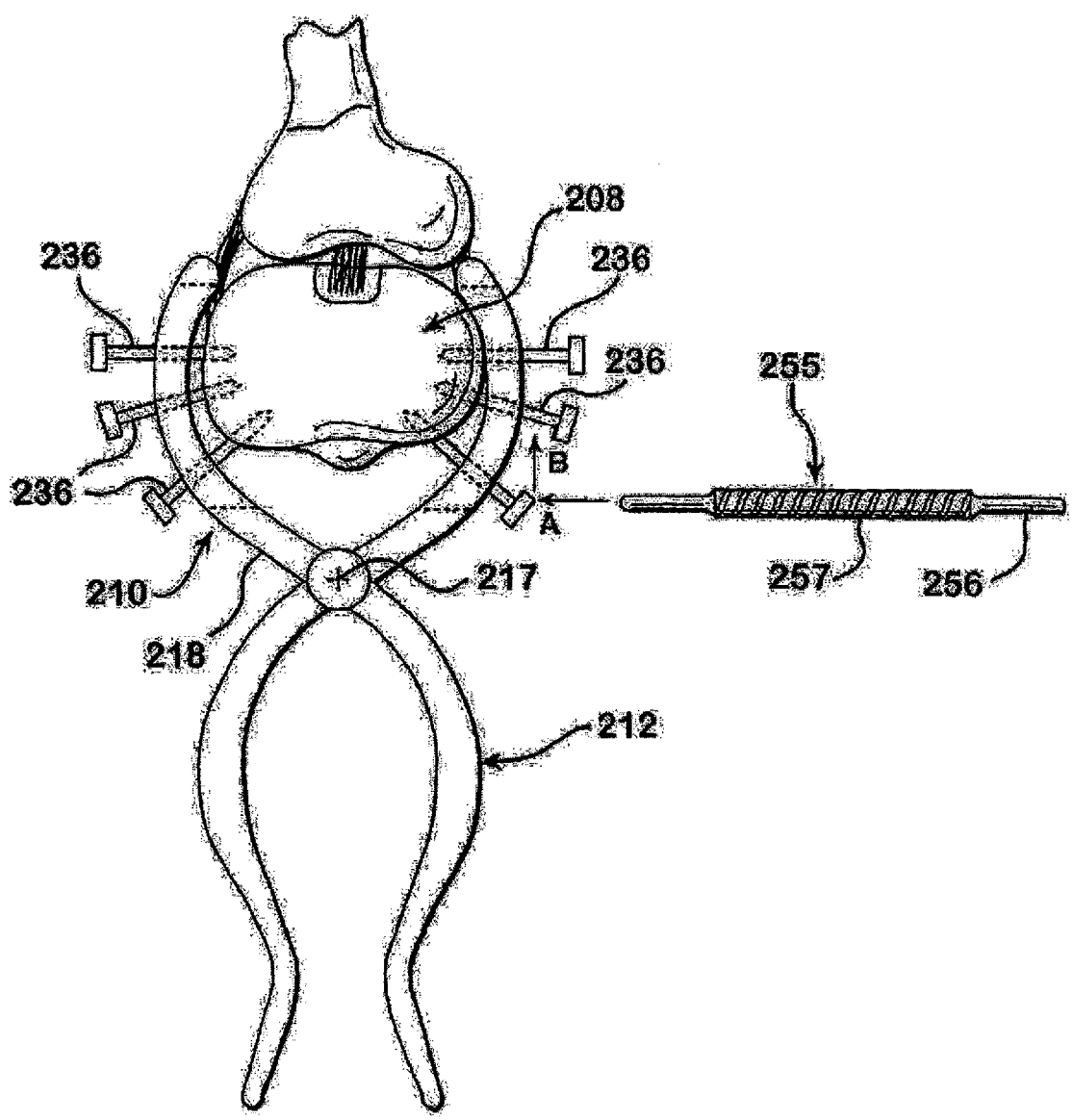
FIG. 9 is a top plan view of the tibial resection apparatus, shown in FIG. 8 prior to insertion of the milling bit into the apparatus.
Figure 10:
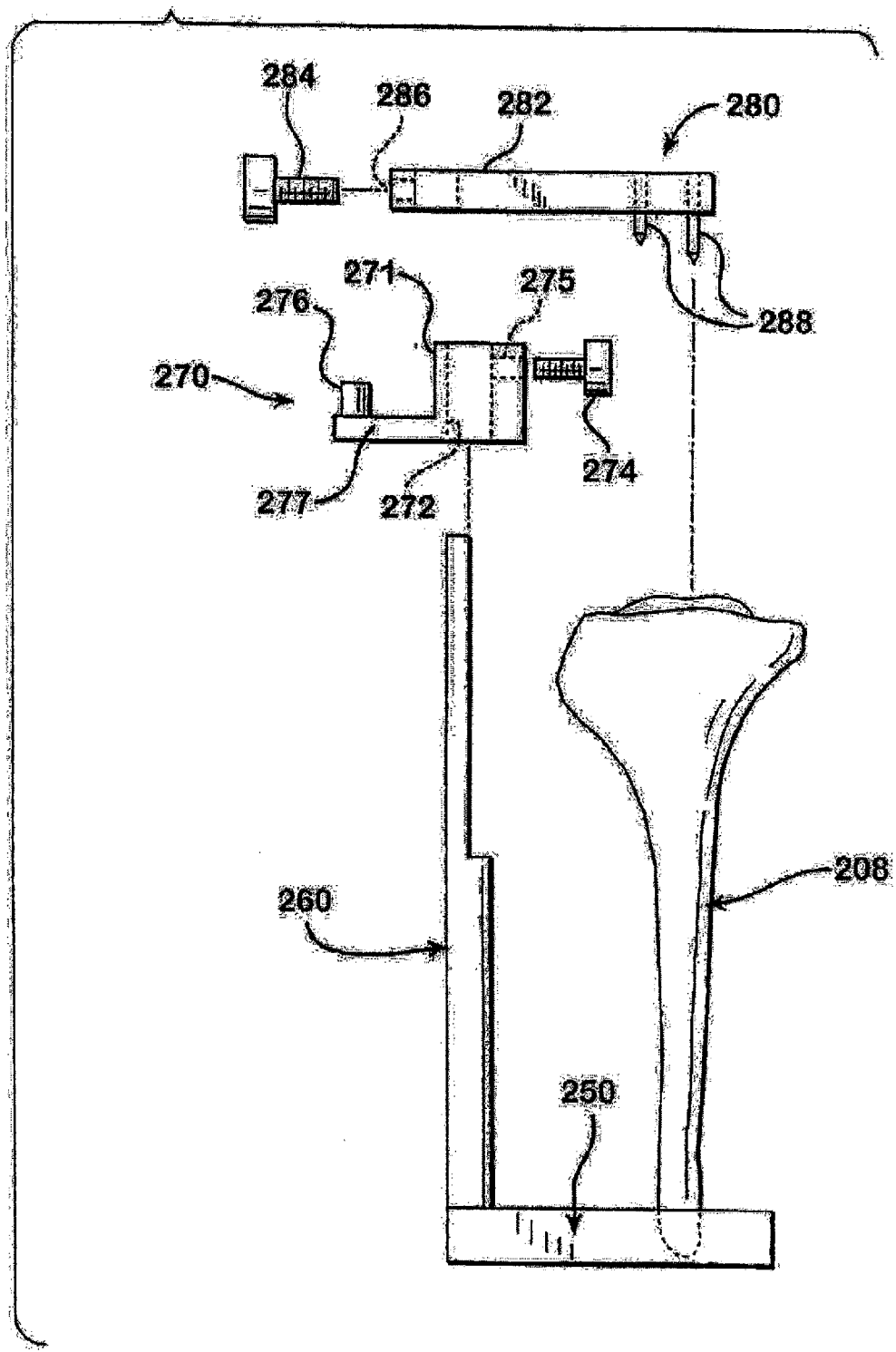
FIG. 10 is a partially exploded side plan view of another embodiment of the tibial resection apparatus shown in FIG. 8, wherein the cutting guide clamps interconnect with the alignment rod by means of a cutting guide clamp linkage.
Figure 11:
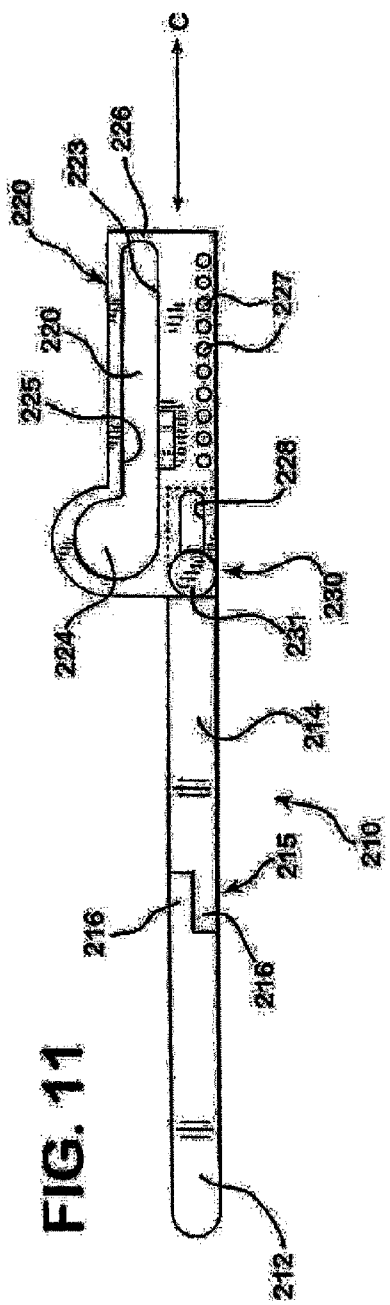
FIG. 11 is a side plan view of an embodiment of the cutting guide clamps shown in FIG. 8, wherein the cutting guide clamps are adjustable.
Figure 12:
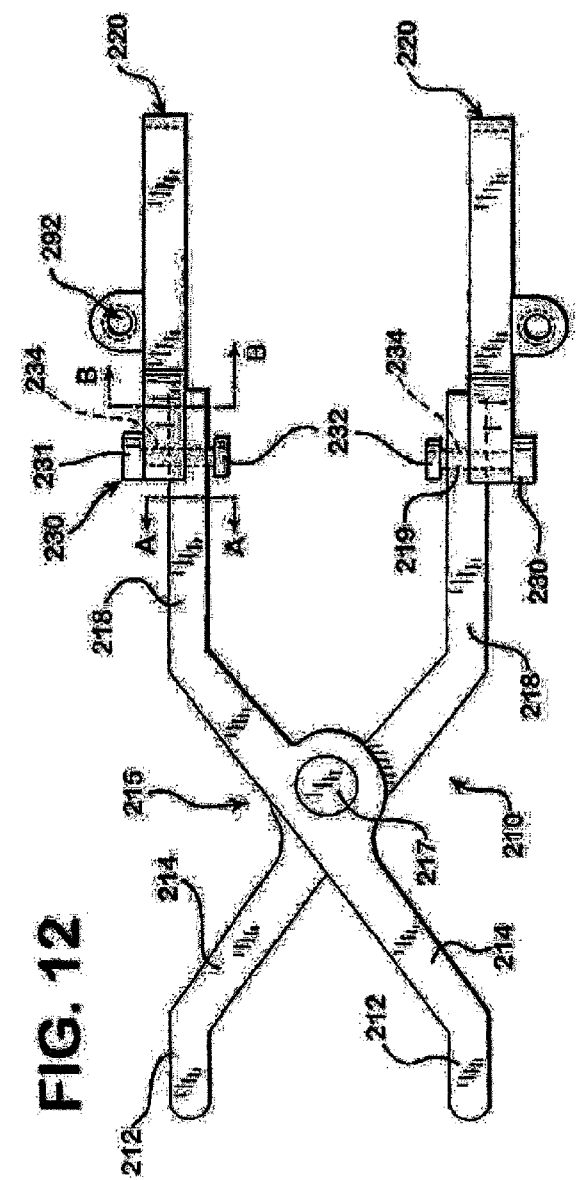
FIG. 12 is a top plan view of the cutting guide clamps shown in FIG. 11.
Figure 13:
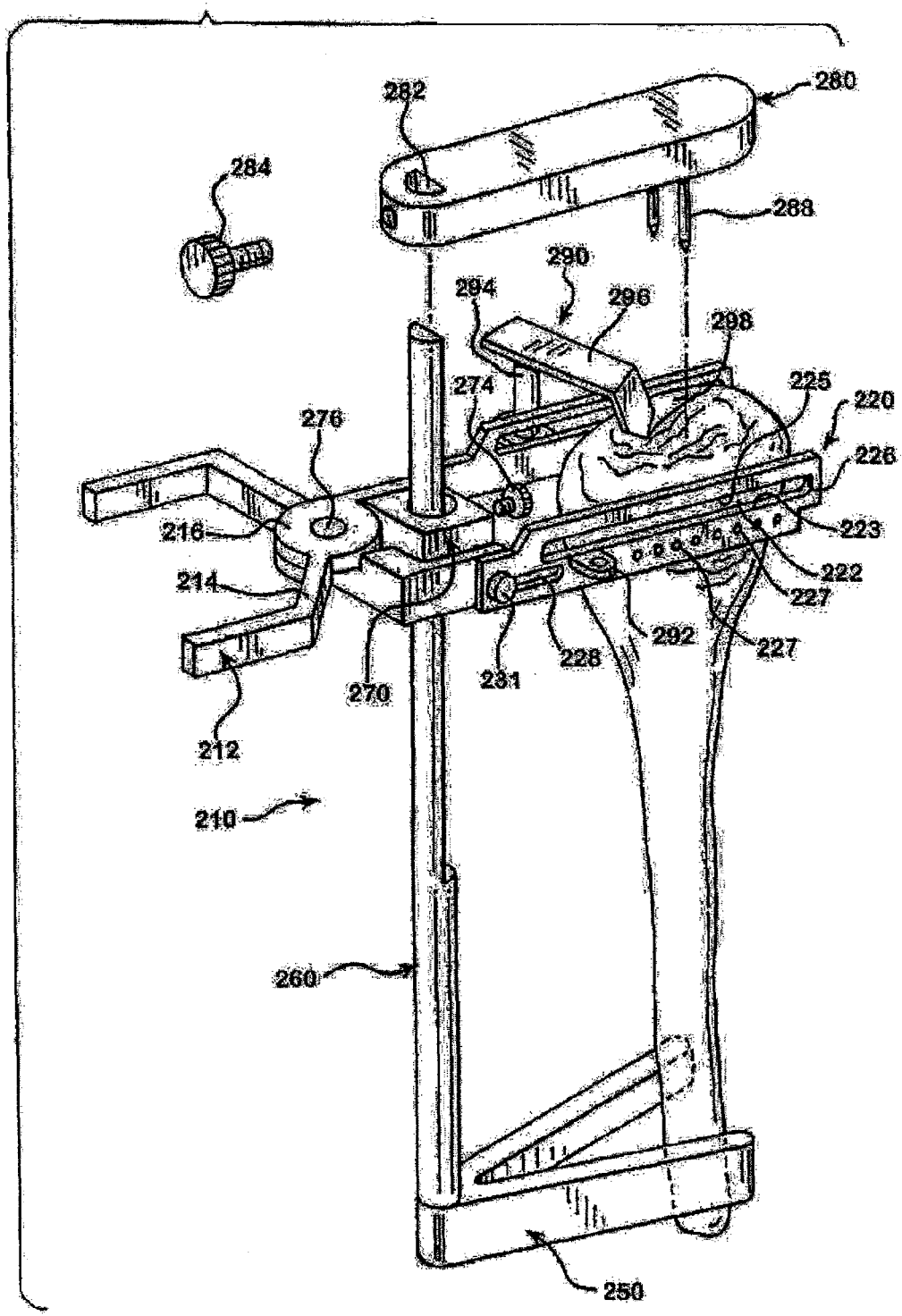
FIG. 13 is a perspective view of an embodiment of the tibial resection apparatus shown in FIG. 8, showing the proximal tibial referencing stylus attached to the cutting guide clamps.

As shown in FIGS. 8-13, the tibial resection apparatus of the present invention includes a number of components, namely, cutting guide clamps generally indicated at 210, cutting guides generally indicated at 220, ankle clamp generally indicated at 250, alignment rod generally indicated at 260, cutting guide clamp linkage generally indicated at 270, fixation block generally indicated at 280, proximal tibial referencing stylus generally indicated at 290, and milling bit generally indicated at 255. It should be noted that the cutting guides 220 may be formed integrally with the cutting guide clamps 210 as shown in FIGS. 8 and 9, or as separate members as shown in FIGS. 11, 12 and 13. Also, the cutting guides 220 may ride the alignment 260 as shown in FIGS. 8 and 9, or they may interconnect with the alignment rod 260 by means of cutting guide clamp linkage 270, as shown in FIGS. 11, 12 and 13.

As shown in FIG. 8, the ankle clamp 250 is attached at or just above the ankle and exterior to the skin. Any conventional ankle clamp may be used to firmly engage the ankle, or to engage the tibia above the ankle, to obtain a reference point for the other components of the present invention.

The ankle clamp is interconnected with and locked into place on the alignment rod 260 in any way known in the art. Preferably, though not necessarily, the alignment rod 260 is vertically adjustable with respect to the ankle clamp 250. This vertical adjustment can be achieved at the ankle clamp 250, at the interconnection of the ankle clamp 250 and the alignment rod 260, or within the alignment rod 260 itself. As shown in FIG. 8, the alignment rod includes a first lower end 262 having an aperture 263 extending vertically therein for telescopically receiving a second upper end 265 of the alignment rod 260. A set screw 264 is provided for fixing the upper end 265 with respect to the lower end 262.

The fixation block 280 is interconnected with an upper end of the alignment rod 260 by means of an aperture 282 in the fixation block 280 sized to receive the alignment rod 260 therethrough, or in any other manner known in the art. A set screw 284 may be provided to extend into the fixation block 280, through set screw aperture 286 in fixation block 280, to contact the alignment rod 260, to lock the fixation block 280 onto the alignment rod 260. The fixation block 280 additionally includes apertures extending vertically therethrough for receiving fixation pins 288 for affixing the fixation block 280 to the proximal tibia 208.

In operation, the ankle clamp 250 is attached about the ankle, or about the tibia just above the ankle, on the exterior of the skin. The fixation block 280 is already interconnected with the alignment rod 260. It is preliminarily positioned over the proximal tibia 208, and one of the fixation pins 288 is driven into the proximal tibia 208. Thereafter, the alignment rod 260 is adjusted to establish proper varus/valgus alignment and flexion/extension angulation as is conventionally known. Upon proper alignment of the alignment rod 260, the other fixation pin 288 is driven into the proximal tibia 208 to completely fix the fixation block 280 to the proximal tibia 208 to lock in the proper alignment of the alignment rod 260. Then, the fixation block 280 may be locked into position on the alignment rod 260.

After properly aligning and locking in the alignment of the alignment rod 260, the cutting guide clamps 210 and the cutting guides 220 may be employed. The cutting guide clamps 210 are interconnected with the alignment rod 260 by means of cutting guide linkage 270. Alternatively, the cutting guide clamps 210 could directly interconnect with the alignment rod 260 through apertures in the cutting guide clamps 210, as shown in FIGS. 8 and 9. As shown in FIG. 10, the cutting guide clamp linkage 270 comprises a body 271 having an alignment rod aperture 272 for receiving and riding the alignment rod 260 and a pivot locking set screw 274 which extends into the cutting guide clamp linkage 270 through set screw aperture 275 for contacting the alignment rod 260 and locking the cutting guide clamp linkage 270 with respect to the alignment rod 260. It should be pointed out that it may be desirable for the alignment rod 260 to have a flattened surface extending longitudinally along the alignment rod 260 for co-acting with set screw 274 for maintaining proper alignment between the cutting guide clamp linkage 270 and the alignment rod 260.

The cutting guide clamp linkage 270 also includes a pivot shaft 276 rigidly interconnected with the body 271 of the cutting guide clamp linkage 270 by member 277 to position the pivot shaft 276 a distance away from the body 271 such that the cutting guide clamps 210 can be interconnected with the pivot shaft 276 and can be properly utilized without interfering with the body 271 of the cutting guide clamp linkage 270.

After the alignment rod 260 is properly aligned and locked into position, the cutting guide clamp linkage 270 is moved into its approximate desired position at the proximal tibia 208. It should be noted that the cutting guide clamp linkage 270 of present invention is positioned on the alignment rod 260 at the beginning of the procedure, prior to aligning the alignment rod 260, and prior to interconnecting the fixation block 280 with the alignment rod 260. However, it is within the scope of the present invention to provide a cutting guide clamp linkage 270 which is attachable to the alignment rod 260 after the alignment rod 260 has been aligned and locked into position.

After the cutting guide clamp linkage 270 is preliminarily approximately located, it is locked into place on the alignment rod 260. Thereafter, the cutting guide clamps 210 may be interconnected with the pivot shaft 276 by means of corresponding pivot apertures 217 in the cutting guide clamps 210.

As shown in FIGS. 11 and 12, the cutting guide clamps 210 include opposing hand grips 212 for grasping and manipulating the cutting guide clamps 210. Crossbar members 214 extend from the hand grips 212 to clamp members 218. The crossbar members 214 cross over each other at cross over point 215 whereat the crossbar members 214 have mating recessed portions 216 which function to maintain the hand grips 212 in the same plane as the clamp members 218. At the cross over point 215, the crossbar members 214 can pivot with respect to each other such that movement of the hand grips 212 towards each other moves the clamp members 218 together, and likewise, movement of the hand grip members 212 away from each other serves to move the clamp members 218 apart in the same manner as scissors or pliers. At the cross over point 215, the crossbar members 214 have corresponding pivot apertures 217 for receiving the pivot shaft 276 of the cutting guide clamp linkage 270. Thus, the cutting guide clamps 210 pivot about the pivot shaft 276 of the cutting guide clamp linkage 270. It should be noted that the crossbar members 214 could be interconnected with each other by a rivet or other means known in the art, or could be entirely independent pieces which co-act as set forth above only upon being seated on pivot shaft 276.

The clamp members 218 of the cutting guide clamps 210 include cutting guide adjustment screw apertures 219 at the far ends thereof for receiving A-P adjustment screws 230 for adjustably interconnecting the cutting guides 220 with the clamp members 218, for adjustable movement in the direction shown by arrow C in FIG. 11. The clamp members 218 may be adjustably interconnected with the cutting guides 220 in any way known in the art. In one embodiment, the cutting guide adjustment screw apertures 218 are threaded and the cutting guides 220 have corresponding elongated apertures 228 extending over a portion of the length thereof for receiving the A-P adjustment screws at a desired location therealong. The A-P adjustment screws include a head 231, a retaining head 232, and a threaded shaft 234. When the cutting guides 220 are positioned correctly with respect to the clamp members 218, the A-P adjustment screws 230 are tightened down to lock the cutting guides 220 onto the clamp members 218 by actuating the head 231 to turn down the threaded shaft 234 with respect to the clamp member 218. Note the retaining head 232 of the A-P adjustment screws prevent the shaft 234 from being backed off out of engagement with the clamp member 218.

Figure 14:
FIG. 14 is a cross-sectional view of the profile of the ends of the clamp members taken along line A-A in FIG. 12.
Figure 15:
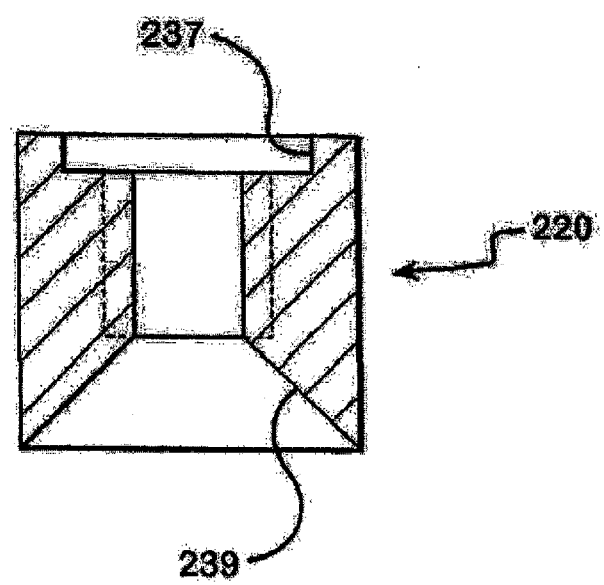
FIG. 15 is a cross-sectional view of the profile of the ends of the cutting guides taken along line B-B in FIG. 12, the ends of the clamps mating with the ends of the cutting guides for positioning the cutting guides with respect to the clamps.

As shown in FIGS. 14 and 15, respectively, the clamp members 218 are shaped with opposing interior edges having chamfers 238 and the opposite exterior edges of the cutting guides 220 have mating recesses 239, both of said profiles extending along the contacting surfaces of the clamp members 218, as seen along line A-A in FIG. 12, and the cutting guides 220, as seen along line B-B in FIG. 12, to maintain a proper planar alignment therebetween. It should of course be noted that any other method known in the art may be employed to maintain the clamp members 218 and the cutting guides 220 in alignment. Additionally, the cutting guides 220 may include A-P adjustment screw recesses 237 for receiving the head 231 of the A-P adjustment screw 230.

The cutting guides 220 further include tibia attachment means for attaching the cutting guides 220 to the tibia 208. Any known attachment means may be employed to attach the cutting guides 220 to the tibia 208. As shown in FIGS. 9 and 11, a preferred attachment means for attaching the cutting guides 220 to the tibia 208 are pins 236 extending through pin apertures 227 in the cutting guides 220. The pins 236 may be captured in the pin apertures 227, or they may be entirely separate. Preferably, means exist on the cutting guides 220 for preliminarily attaching the cutting guides 220 to the tibia 208 prior to pinning the cutting guides 220 thereto, so that after proper positioning of the cutting guides 220, the hand grips 212 can be actuated by squeezing the hand grips 212 together to contact the cutting guides 220 against the tibia 208 so that the cutting guides 220 are preliminarily attached to the tibia 208. Such means may include a plurality of small pins captured by the cutting guide 220, or any other suitable means. After the preliminary attachment of the cutting guides 220 to the tibia 208, final attachment may be made by attachment pins 236 or by any other means known in the art.

The cutting guides 220, importantly, include cutting slots 222 which each comprise lower cutting slot guide surface 223 and upper cutting slot retaining surface 225, as well as cutting slot entrance and exit 224 at one end thereof and cutting slot end wall 226 at the other end thereof. The cutting slot 222 is of a length sufficient to extend across the proximal tibia 208, at a desired angle to the intermedullary canal, at the widest point of the proximal tibia 208, to allow the entire upper surface of the proximal tibia 208 to be cut. The cutting slot 222 is of a size sufficient to receive a cylindrical milling bit 255 such as that shown in FIG. 16 and described in U.S. Pat. No. 5,514,139, filed Sep. 2, 1994 by Goldstein, et al. The milling bit 255 comprises central cutting portion 257 having helical cutting teeth along its length for cutting bone. The milling bit 255 further comprises spindles 256 extending from the central cutting portion 257 for supporting the central cutting portion 257.

Figure 16:
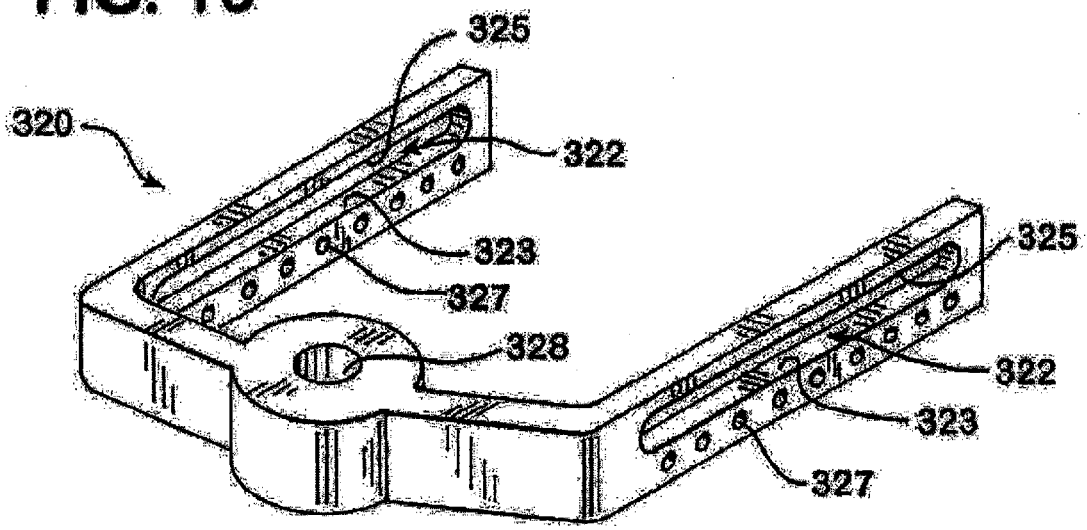
FIG. 16 is a perspective view of an alternate embodiment of a U-shaped cutting guide for use in the present invention.

The milling bit 255 is inserted into and received in the cutting slot 222 through cutting slot entrance 224, along the direction shown by arrow A in FIG. 16. Note that the cutting slot entrance 224 may be of a wider slot area or an upturned portion of the slot 222 or the milling bit 255 may merely be inserted and removed from the slot 222 at an end thereof. The spindles 256 extend through and co-act with the lower cutting guide surface 223 and the upper retaining surface 225 of the cutting slot 222 to guide the milling bit 255 along the cutting slot 222 to resect the proximal tibia 208, along the direction shown by arrow B in FIG. 16. At an end of one or both of the spindles 256 is a means for engaging the milling bit 255 with a drive means such as an electric drill, or other drive means. This engagement means may include a hexagonal head on one of the spindles, or any other suitable method of engagement known in the art. Additionally, bushings may be employed, either on the milling bit 255 or captured by the cutting slot 222, to provide a non-metallic bearing between the spindles 256 of the milling bit 255 and the cutting slot 222 to avoid galling and to ensure smooth articulation of the milling bit 255 along the cutting slots 222. Importantly, the configuration of the milling bit 255 may be varied in accordance with what is known in the art, as long as the cutting device can follow the cutting path of the cutting slot to resect the proximal tibia. Additionally, it should also be pointed out that other cutting tools may be used in accordance with the present invention, including an oscillating or reciprocating saw or other means for resecting the tibia by following the cutting slots on the cutting guides.

After the cutting guide clamps 210 are preliminarily located along the alignment rod 260, the cutting guides 220 are adjusted with respect to the clamp members 218 for proper anterior-posterior positioning to extend along the proximal tibia 208 for guiding the milling bit 255. Importantly, the cutting slots 222 should extend beyond the edges of the proximal tibia 208. Once proper anterior-posterior alignment is obtained, the cutting guides 220 may be locked into place on the clamp members 218.

Thereafter, a proximal tibial referencing stylus 290 may be attached to a referencing bracket 292 on the cutting guides 220. The referencing bracket 292 may be positioned in any location on the cutting guides 220, or on any other convenient component of the tibia resection system of the present invention. Alternatively, the referencing stylus 290 may be formed as part of a component of the present invention, or as a separate component which could function merely by contacting the cutting guides 220 of the present invention or any other component thereof. The referencing stylus 290, shown in FIG. 13, includes stylus body 294 which may be interconnected with the referencing bracket 292 in any manner known in the art, preferably by a quick release and connect mechanism or a threaded connection. The stylus body 294 supports a stylus arm 296, which is rotatable with respect to the stylus body 294 and configured to extend out and down from the stylus body 294 to contact the proximal tibia 208 at a tip 298 of the stylus arm 296. The stylus body 294, arm 296 and tip 298 are sized to contact the proximal tibia 208 to reference the positioning of the cutting guides 220 to cut the proximal tibia at a proper distance below the proximal tibia 208 as is known in the art. The stylus arm 296 may include more than one tip 298, such other tips extending down from the stylus body 294 in varying distances.

In operation, one determines the desired location of the stylus tip 298, unlocks the cutting guide clamp linkage 270 to permit the linkage 270 to move up and down the alignment rod 260, and places the tip 298 on the lowest point of the proximal tibia 208 to reference the position of the cutting guides with respect to the proximal tibia 208 and with respect to the alignment rod 260. Thereafter, the cutting guide clamp linkage 270 is locked to the alignment rod 260 to lock the cutting guides 220 into the proper position on the alignment rod 260, and accordingly, into proper position with respect to the proximal tibia 208. Thereafter, the hand grips 212 are actuated to press the cutting guides 220 against the proximal tibia 208 to preliminarily lock them into position on the proximal tibia 208. Next, the cutting guides 220 are fixed to the proximal tibia 208 by pins 236 or any other desired fixation means. The fixation block 280 can then be removed from the proximal tibia 208, and the proximal tibia 208 may be resected.

The cutting operation is similar to the cutting operation set forth in U.S. Pat. No. 5,514,139, filed Sep. 2, 1994 by Goldstein, et al. Essentially, the cutting operation comprises inserting the milling bit 255 into the cutting guide slots 222 through the slot entrance/exit 224 to position the central cutting portion 257 between the cutting guides 220, the spindles 256 extending through the cutting guide slots 222. After the milling bit 255 is positioned, the drive means may be interconnected therewith, actuated, and the milling bit 255 moved along the cutting slots 222 to resect the proximal tibia 208.

It should be noted that a handle may be provided for attachment to the spindle which is not driven so that such spindle may be guided evenly through the cutting slots 222 to facilitate the cutting procedure. Alternatively, a handle can be provided which interconnects with both spindles to further facilitate control of the milling bit 255 during the cutting procedure. Additionally, the bushings that fit over the spindles 256 of milling bit 255 and ride in the cutting slots 222 may be captured in the ends of the handle and the milling bit received therethrough.

Additionally, it should be pointed out that it is within the scope of the present invention to modify the cutting slots 222 such that the upper retaining surface is eliminated, and the milling bit 255 merely follows the lower cutting guide surface 223. With the cylindrical milling bit 255 herein described, this is especially viable as the milling bit 255 tends to pull down into the bone as it is cutting, thereby primarily utilizing the lower cutting guide surface 223 of the cutting guide 220.

Figure 18:
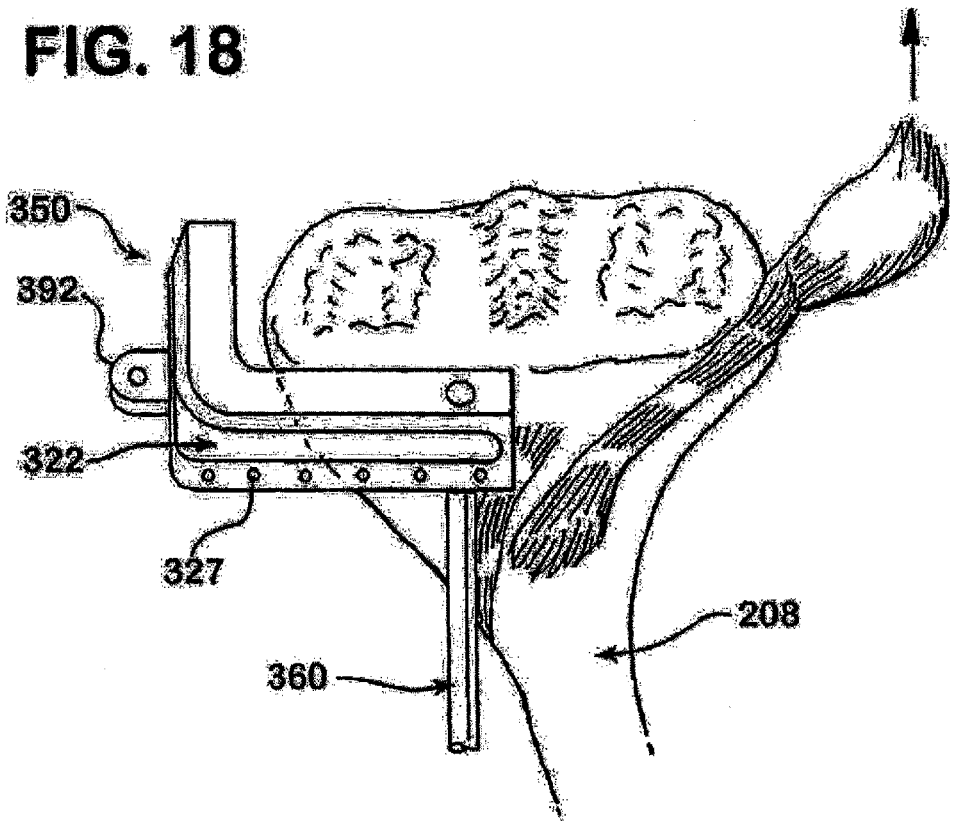
FIG. 18 is a perspective view of another alternate embodiment of a partial cutting guide for use in the present invention when the patellar tendon, patella, or quad tendon interferes with placement of the cutting guide about the tibia.
Figure 17:
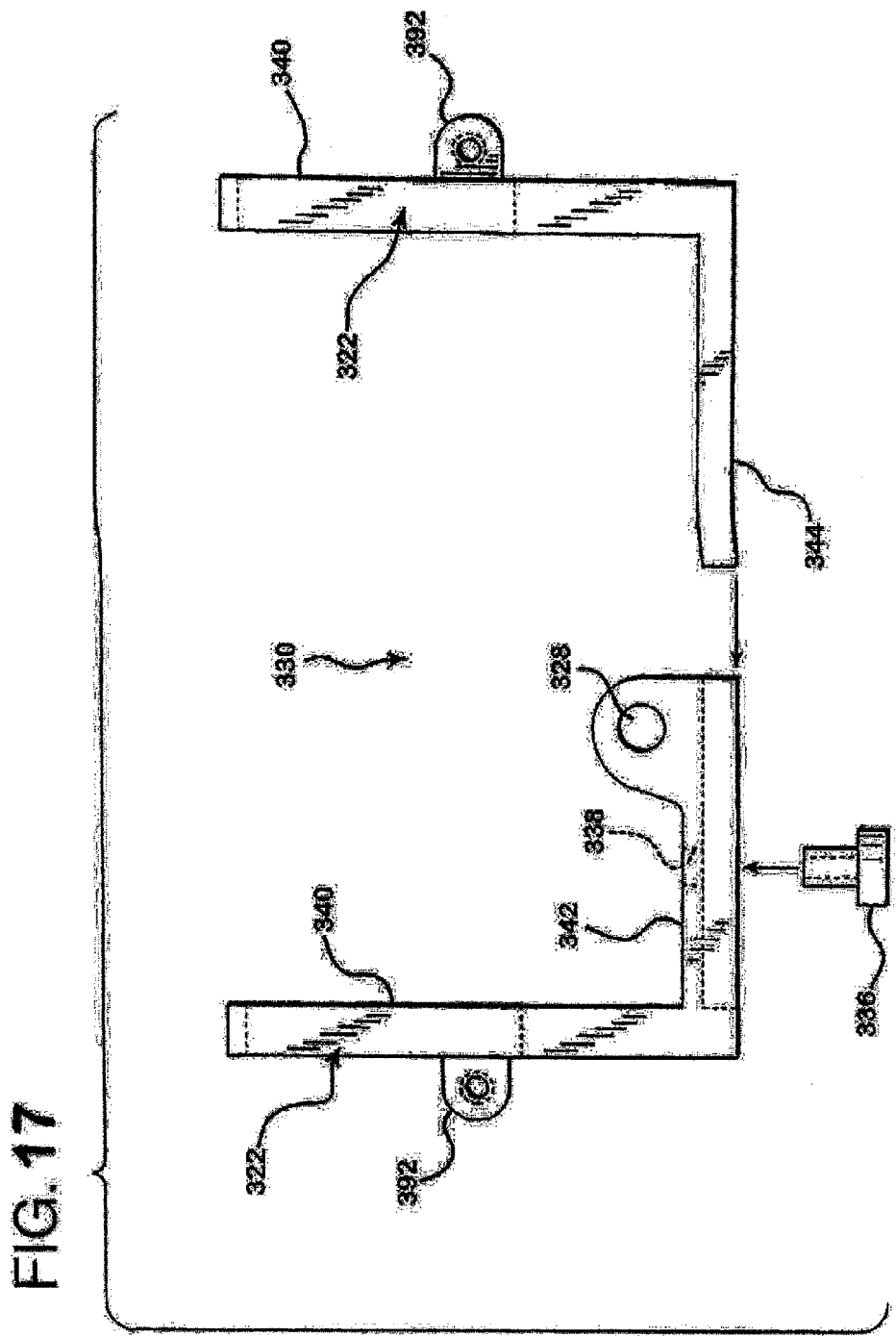
FIG. 17 is a top plan view of another alternate embodiment of a square U-shaped cutting guide for use in the present invention.

As shown in FIGS. 16-18, various other embodiments of the cutting guides are considered within the scope of the present invention. The cutting guide 320 shown in FIG. 16 is of a generally U-shaped configuration, having cutting guide slots 322, lower cutting guide surface 323, upper retaining surface 325, pin apertures 327 and alignment rod aperture 328. This cutting guide 320 is used in the same manner as the cutting guides hereinbefore described, the differences being that the cutting guide 320 interconnects directly with the alignment rod and that various size cutting guides must be provided to accommodate various sized tibias.

Likewise, the cutting guide 320, shown in FIG. 17, operates in the same manner as the cutting guide devices hereinbefore described, but it does not include cutting guide clamps. The cutting guide 320 includes cutting slots 322, and it interconnects directly with alignment rod by means of aperture 328. The distance between facing members 330 can be adjusted by moving base members 332 and 334 with respect to each other to size the cutting guide 320 for the tibia to be cut. Upon proper sizing, the base members 332 and 334 may be locked with respect to each other by set screw 336 or any other means known in the art.

FIG. 18 shows an embodiment of the cutting guide for use when the patellar tendon, the patella, or the quad tendon interferes with the placement of the other cutting guides of the present invention. As shown in FIG. 18, the cutting guide 350 may be directly interconnected with the alignment rod, and positioned on the tibia as hereinbefore set forth. Basically, this embodiment of the invention includes only one cutting guide. The cutting guide 350 and the cutting guide slot 322 may be wider than in the previous embodiments to help stabilize the milling bit in operation. In this embodiment, the milling bit may be first plunged across the tibia, and then moved therealong. The milling bit may be spring loaded to increase resistance as it is plunged through the cutting guide to bias the bit against being plunged too far across the tibia to cause damage to the tissue about the tibia. Additionally, a support member, not shown, could be provided to extend from the cutting guide 350, over and across the tibia to the other side thereof where it could have a slot to capture the milling bit and provide additional support thereto. The reference numerals 338, 360 and 392 correspond to the reference numerals 238, 260 and 292 respectively.

As shown generally in FIGS. 19-23, the pattern apparatus of the present invention, generally indicated at 430, comprises pattern plates, generally indicated at 432, and crossbar apparatus, generally indicated at 440.

Pattern Plates

Pattern plates 432 include fixation apertures 434 extending therethrough for accepting fixation means, as will hereinafter be described, for affixing the pattern plates 432 to a bone. The pattern plates 432 further include a cutting path 436 for dictating the path along which a bone is to be cut. As shown in FIGS. 19-23, which are directed to an embodiment of the present invention for resecting a distal femur, the cutting path 436 in the pattern plates 432 matches the profile of a femoral component of a knee prosthesis for resecting the femur to accept the femoral component of the prosthesis. Importantly, as will hereinafter be described, the cutting path 436 could be identical in size and shape to an interior bearing surface of a femoral component of the knee prosthesis, or could vary in size and shape in accordance with alternative methods and apparatus used to perform the resection. For example, the cutting path could be larger than the desired resection, but a larger cutting tool could be used to arrive at a resection of the desired the desired size.

In the embodiment of the present invention shown in FIG. 21, the cutting path 436 includes an anterior end 436A, an anterior cut portion 436B, an anterior chamfer portion 436C, a distal cut portion 436D, a posterior chamfer portion 436E, a posterior cut portion 436F, and a posterior end 436G. Alternatively, the cutting path 436 could be of any desired shape in accordance with the prosthesis systems of the various manufacturers of such prosthesis, the desires of the surgeon utilizing the apparatus and/or the application for which a bone is to be cut.

Figure 19:
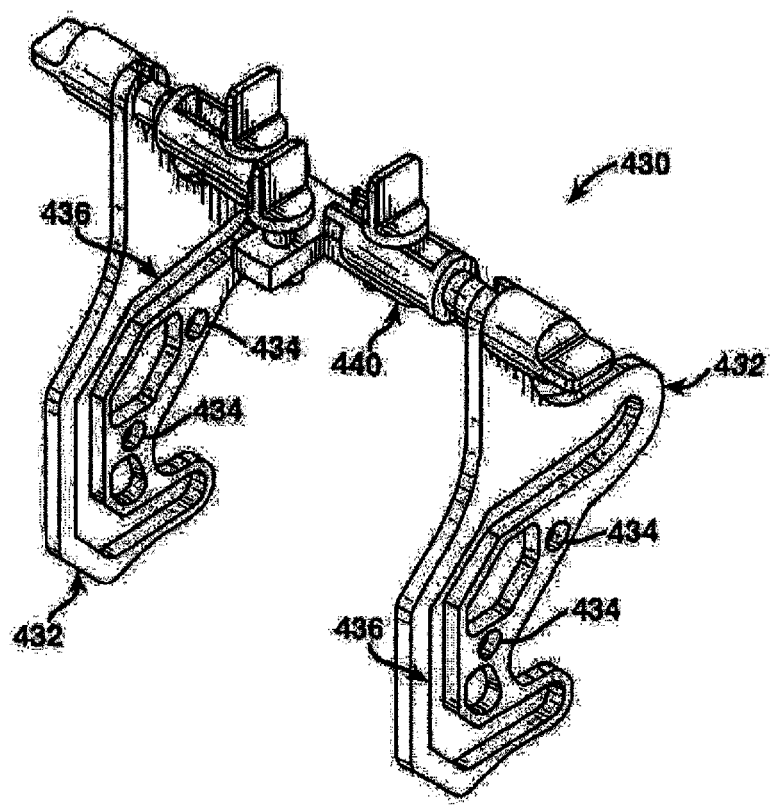
FIG. 19 is a rear perspective view of an embodiment of the pattern apparatus of the present invention.
Figure 20:
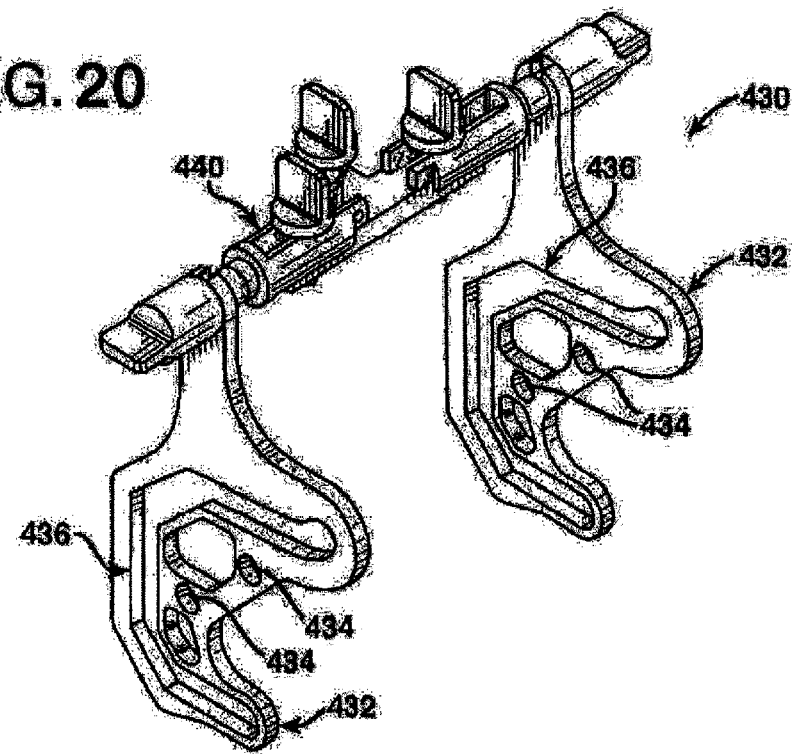
FIG. 20 is a front perspective view of the pattern apparatus shown in FIG. 19.
Figure 25:
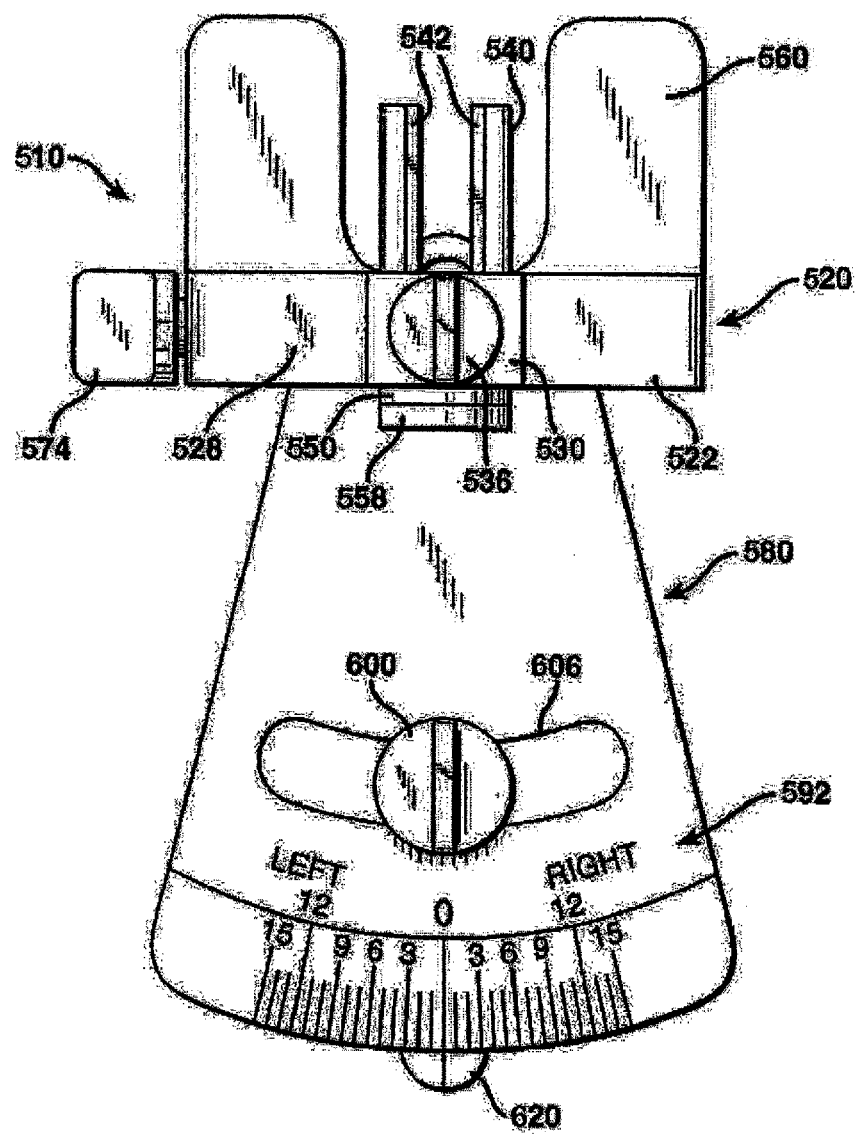
FIG. 25 is a top plan view of the positioning apparatus shown in FIG. 24.
Figure 26:
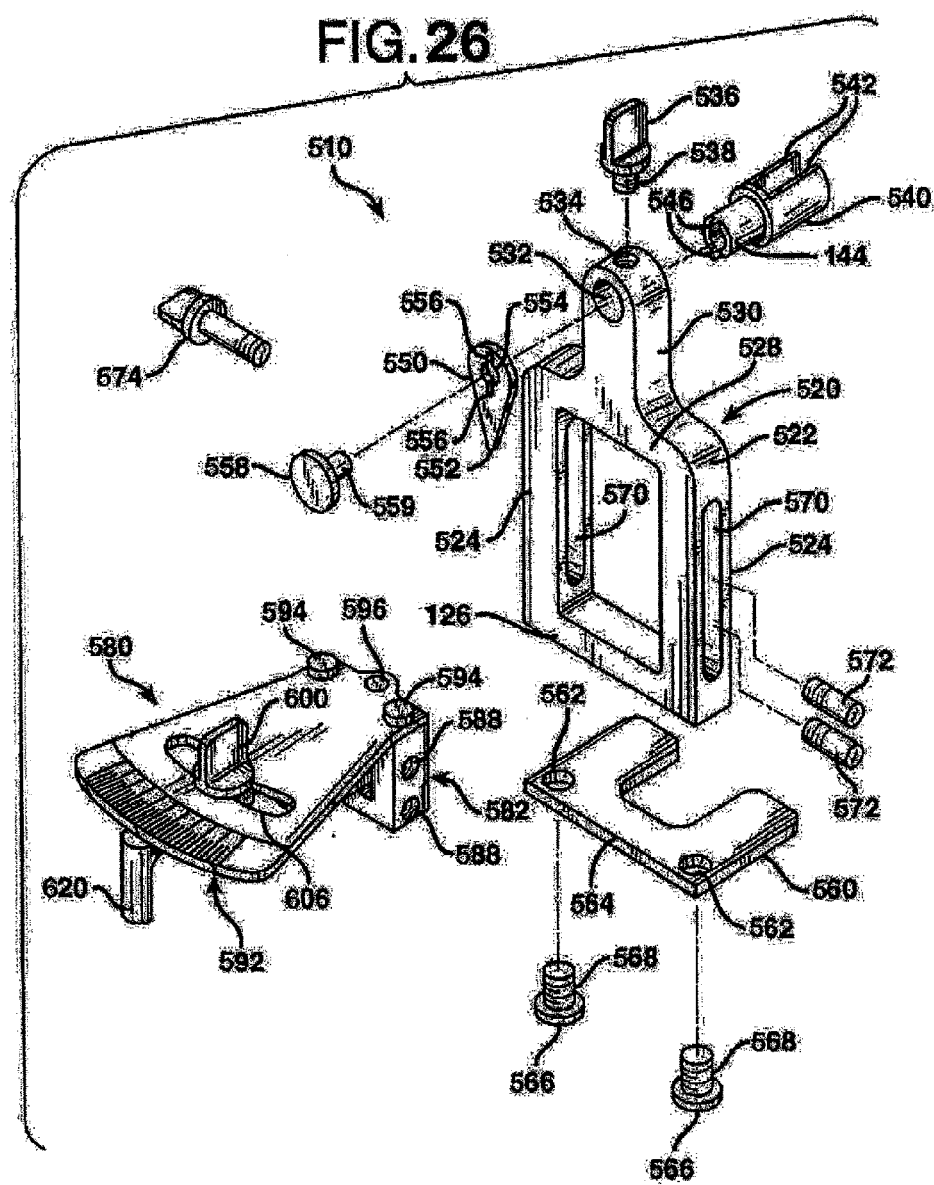
FIG. 26 is an exploded perspective view of the positioning apparatus shown in FIG. 24.
Figure 27:
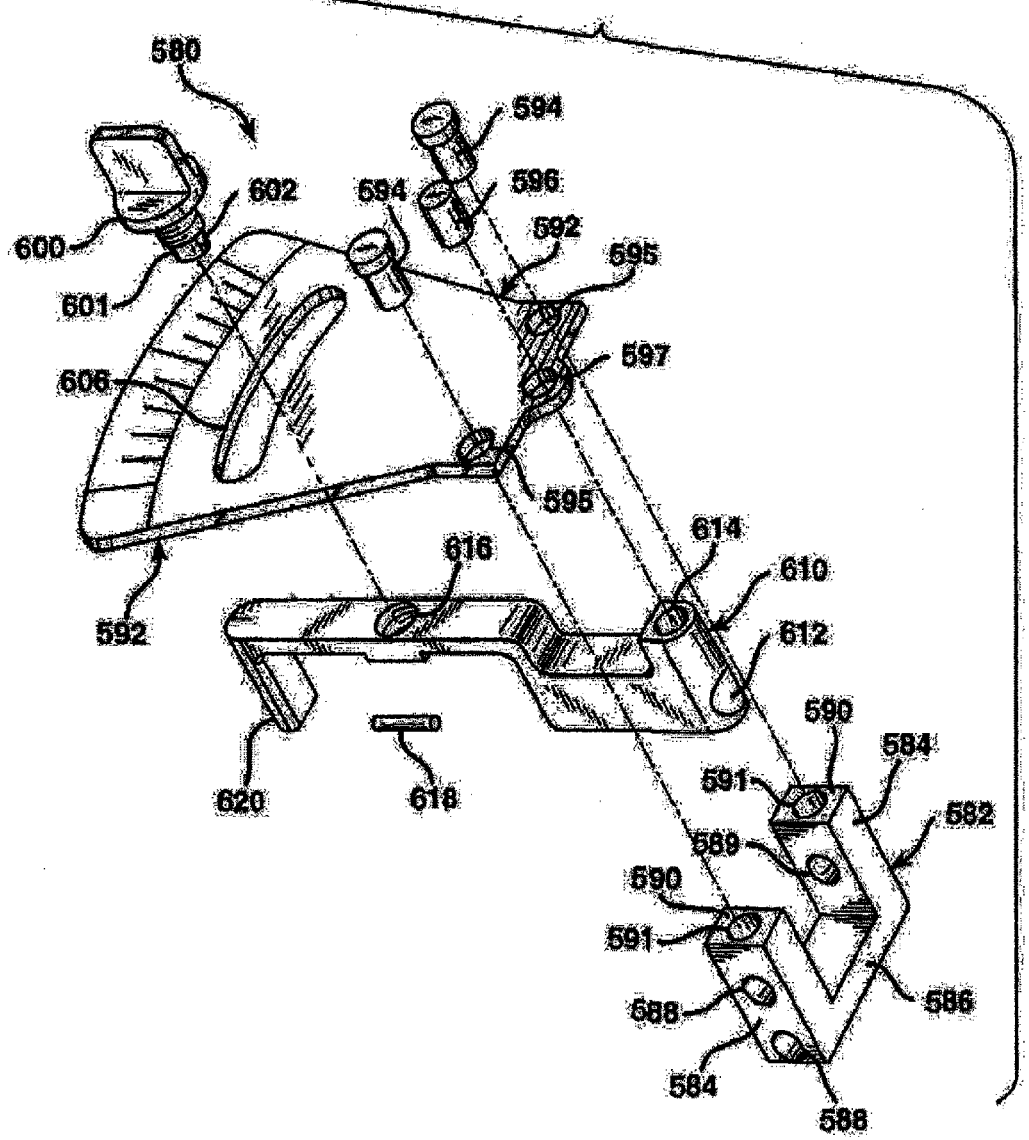
FIG. 27 is an exploded perspective view of the protractor rod guide assembly portion of the positioning apparatus shown in FIG. 24.
Figure 28A:
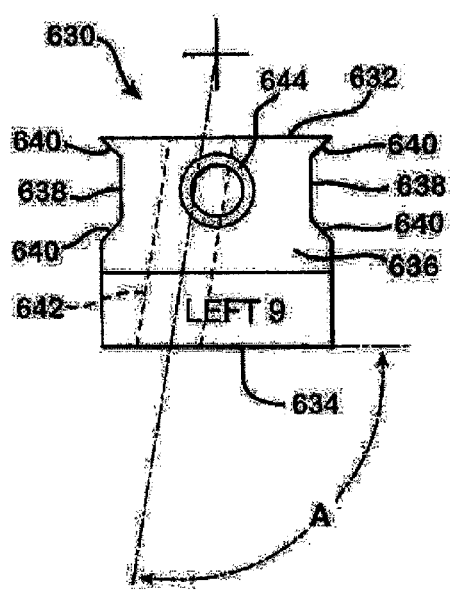
FIGS. 28A-28D are plan views of another embodiment of a rod guide assembly for use with the positioning apparatus shown in FIG. 24.
Figure 28B:
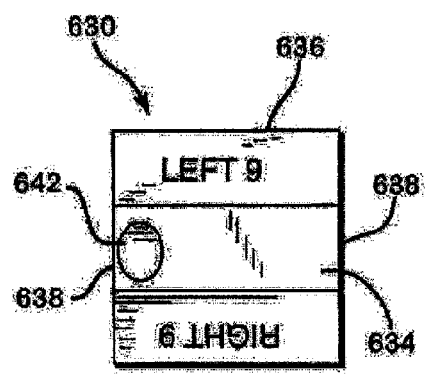
Figure 28C:
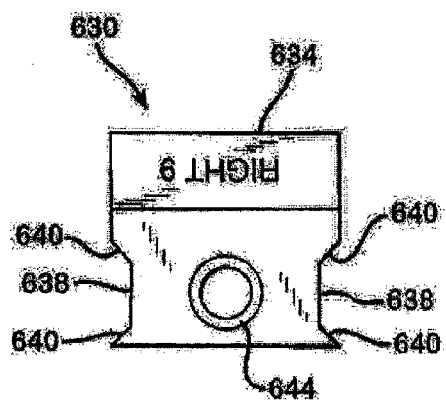
Figure 28D:
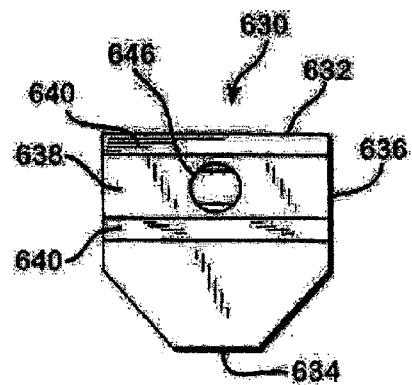

Although a single pattern plate 432 may be employed in resecting a femur or other bone (and in some cases, i.e., a partial femur resection, it may be preferable to employ a single pattern plate 432), two pattern plates 432 are generally employed to co-act with each other to support a cutting means on two sides of a bone to be cut. In the case of resecting a femur, a preferred embodiment of the present invention, as shown in FIGS. 19-21, comprises two pattern plates 432 positioned on opposing sides of a femur. The pattern plates 432 are interconnected with each other, and maintained in proper alignment with respect to each other by a crossbar apparatus generally indicated at 440, to straddle a bone. The pattern plates 432 include crossbar apertures 438 for interconnecting with the crossbar apparatus 440. The pattern plates may also include crossbar slots 439 for permitting quick connect/disconnect between the pattern plates 432 and the crossbar apparatus 440. Of course, it should be noted that the pattern plates 432 could interconnect with the crossbar in any other manner known in the art, or especially with bone cutting applications other than resecting the femur, the pattern plates 432 could be used without a crossbar.

Crossbar Apparatus

The crossbar apparatus 440 includes a number of component parts, namely, T-bar 442 having a top 444 and a stem 446 interconnected with and extending from the top 444 in the same plane. The T-bar 442, shown in the figures, comprises a flat metal member having a uniform rectangular cross-section through both the top 444 and the stem 446. Three threaded lock apertures 448 are formed through the T-bar 442, one at each end of the top 444 and at the far end of the stem 446. Lock screws 450, having gripable heads 452 and shafts 454 with threaded waists 456, threadably engage the threaded lock apertures 448 in the T-bar 442. The lock screws 450 further include pin holes 458 extending radially through the shafts 454 at the terminal ends thereof for receiving pins 459 for capturing the lock screws 450 on the T-bar 442.

The crossbar apparatus 440 further includes linkages 460 having a first end for interconnection with the T-bar 442 and a second end for supporting and engaging pattern plates 432. The first ends of the linkage 460 include a lower flat surface 462 for contacting the T-bar 442, overhanging shoulders 464 for contacting the sides of the T-bar 442, and an upper flat surface 466 for contact with the lock screws 450 for locking the linkages 460 onto the T-bar 442. As shown in detail in FIG. 23, the second ends of the linkage 460 include cylindrical supports 468 for supporting the pattern plates 432 thereon. The cylindrical supports 468 include axial extending apertures 469 for receiving capture pins 470 therethrough, the capture pins 470 including flanged ends 472 and threaded ends 474. The capture pins 470 serve to capture pattern lock nuts 476 on the linkages 460, the capture pins 470 extending through the axial apertures 469, the flanged ends 472 retaining the capture pins 470 therein, the threaded ends 474 extending out of the cylindrical supports 469 and into the threaded interior 477 of the pattern lock nuts 476. The cylindrical supports 468 receive the crossbar apertures 438 of the pattern plates 432 and the pattern lock nuts 476 are threaded down onto the capture pins 470 to secure the pattern plates 432 to the crossbar apparatus 440. Of course, other embodiments of the crossbar apparatus sufficient for supporting the pattern plates of the present invention are considered within the scope of the present invention.

Positioning Apparatus

As shown in FIGS. 24-28, the positioning apparatus of the present invention is generally indicated at 510. The positioning apparatus generally comprises positioning body 520 and alignment apparatus 580. The positioning body 520 comprises a frame 522 having sides 524, bottom 526 and top 528 arranged to form a frame having a rectangular aperture defined therewithin. The top 528 further includes a head 530 formed thereon having a linkage aperture 532 extending therethrough at an upper end thereof, and having a lock aperture 534 extending from the upper edge of the head to the linkage aperture 532. A lock screw 536 having a threaded shaft 538 extends into and is threadably engaged with the lock aperture 534 for locking the head 530 to a linkage, namely crossbar linkage 540. Crossbar linkage 540 includes a first end having an upper flat surface 542 for interconnecting with the crossbar in a manner similar to the pattern plate linkages for attaching the pattern plates to the crossbar as hereinbefore described. The crossbar linkage 540 further includes a shaft 544 which is received by the linkage aperture 532 in the head 530 to interconnect the positioning body 520 with the crossbar linkage 540 and hence with the crossbar apparatus 440 and the pattern apparatus 430. The positioning body can then be locked onto the crossbar linkage 540 by means of lock screw 536.

The end of shaft 544 of the crossbar linkage 540 includes projections 546 extending axially from the shaft 544. When the shaft 544 is positioned in the linkage aperture 532, the projections 546 extend beyond the frame 522 and are received in slots 556 in alignment indicator 550 for keying the orientation of the alignment indicator 550 with the alignment of the crossbar linkage 540, and hence with the alignment of the crossbar apparatus 440 and the pattern apparatus 430. The alignment indicator 550 includes an alignment arrow 552 for indicating alignment on a scale that may be set forth on the positioning body 520. An indicator pin 558 having a shaft 559 may be employed to pin the alignment indicator 550 to the crossbar linkage 540.

Attachable to the bottom 526 of the positioning body 520 is skid 560. The skid 560 includes skid apertures 562, one of which may include an aperture flat 564 for ensuring proper alignment and positioning of the skid 560 with respect to the positioning body 520. The skid 560 is attached to the bottom 526 of the positioning body 520 by means of skid bolts 566 having threaded shafts 568 which co-act with threaded apertures in the bottom 526 of the positioning body 520. Of course, the skids could be formed integrally as part of the positioning body.

The sides 524 of the positioning body 520 include slots 570 extending in a facing relationship along the sides 524. The slots extend from exterior surfaces of the sides to interior surfaces thereof, i.e., to the interior rectangular aperture formed within the positioning body 520.

Alignment Apparatus

The alignment apparatus 580 interconnects with the positioning body 520 by means of alignment guide body 582 which is a U-shaped member having sides 584 and a bottom 586. The alignment guide body 582 is sized to fit within the rectangular aperture formed within the positioning body 520. The alignment guide body 582 is retained within the positioning body by means of guide studs 572 that extend through the sides 524 of the positioning body 520 within the slots 570 and into guide apertures 588 at one side of the alignment guide body 582. At the other side of the alignment guide body 582 a lock stud 584 extends through the slot 570 in the side 524 of the positioning body 520 and into a threaded lock aperture 589 in the alignment guide body 582. The guide studs 572 and the lock stud 574 co-act to maintain the alignment guide body 582 within the positioning body 520, and the lock stud 574 can be threaded down to lock the vertical position of the alignment guide body 582 with respect to the positioning body 520.

At upper ends 590 of the sides 584 of the alignment guide body 582 are plate apertures 591. The alignment plate 592 includes bolt apertures 595 aligned with the plate apertures 591 of the alignment guide body 582, and plate bolts 594 extend through the bolt apertures 595 in the alignment plate 592 and into the plate apertures 591 to secure the alignment plate 592 to the alignment guide body 582. The alignment plate 592 further includes rod guide aperture 597 which receives rod guide bolt 596 therethrough to interconnect the alignment plate 592 with the IM rod guide 610 as will hereinafter be described. Additionally, the alignment plate 592 includes lock slot 606 extending through the alignment plate 592 along an arc for purposes hereinafter described.

The IM rod guide 610 includes IM rod aperture 612 for receiving an IM rod therethrough. The IM rod guide 610 is interconnected at a forward end with the alignment plate 592 by means of plate attachment aperture 614 on the rod guide 610 which receives rod guide bolt 596 therein, after such bolt 596 passes through the alignment plate 592 to secure the rod guide 610 in a pivoting relationship with respect the alignment plate 592 at forward ends of the rod guide 610 and the alignment plate 592. The IM rod guide 610 is additionally interconnected with the alignment plate 592 by rod guide lock bolt 600 which includes a threaded shaft 210 and pin aperture 602. The rod guide lock bolt 600 extends through the slot 606 in the alignment plate 592 and through threaded lock bolt aperture 616 in the rod guide 610 where it is captured by means of capture pin 618 extending through the pin aperture 602. The IM rod guide further includes rod guide handle 620 which is configured to be easily manipulated.

The alignment plate 592 further includes a printed angular rotation scale which indicates the degree of angular rotation between the rod guide 620 and the alignment apparatus, and hence, the angular rotation between the IM rod and the positioning body 520. After such alignment is determined, it can be locked into place by tightening down rod guide lock bolt 600. Thereafter, with such angular rotation fixed, the pattern apparatus 430 can be positioned with respect to the bone to cut, and the positioning apparatus 510 can be removed from interconnection with the IM rod and the pattern apparatus 430, the IM rod removed from the bone, and bone cutting can be initiated.

In another embodiment, as shown in FIGS. 28A, 28B, 28C and 28D, IM rod guide block 630 is used instead of the alignment plate 592 and the alignment guide body 582. The IM rod guide block 630 includes a rear surface 632, a front surface 634, a top surface 636 and sides 638. The sides 638 include retaining flanges 640 at the rear and front surfaces for retaining the IM rod guide block 630 within the rectangular aperture formed by the positioning body 520. The IM rod guide block 630 further includes IM rod aperture 642 extending through the block 630 from the rear surface 632 to the front surface 634 for accepting the IM rod therethrough. The rod aperture 642 extends through the guide block 630 at an angle A with respect to axis of the guide block for accommodating the varus/valgus orientation of the femur. The guide block 630 is part of a set of blocks having rod apertures of various angles extending therethrough, i.e., 5, 7, 9, 11, 13 degrees, for use with femurs having varying angles of orientation. The guide block 630 also includes lock aperture 646 for locking the proper vertical position of the guide block 630 with respect to the positioning body 620. The guide block 630 may additionally include two apertures 644 for accepting an anterior referencing arm for use in determining the anterior/posterior size of the femur. It should be noted that other alignment means for aligning the positioning apparatus with respect to a bone to be cut are considered within the scope of the present invention.

Fixation Means

Figure 29:
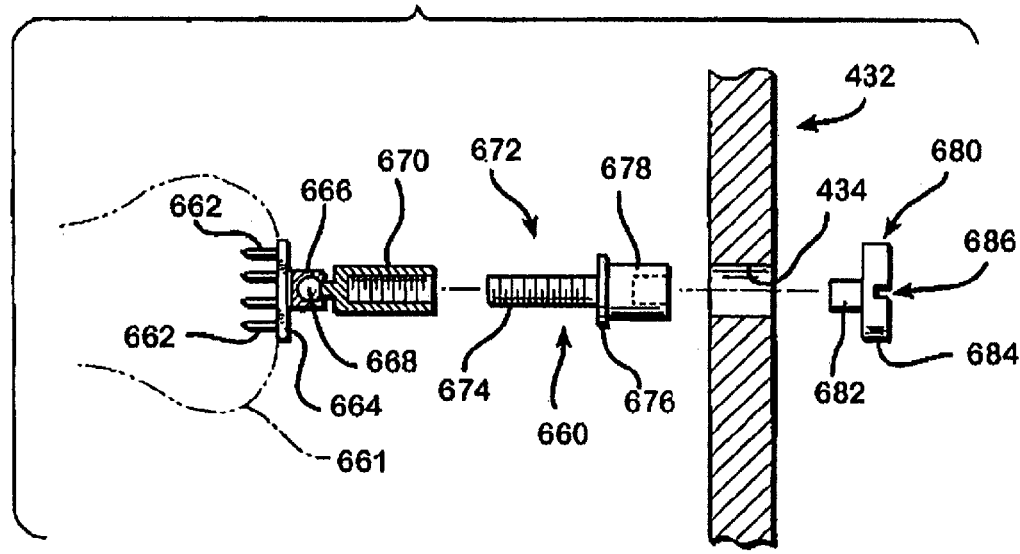
FIG. 29 is a side plan view of an embodiment of the fixation device for affixing the pattern apparatus shown in FIG. 19 to a bone.

Various fixation means, including those known in the art, can be used to fix the pattern plate or plates to the femur or other bone to be cut. FIG. 29 shows a preferred fixation means, generally indicated at 660. The fixation means 660 includes a spike plate 664 carrying on one side thereof a spike or spikes 662 for contacting, and even extending into, bone 661. At the other side of the spike plate 664 is spike plate socket 666 for receiving plate driving ball 668 in a keyed relationship therewith. The driving ball 668 is interconnected to an end of driving sleeve 670 and which has a threaded aperture extending therein from the opposite end thereof.

A driving screw 672 having a threaded shaft 674 co-acts with the internally threaded driving sleeve 670 such that the rotation of the driving screw 672 either propels or retracts the driving sleeve 670, as well as the spike or spikes 662, with respect to the driving screw 672. The driving screw 672 further includes a captured head 678 and capture flange 676. The captured head 678 is received within a fixation aperture 434 in the pattern plate 432, the capture flange 676 preventing the captured head 678 from passing through the fixation aperture 434. A driving cap 680 is interconnected with the captured head 678 at the outside of the pattern plate 432. The driving cap 680 includes a shaft 682 received by the captured head 678, a flanged head 684 for contacting against the outside of the pattern plate 432, and a driver recess 686 of any desirable configuration for receiving driving means such as a flat, phillips or hex head driving means for driving the driving cap 680 to drive the driving screw 672 to move the spike or spikes 662 towards or away from a bone.

Importantly, this type of fixation means allows for fixation of the pattern plates 432 to even osteoporotic bones. Additionally, this fixation means is self-adjusting to fit changing contours of bones. Further, because of its relatively low profile, this fixation means does not interfere with soft tissue about a bone to be cut. Other types of fixation means include cannulated screws, pins, spring loaded screws, captured screws, spiked screws and/or combinations thereof, all of which are considered within the scope of the present invention and could be used in connection with the present invention.

Anterior/Posterior Referencing

Figure 30:
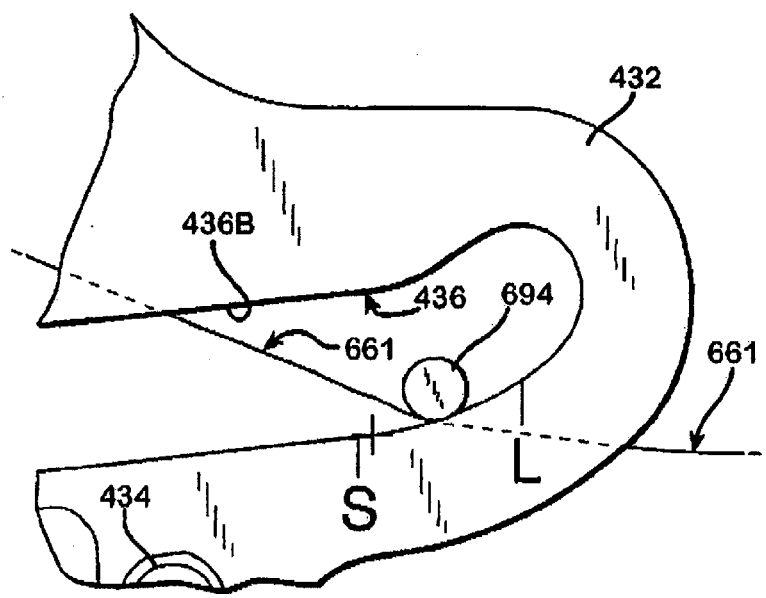
FIG. 30 is a partial side plan view of the pattern apparatus shown in FIG. 19, showing the posterior/anterior referencing guide.

The apparatus of the present invention further includes built-in anterior/posterior referencing means as shown in FIG. 30 for use in connection with preparation of the distal femur in total knee replacement. As is known in the art, anterior/posterior referencing refers to proper positioning of the distal femur cuts with respect to the anterior and/or posterior sides of the femur or other bone to be cut.

The anterior/posterior difference between femoral implant sizes may vary by as much as 3 to 5 millimeters between sizes. Of course, many femurs are between sizes. Disregarding proper positioning of the cutting guide and the associated femur cuts could lead to flexion contracture (where the bone is slightly below size and the implant adds too much material to posterior side of femur which results in the inability to move the knee into flexion because the extra posterior material contacts the tibial implant components) and/or anterior notching of the femur (where the bone is slightly above size and the anterior runout point of the anterior cut is recessed in the anterior side of the bone in a sharp notch, thus seriously weakening the structural integrity of the distal femur, especially under cyclic fatigue or impact loading conditions).

Anterior referencing systems have a major advantage over posterior referencing systems in that they theoretically never notch the anterior cortex of the femur. The drawback of anterior referencing is that a slightly larger bone results in collateral ligament laxity in flexion and a slightly smaller bone will result in collateral ligament tightening in flexion (flexion contracture).

Posterior referencing systems have a major advantage over anterior referencing systems in that they theoretically never develop flexion contracture. The drawback is that a slightly large femur is prone to anterior notching, which can increase the likelihood of distal femoral fractures under either impact loading or cyclic fatigue loading.

Another approach to anterior/posterior referencing is a hybrid design that allows for both anterior and posterior referencing. The positioning apparatus 510 references the posterior femoral condyles (posterior referencing), while the pattern plates 432 allow for precise referencing of the anterior femoral cortex. The anterior referencing device can be as simple as that shown in FIG. 30, wherein a referencing pin 694 is placed through the anterior-most cutting paths 436 of the pattern plates 432 to contact the anterior femoral cortex 661. The pattern plates 432 include markings S (smaller size) and L (larger size). When the pin 694 falls between the S and L marks, the pattern plates 432 are the proper size and are properly positioned for that femur. If the pin 694 falls outside the range marked by S and L towards the S side, a smaller size pattern plate should be used, and conversely, if the pin 694 falls outside the range on the L side, a larger size pattern plate should be used. Alternatively, the pattern plate 432 could be adjusted vertically via means not shown to compensate for between-size bones.

In another embodiment, the pattern plate could include a plunger assembly at the anterior end of the cutting path. The plunger could be movable vertically to contact the femur and indicate size of the femur with respect to the pattern plate in use. As such, the plunger could be incrementally marked from +4 to −4 millimeters with 0 being the proper size for the pattern plates in use. Again, the pattern plates could be sized up or down if the femur is off of the scale, or the pattern plates could be moved up or down to compensate for between size bones depending upon surgeon preference. If, for example, a bone registers a +2, anterior notching of the femur would occur. To avoid this, the pattern plates could be moved anteriorally 1 millimeter to +1. In this manner, anterior notching would be minimized and the posterior femoral condyles would only lack 1 millimeter of material, which should not be detrimental as some ligamentous laxity in flexion is acceptable because the collateral ligaments are normally slightly looser in flexion than they are in extension. It should be noted that the radii or curve in the anterior-most area of the cutting path will assure that anterior notching is easily avoidable.

Pattern Plate with Tracking Means

Figure 31:
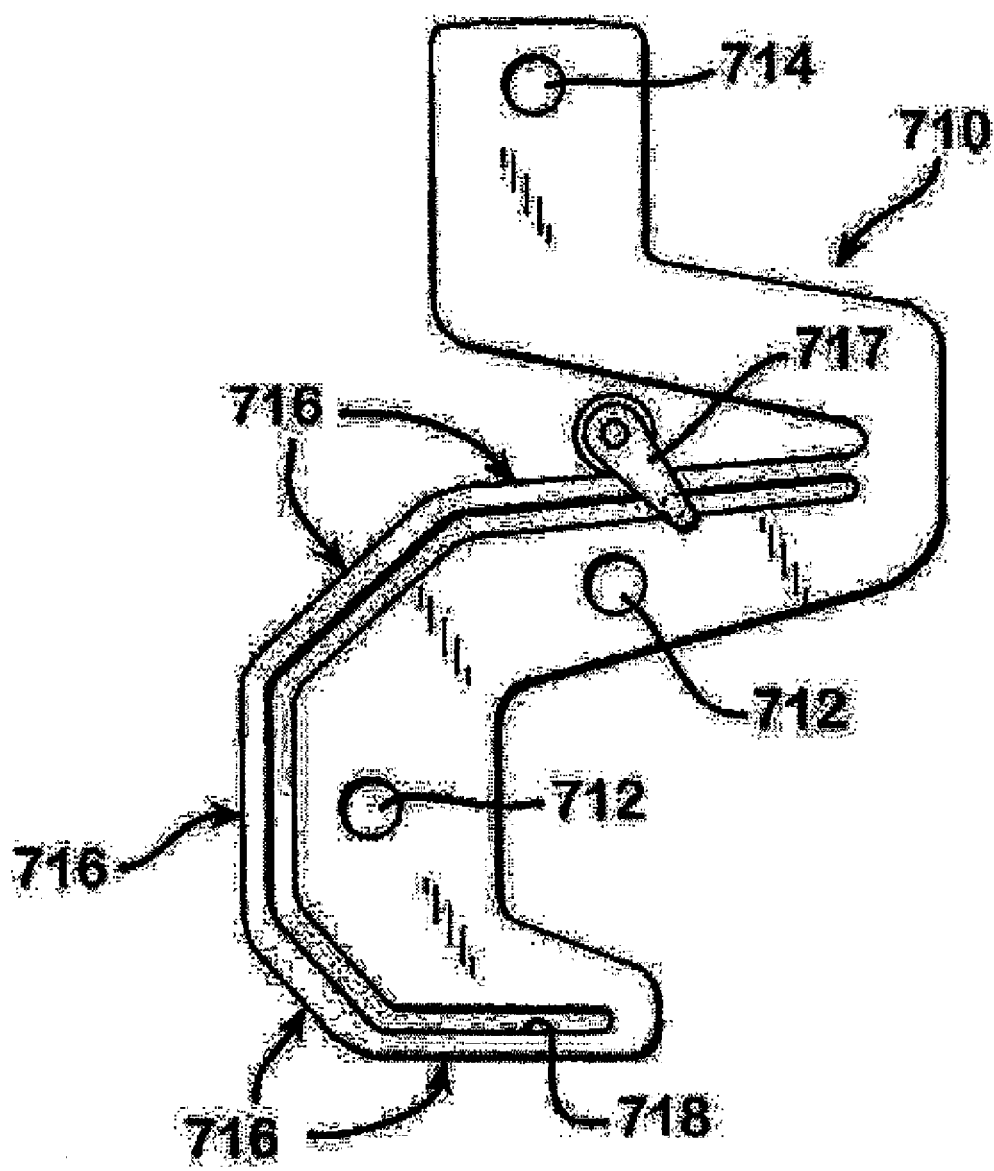
FIG. 31 is a side plan view of another embodiment of the pattern apparatus shown in FIG. 19.

Another embodiment of the pattern plates of the present invention is shown in FIG. 31. In this embodiment, the pattern plates, generally indicated at 710, basically comprise only the lower edge, or bearing surface 716 of the cutting path 436 of pattern plates 432 shown in FIGS. 19-21. Accordingly, the pattern plate 710 includes fixation apertures 712 and crossbar aperture 714. The milling apparatus bears against the bearing surface and follows the same therealong to resect the bone in accordance with the shape of the bearing surface 716. Of course, the bearing surface could be smaller or larger than the desired cut location depending on the size of the milling apparatus. The pattern plate 710 could further include a groove or guide means 718 extending in the pattern plate alongside the bearing surface and the milling apparatus could include an arm or other retaining linkage 717 extending from the handle or bushing of the milling apparatus and into the groove 718 for engagement with the groove 718 for guiding or retaining the milling apparatus along the bearing surface 716 of the pattern plate 710. Alternatively, it should be noted that the bearing surface could also comprise just the upper surface of the cutting path 436 of the pattern plates 432, as shown in FIGS. 19-21.

Ligament Balancing

Figure 32:
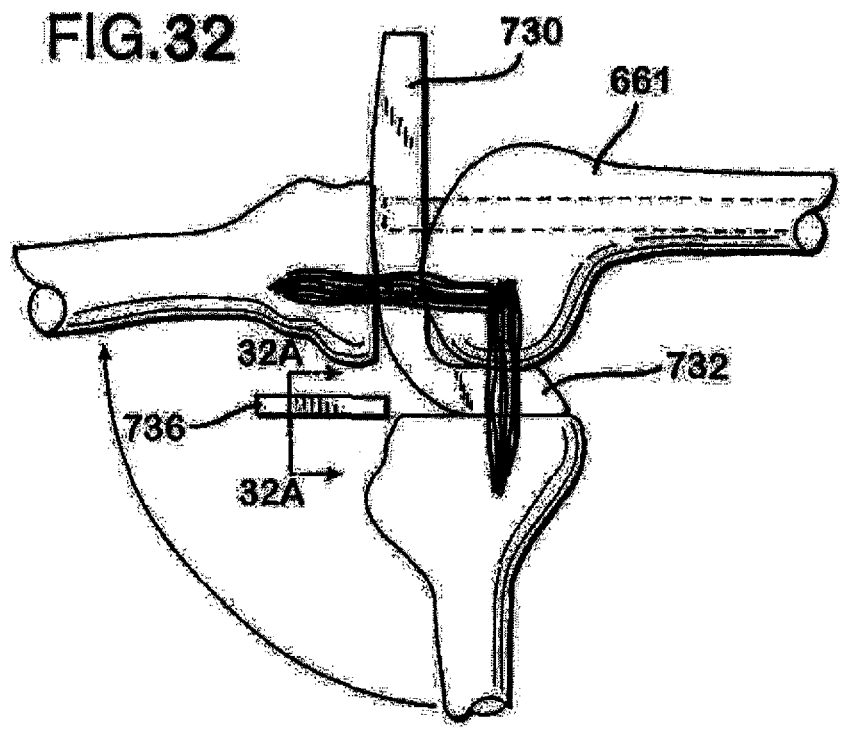
FIG. 32 is a side plan view of another embodiment of the positioning apparatus shown in FIG. 24 for use in performing ligament balancing.
Figure 32A:
FIGS. 32A and 32B are cross-sectional views along section A-A in FIG. 32.
Figure 32B:
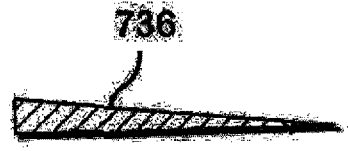

As shown in FIG. 32, an alternative embodiment of the alignment guide body 730 can be used for performing ligament balancing. The alignment guide body 730 of this embodiment can include a skid 732 formed as a part of the guide body 730, or attachable thereto. The skid 732 is of a relatively thick cross-section, approaching or equal to the cross-section of the guide body 730. The guide body 730 is attached to the femur 661 and the femur may be moved from extension to flexion and back, while the ligament tension of the collateral ligaments is reviewed. Ligamentous release can be performed to balance the ligaments. Further, shims 736, in either a rectangular cross-section (FIG. 32A) or an angled cross-section (FIG. 32B), can be used in connection with the alignment guide body 830 and skid 732. These shims could be positioned between the underside of the skid 732 and the resected tibia.

Milling Means

In a preferred embodiment of the invention, a cylindrical milling bit is used for following the cutting path described in the pattern plates for resecting a bone. Importantly, it is within the scope of the present invention to use a flat reciprocating bit, much like a hacksaw, for following the cutting paths described in the pattern plates for resecting a bone.

Further, it may be desirable to make all or some of the cuts using a cylindrical milling bit or a flat reciprocating bit having a smooth center section without cutting means. An advantage of a cutting tool without cutting means along a center portion thereof is the protection of posterior cruciate ligament during resection of the femur. Accordingly, one cutting tool could be used to make the anterior cut, the anterior chamfer, the distal cut and the posterior chamfer, while another cutting tool, with a smooth center portion, could be used to make the posterior cut to avoid any chance of jeopardizing the posterior cruciate ligament.

Additionally, the milling bits herein described can be used with or without a guide handle as will hereinafter be described. Further, it should be pointed out that it is within the scope of the present invention to fabricate the milling bit or other cutting tool from metal as heretofore known, or to alternatively fabricate the milling bit or other cutting tool from a ceramic material. An advantage of a ceramic milling bit or cutting tool is that such resists wear and, accordingly would be a non-disposable component of the present invention which would help to reduce the cost of the system of the present invention.

Three Dimensional Shaping

Figure 33A:
FIGS. 33A and B are front plan views of an embodiment of the cutting apparatus of the present invention for cutting a bone a in curvilinear cross-sectional plane.

Initially, it should be noted that the term cutting profile the profile geometry of a mediolateral section taken normal to the cutting path through the bony surfaces created by cutting the bone. As shown in FIG. 33, in an alternate embodiment of the present invention, a milling apparatus having a three-dimensional profile, or a form cutter, can be used to shape a bone in three-dimensions. The curved profile milling bit 750, like the milling bits used in the previous embodiments of the present invention, includes cutting teeth 752 along the length thereof and spindles 754 at the ends thereof. This milling bit 730 can follow a pattern described by pattern plates and can be guided with a handle as will be hereinafter described.

Figure 35:
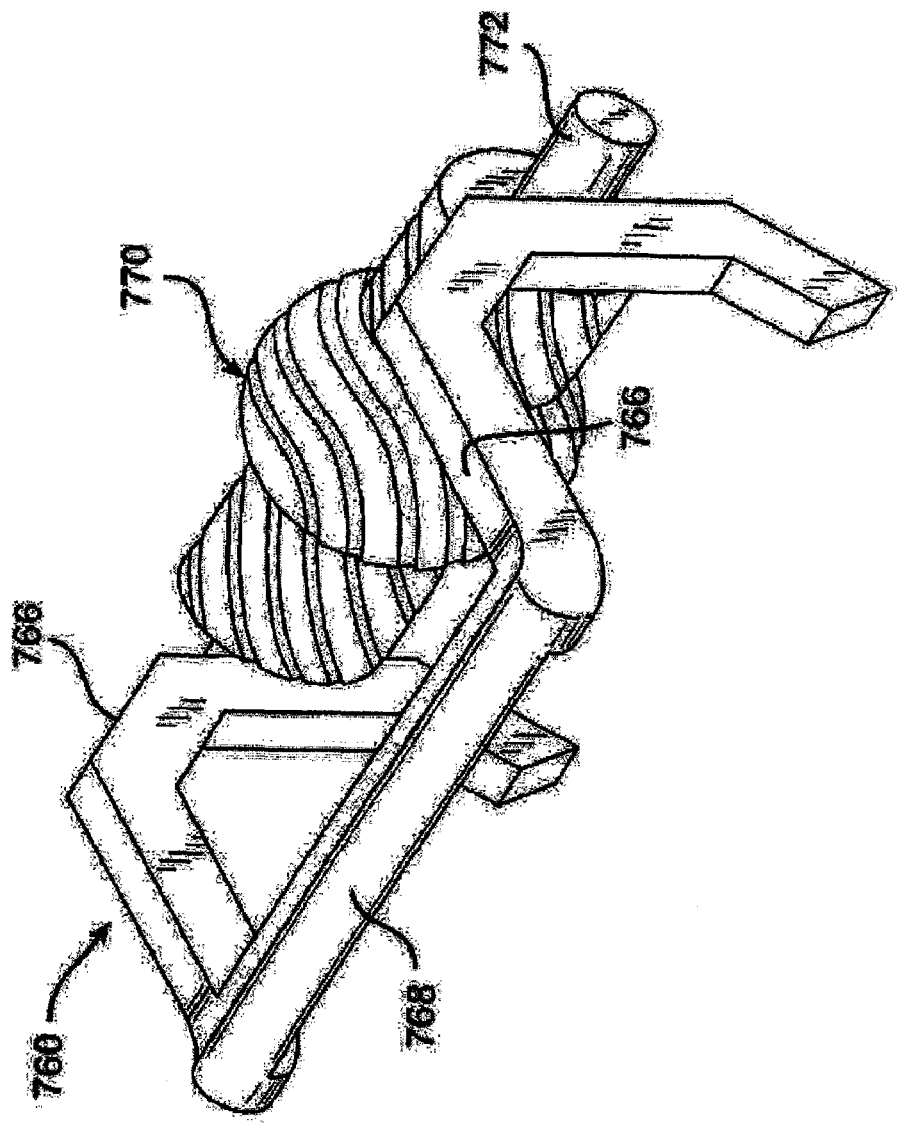
FIG. 35 is a perspective view of another embodiment of the pattern apparatus shown in FIG. 19, having a milling bit engaged therewith.

Importantly, by using a milling bit having a curved profile, one can cut a femur to resemble the natural shape of the femur, i.e., the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof, as shown in FIG. 33, or alternatively, could have one or more bulges discretely formed along the length thereof as shown in FIG. 35.

Guide Handle

Figure 34:
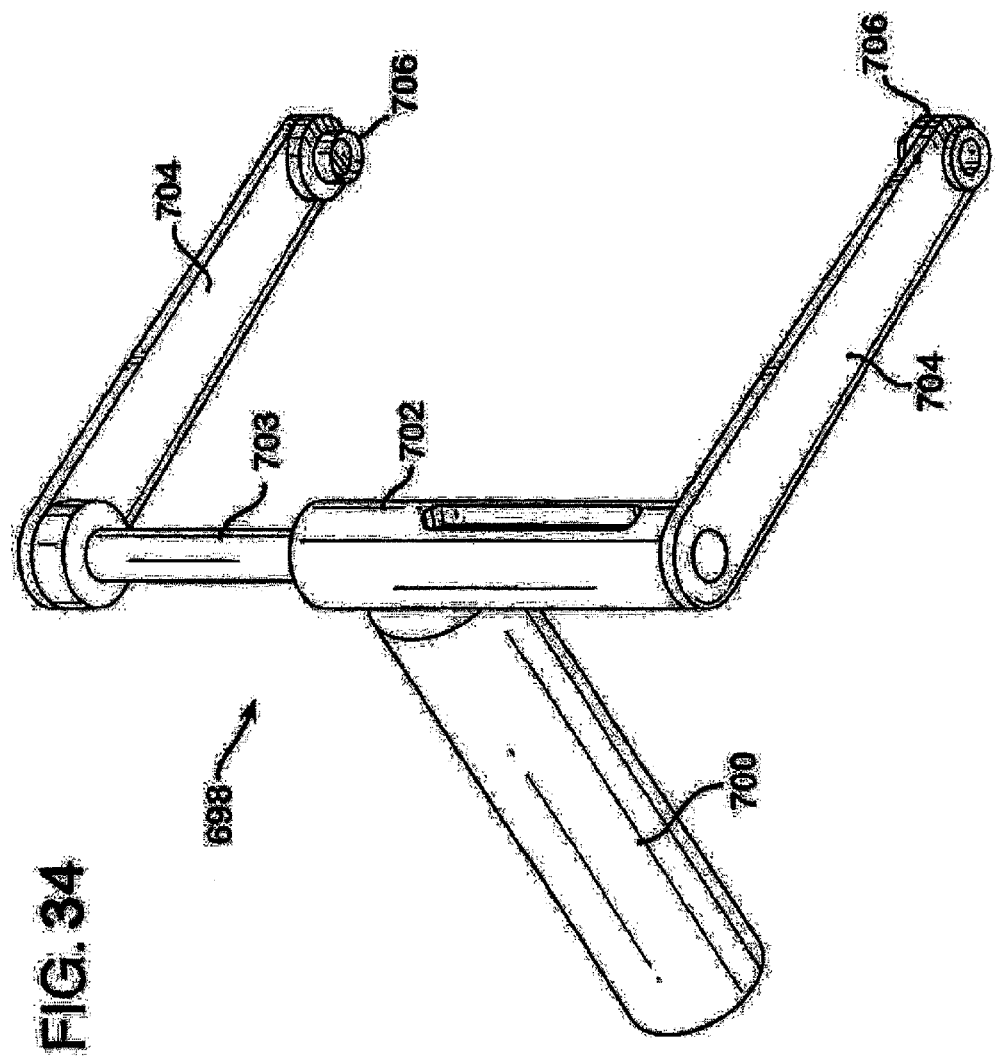
FIG. 34 is a perspective view of a handle for guiding a milling bit along a cutting path.

As shown in FIG. 34, a guide handle, generally indicated at 698 may be used to guide the milling bit along the cutting path of the pattern plate. The guide handle 698 comprises a grip portion 700 which is grasped by the user for manipulating the guide handle 698 and accordingly, the milling bit. The grip portion 700 is interconnected with a crossbar member 702 which includes a extension member 703 telescopically interconnected therewith. The crossbar member 702 and the extension member 703 may be positioned perpendicular with respect to grip portion 700. The extension member 703 is telescopically movable in and out of crossbar member 702. Means may be provided for locking the relative position of the extension with respect to the crossbar. Also, it should be noted that the grip portion may rigidly or pivotally be interconnected with the crossbar as desired.

Extending from outer ends of the crossbar 702 and the extension member 703 are sidebars 704 in facing and parallel relationship. The sidebars 704 have two ends, the first of which are interconnected with the crossbar and the extension member, and the second of which are configured to receive and capture spindles or bushings of a milling bit in spindle bushings 706. The spindle bushings are positioned in a facing relation and could include captured bushings. The captured bushings receive the spindles of a milling bit. The captured bushings are sized to be received by the cutting path in the pattern plates and co-act therewith to guide a milling bit therealong. Accordingly, after the pattern plate or plates are attached to a bone, the milling bit is placed into the cutting path. Next a milling handle 698 is positioned such the spindle bushings are aligned with the spindles of the milling bit. Next, the extension is actuated to retract into the crossbar to move the spindle bushings onto the spindles of the milling bit where they are captured. Next, the spindle bushings are positioned within the cutting path of a pattern plate or plates. If necessary, the extension and crossbar can be locked down to lock the entire apparatus. Next, the milling bit is actuated and the grip portion of the handle is grasped and manipulated to move the milling bit along the cutting path to cut a bone.

Distally Positioned Pattern Plate

Figure 36:
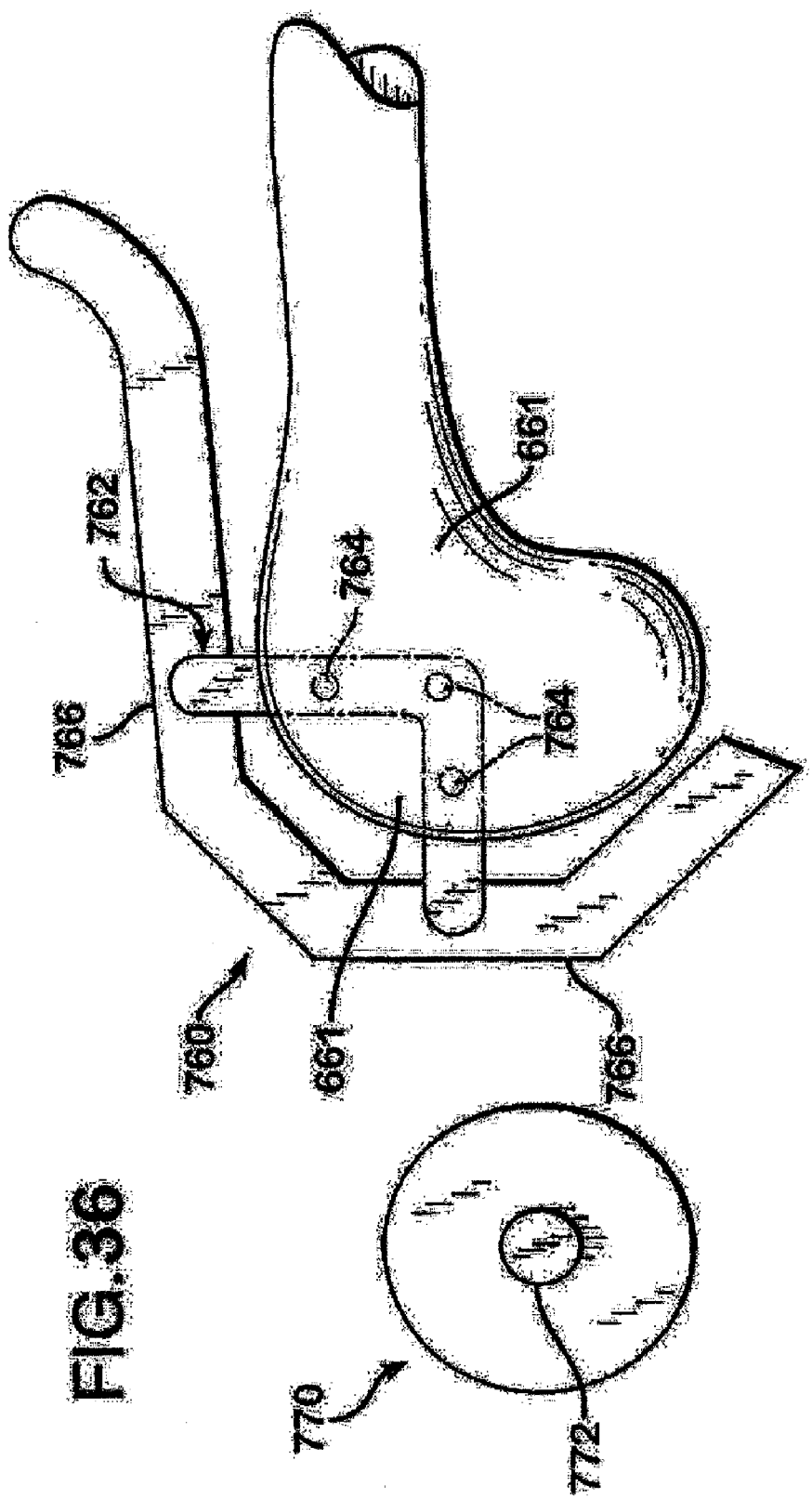
FIG. 36 is a side plan view of the pattern apparatus shown in FIG. 35 with the milling bit disengaged from the pattern apparatus.
Figure 37:
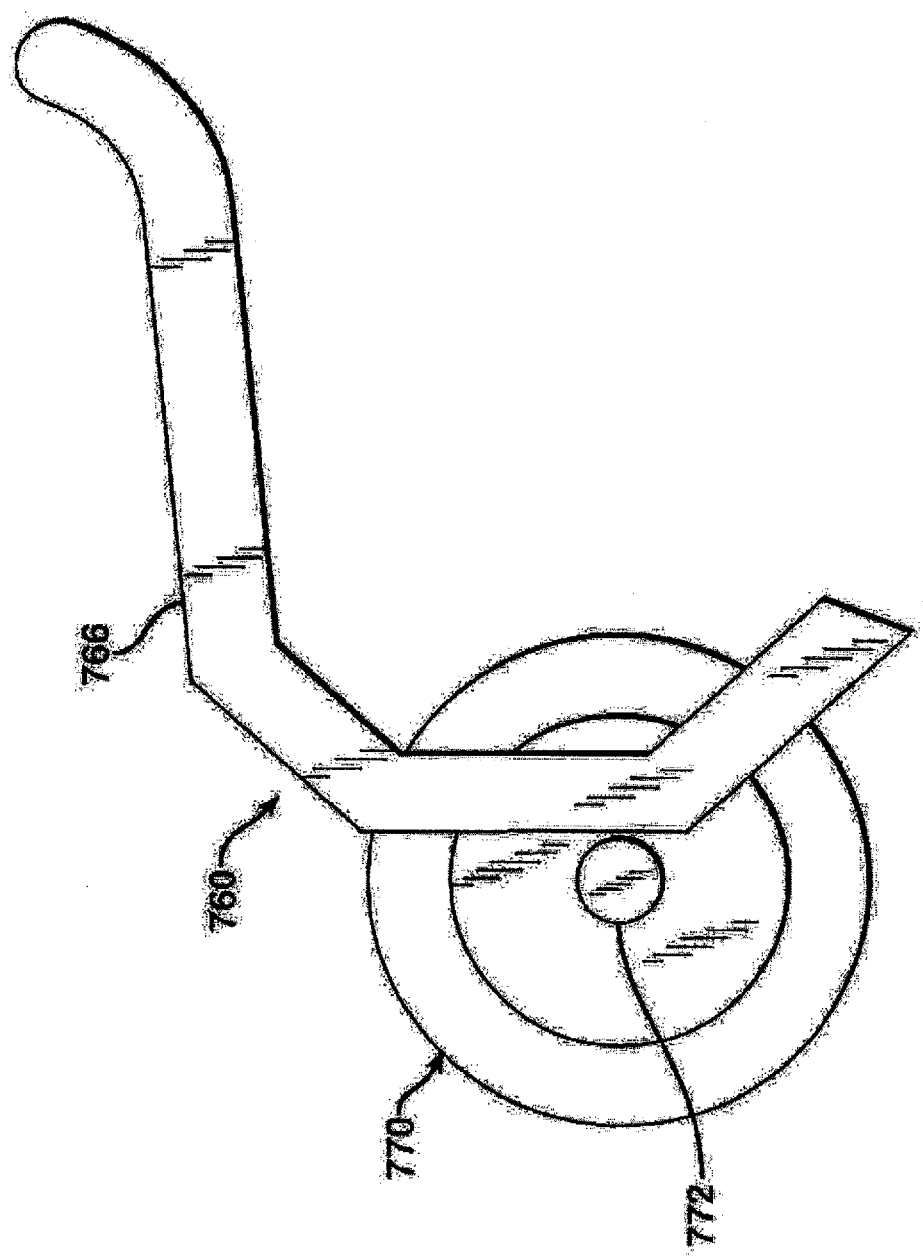
FIG. 37 is another side plan view of the pattern apparatus shown in FIG. 36 showing the milling bit engaged with the pattern apparatus.

As shown in FIGS. 35-37, in an alternate embodiment of the present invention for resecting a femur, the plates could take the form of a rail assembly, generally indicated at 760, positioned distally of the distal femur 661. The plates could be affixed to the femur by fixation arms 762, attached at one or more points to the rail assembly 760, and including fixation apertures 764 for receiving fixation screws or other fixation means for attaching the fixation arms 762, and hence the rail assembly 760, to a distal femur 661. The rail assembly 760 includes one or more guide rails 766 which match the shape of the desired resection, though the rails may be larger or smaller depending on the dimensions of the milling apparatus used and the positioning of the assembly 760 with respect to the femur. In the case that the assembly 760 includes two guide rails 766, as shown, an end rail 768 may be used to interconnect such guide rails 766. The end rail 768 could be replaced by a connection means similar to the crossbar apparatus 440, hereinbefore described. The rail assembly may be positioned on the distal femur in accordance with the teachings contained herein, or in any other manner known in the art. After alignment, according to any means disclosed herein or known or developed, and after fixation of the assembly to a femur, a milling bit 770 may be used to follow the guide rails 766 to resect the femur 661, the guide spindles 772, or bushings (not shown), of the milling bit 770, contacting and riding the guide rails 766. Importantly, the rail assembly 760 is attached to a femur and used in much the same way as the pattern plates previously described with the exception that the rail assembly can be positioned substantially distal of the femur, thereby potentially requiring less exposure and possibly resulting in less interference for placement thereof. The rail assembly 760 could further include an upper retaining rail for forming a slot or cutting path for capturing the milling bit therein. Additionally, it should be noted that any milling bit described herein could be used with rail assembly 760 including a curved profile milling bit.

Curvilinear Implants

Figure 38:
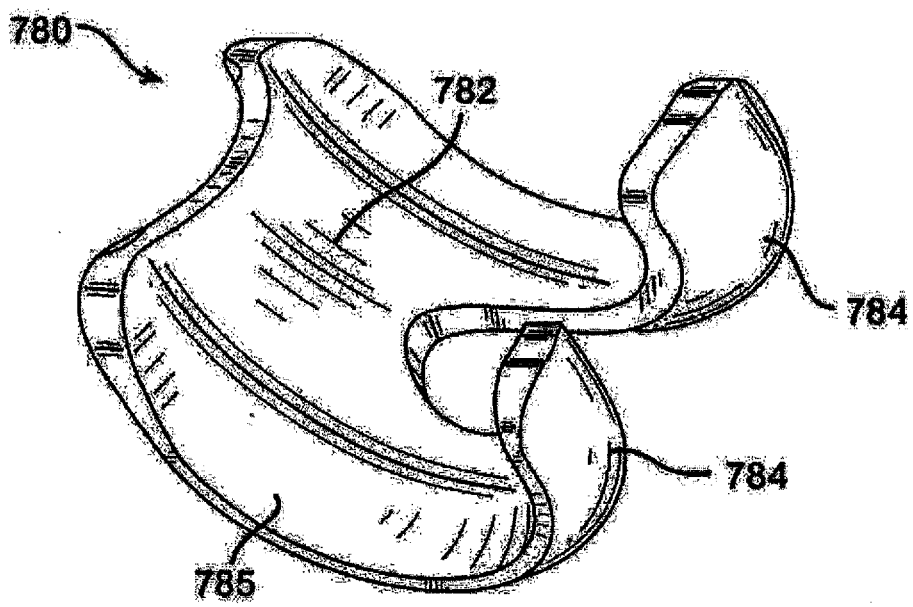
FIG. 38 is a perspective view of a femoral implant having a curved implant bearing surface.
Figure 39:
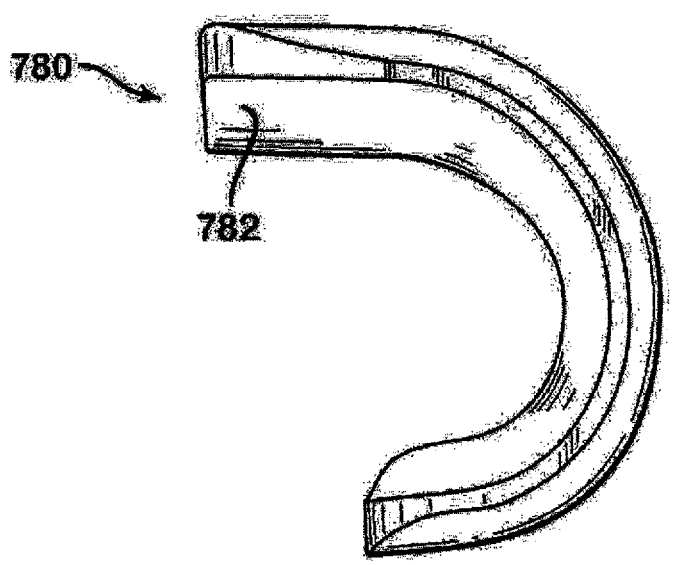
FIG. 39 is a side plan view of the femoral implant shown in FIG. 38.

As shown in FIGS. 38 and 39, an implant 780 may have curvilinear interior surfaces 782, as well as a more conventional curvilinear exterior surface. The particular example cited herein is a femoral implant used in total knee arthroplasty but the principles described herein may be applied to any application where foreign or indigenous material is affixed to an anatomic feature. The curvilinear bone surfaces necessary for proper fixation of such an implant may be generated through the use of the curvilinear milling or form cutter and the curvilinear cutting path means discussed herein. While it is possible to use multiple form cutters with differing geometries and, therefore, an implant with an internal geometry that varies along the cutting path from the anterior to the posterior of a femur, for the sake of intraoperative time savings a single form cutter is preferable.

The mediolateral cross-sectional internal geometry of such an implant, and therefore the necessary resected bony surfaces of the femur, are consistent about the cutting path in a single form cutter system. It should be noted that the implant may possess a notch between members 784 (posterior femoral implant condyles) in the areas approximately in between the distal and posterior femoral condylar areas to accommodate the posterior cruciate ligament and other factors. Because of the notch between the posterior femoral condyles it may not be necessary for the form cutter to cut any material in the notch. It may be desirable to provide outer flat surfaces 785 with an adjoining curvilinear surface 782 positioned therebetween. Other combinations of flat or curvilinear surfaces are also within the scope of the present invention.

Figure 47:
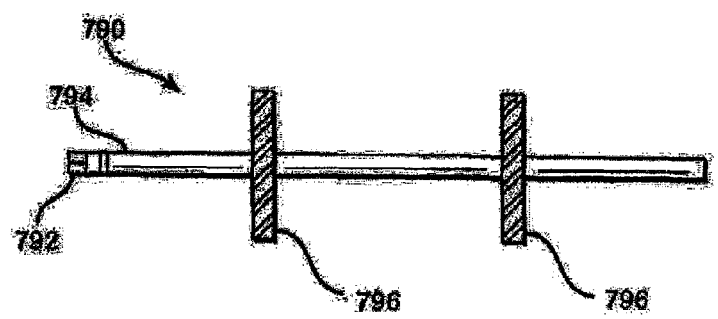
FIG. 47 is front plan view of another cutting apparatus for use in connection with the present invention.

Additionally, it may be advantageous to utilize a secondary form cutter as shown in FIG. 47 for use in creating a slot or slots in or near the distal area of the femur after it has been resected. Such a secondary cutter 790 would include engagement means 792 for engagement with driving means, and a shaft 794 carrying cutters 796 for cutting slots into the femur through one or more of the resected surfaces thereof. Through the inclusion of an additional or adjunct cutting path in the pattern means, it would be advantageous to utilize the form cutter to create the aforementioned slots to accommodate the fixation fins which may be molded as an integral part of the interior surface of the implant. These fins would provide mediolateral fixation stability in addition to that provided by the trochlear groove geometry of the implant. Further, the fins also provide for additional surface area for bony contact and ingrowth to increase implant fixation both in cemented and cementless total knee arthroplasty.

There are numerous advantages to the femoral component herein described. Foremost, it will allow for the thinnest implant cross-section possible (perhaps 3 mm to 6 mm in thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e., when a cast is placed on a person's arm the muscles in that arm gradually weaken for lack of use.

Additionally, the curvilinear implant design may allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant will not only allow for the superior surface properties of ceramic, but also avoid the excessively thick cross-sections currently required for the use of the material.

This could result in a less expensive femoral implant because of the reduced amount of material needed for the implant, as well as an improved, more natural, and even stronger knee replacement. It may be desirable to vary the cross-section of the implant 780 to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces. Also, it should be pointed out the such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Patella Shaping

The apparatus for preparing a patella, as shown in FIGS. 40-42, comprises a plier-like patella resection apparatus generally indicated at 800. The patella resection apparatus 800 includes grip handles 802 for manipulating the apparatus, cross-over members 804 pivotally interconnected with each other by pin 806, and patella clamp members 808 extending from the cross-over members in parallel and facing relation. The patella clamp members 808 have beveled edges 810 for contacting and supporting a patella along the outer edges thereof. Guide member structures 812 are mounted on each of the patella clamp members 808 to form a retainer for a cutting means to follow a cutting path defined by the upper surface of the clamp members. Bushings 814 are captured within the retainer and the cutting path for receiving a cutting means 816 and guiding the cutting means 816 along the cutting path.

In preparing the patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

Bone Substitution and Shaping

Figure 43:
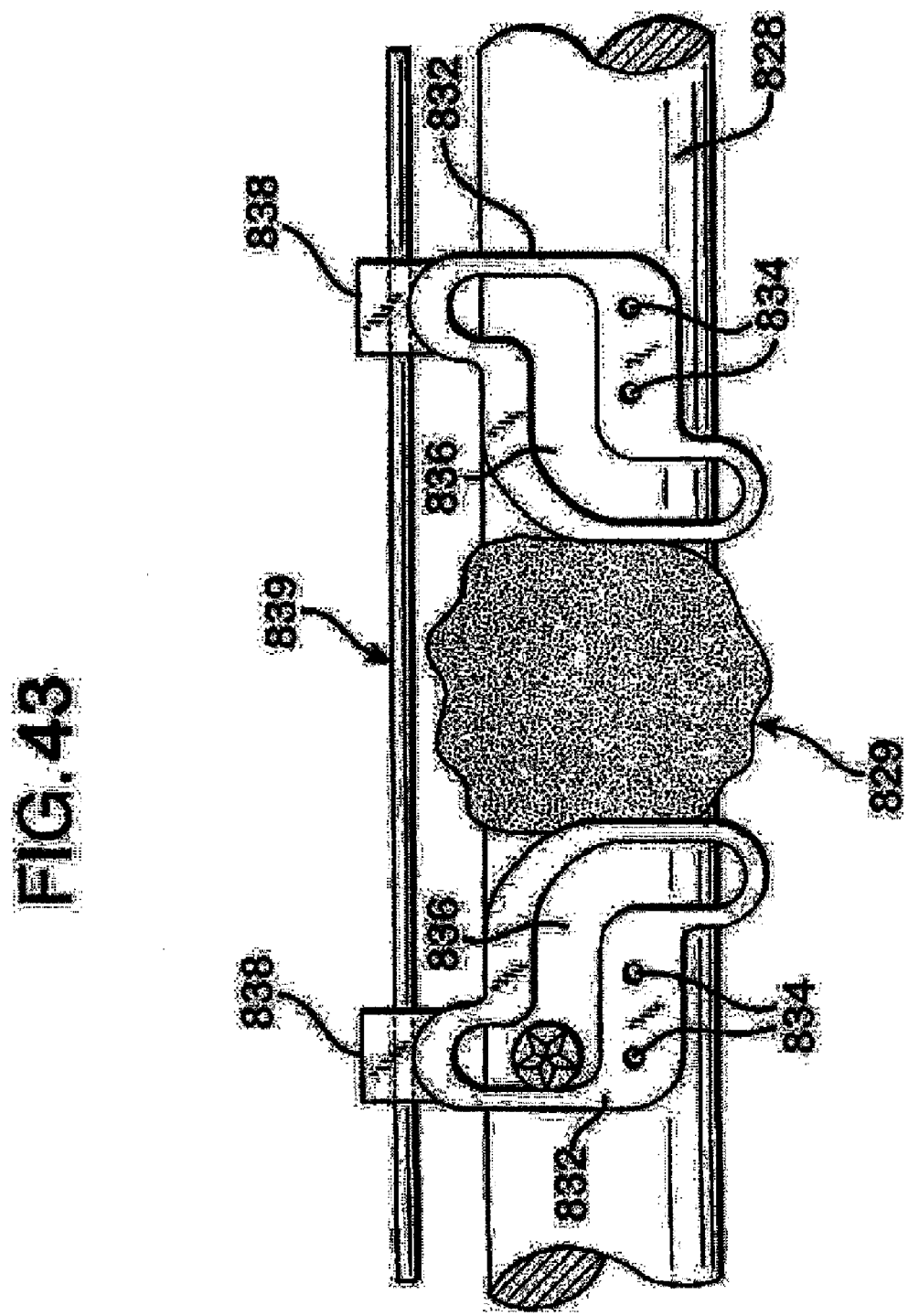
FIG. 43 is a perspective view of another embodiment of the pattern apparatus of the present invention for cutting a bone.

Referring now to FIG. 43, another embodiment of the pattern apparatus of the present invention for cutting bone is shown. This embodiment of the invention includes pattern plates 832 having cutting paths 836 described therein. The pattern plates 832 may be positioned on a bone 828 having a tumor or other pathology 829 associated therewith. The pattern plates 832 may be interconnected by crossbars 838 with opposing pattern plates (not shown) positioned on the opposite side of the bone 828. Further, each set of pattern plates 832 could be interconnected by means of positioning rod 839 extending between the crossbars 838 to maintain the relative location and orientation between the sets of pattern plates 832. The pattern plates can be positioned along the bone in accordance with what is known in the art, disclosed herein or hereafter developed. After the pattern plates are properly positioned, they can be affixed to the bone 828 with fixation means extending through fixation apertures 834. After the pattern plates are properly located and affixed to the bone, cutting can commence by traversing a cutting means along the cutting paths 836 of the pattern plates 832. By this step, the tumor or other pathology 829 can be cut from the bone 828 and a bone graft or other surgical procedure can be implemented to repair and/or replace the bone that has been cut. The benefits of cutting a bone with the pattern plates of the present invention include providing smooth and even cuts to the bone to facilitate fixation of bone grafts or other means for repairing and/or replacing bone. Further, the same pattern plates can be used to cut another identical sized and shaped bone for grafting to the first bone to replace the cut away bone.

Alternate Positioning and Alignment Guide

Figure 44:
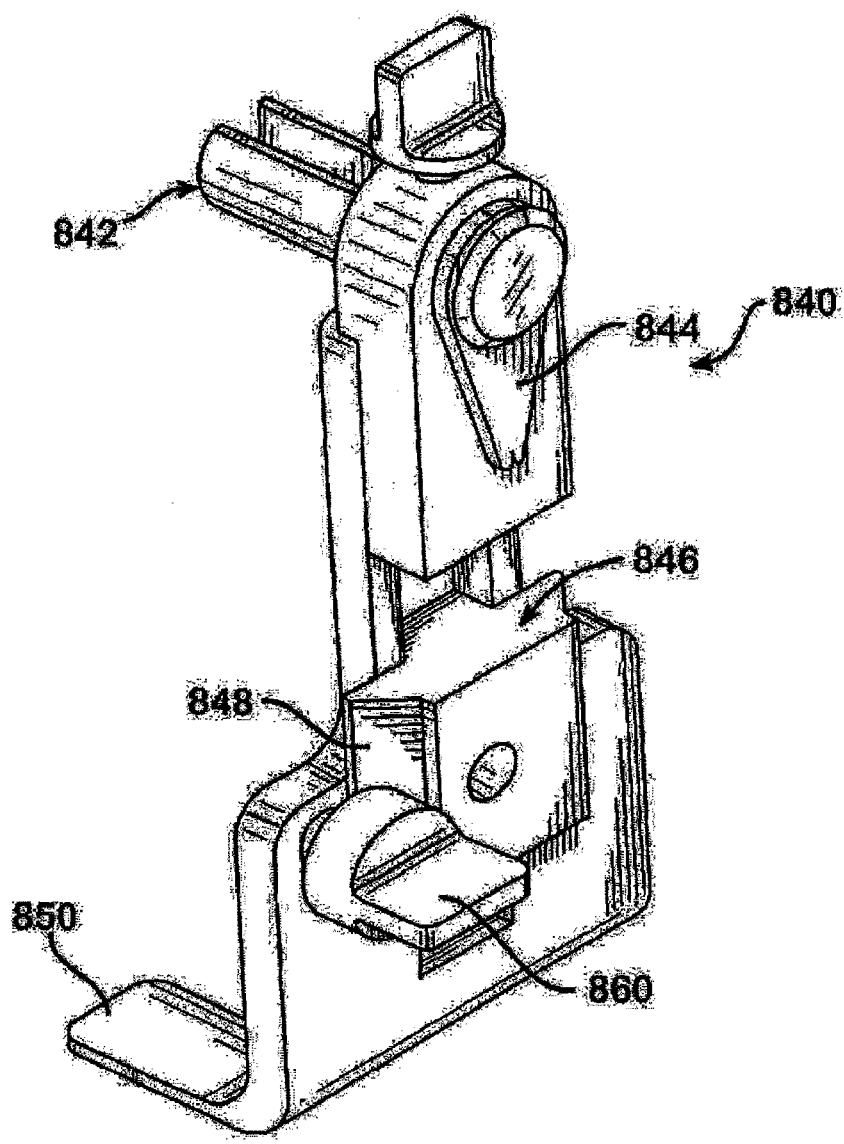
FIG. 44 is a perspective view of another embodiment of the alignment apparatus shown in FIG. 24.

An alternate positioning and alignment guide is generally indicated at 840 in FIG. 44. The positioning body 840 comprises a crossbar linkage 842 and an alignment indicator 844 at an upper end thereof for interconnecting with a crossbar to align pattern plates interconnected with such crossbar. The positioning body 840 also includes an alignment block 846 for interconnecting with an intramedullary rod in much the same manner as the IM rod guide block shown in FIG. 28. The alignment block 846 is vertically movable along the positioning body 840 and can be locked into a desired position by means of lock screw 860 which bears against a flange 848 of the alignment block 846. The positioning body 840 further includes skids 850 for contacting the posterior surface of the distal femoral condyles for referencing same.

Unicondylar and/or Single Pattern Plate Support

Figure 45:
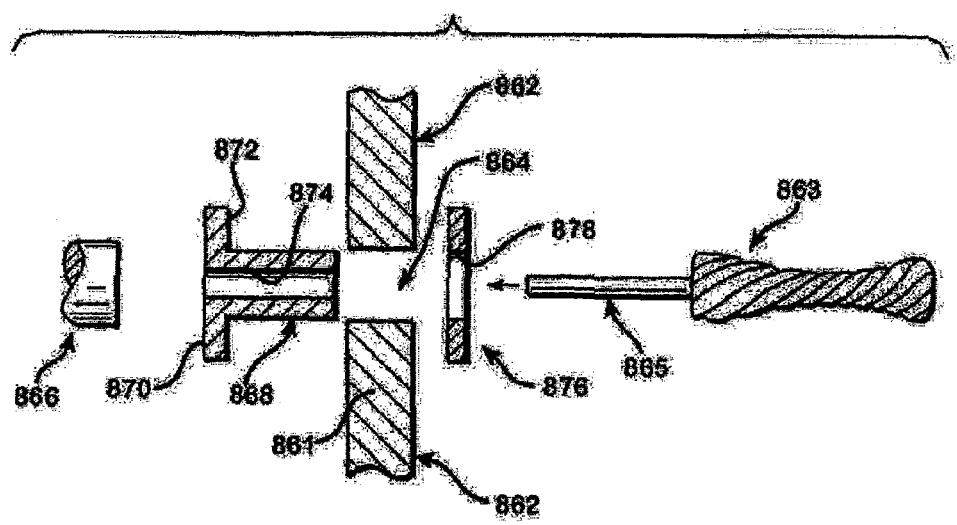
FIG. 45 is a partially exploded side plan view of another embodiment of the pattern apparatus of the present invention for cutting a bone.
Figure 46:
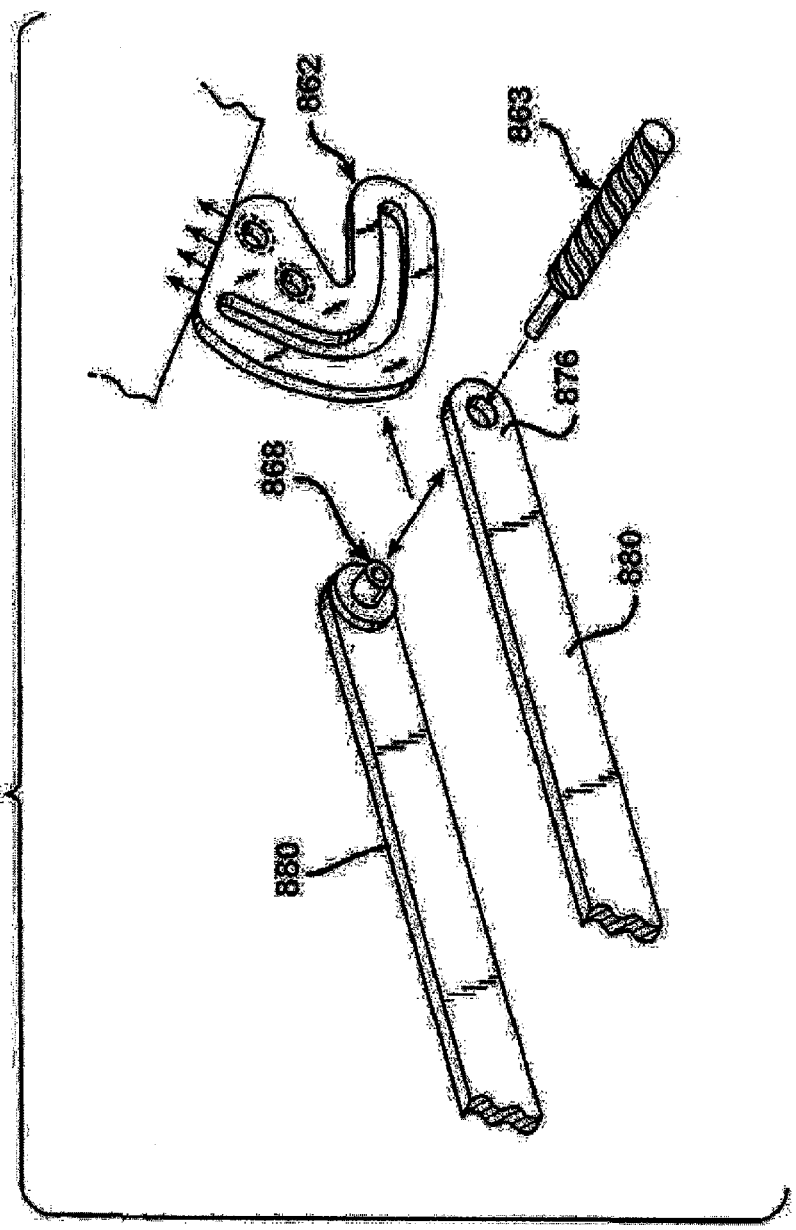
FIG. 46 is a partially exploded perspective view of the interconnection of a handle with milling bit for use in connection with pattern plate shown in FIG. 45.

As shown in FIGS. 45 and 46, one pattern plate of the present invention can be used by itself to guide a cutting means along a cutting path to cut a bone. Such an application is particularly useful for unicondylar resecting of a femur. Use of a single pattern plate 862 is facilitated by bushing 868 having an outer flange 870 with a bearing surface 872 and an internal bore 874 sized to receive a spindle 865 of a cutting tool therein. The bushing 868 is sized to fit into the cutting path 864 of the pattern plate 862, the bearing surface 872 of the flange 870 contacting the side of the pattern plate 862. Washer 876 includes a central bore 878 sized to receive the far end of the bushing 868 extending past the pattern plate 862, the washer bearing against the side of the pattern plate 862 opposite the side that the bearing surface 872 of the flange 870 of the bushing 868 bears against. Thus, the washer and the bushing co-act to form a stable link with a pattern plate. As shown in FIG. 46, this link can be fortified by means of bearing arms 880 interconnected with the bushing and the washer, or formed integrally as part thereof, which by pressure means are forced together to retain the bushing within the cutting path of the pattern plate. After the bushing is captured within the cutting path, the spindle of the cutting means can be inserted through the bushing and interconnected with means 866 for driving the cutting means. Alternatively, it should be pointed out that when using a single pattern plate to cut a bone, it may be desirable to support the cutting means at the pattern plate and also at the other end thereof. One could effect such desired support at the other end of the cutting means by a brace or other linkage interconnecting the other end of the cutting means with a secondary support or anchor means positioned on the opposite side of the bone or at another location.

Revisions

Conventional revisions require removal of the old implant and the referencing of uncertain landmarks. Revisions, by means of the present invention, allow for reference of the implant while it is still on the bone. One can obtain varus/valgus referencing, distal resection depth, posterior resection depth and rotational alignment by referencing the geometry of the implant with the alignment guide. An extramedullary alignment rod can be used to facilitate flexion/extension alignment. The fixation screws can then be advanced to touch the bone and mark their location by passing standard drill bits or pins through the cannulations in the fixation screws and into the bone. Then, the pattern and guide device are removed, the old implant removed, and the pattern device repositioned by means of the marked location of the fixation screws and then fixed into place. Accordingly, the cuts for the new implant, and thus the new implant itself, are located and orientated based off of the old implant. This results in increased precision and awareness of the final implant location and orientation as well as potential intraoperative time savings.

The particular example of the present invention discussed herein relates to a prosthetic implant for attachment to a femur in the context of total knee arthroplasty, i.e., a femoral implant. However, it should be pointed out that the principles described herein may be applied to any other applications where foreign or indigenous material is affixed to any other anatomic feature.

Figure 48:
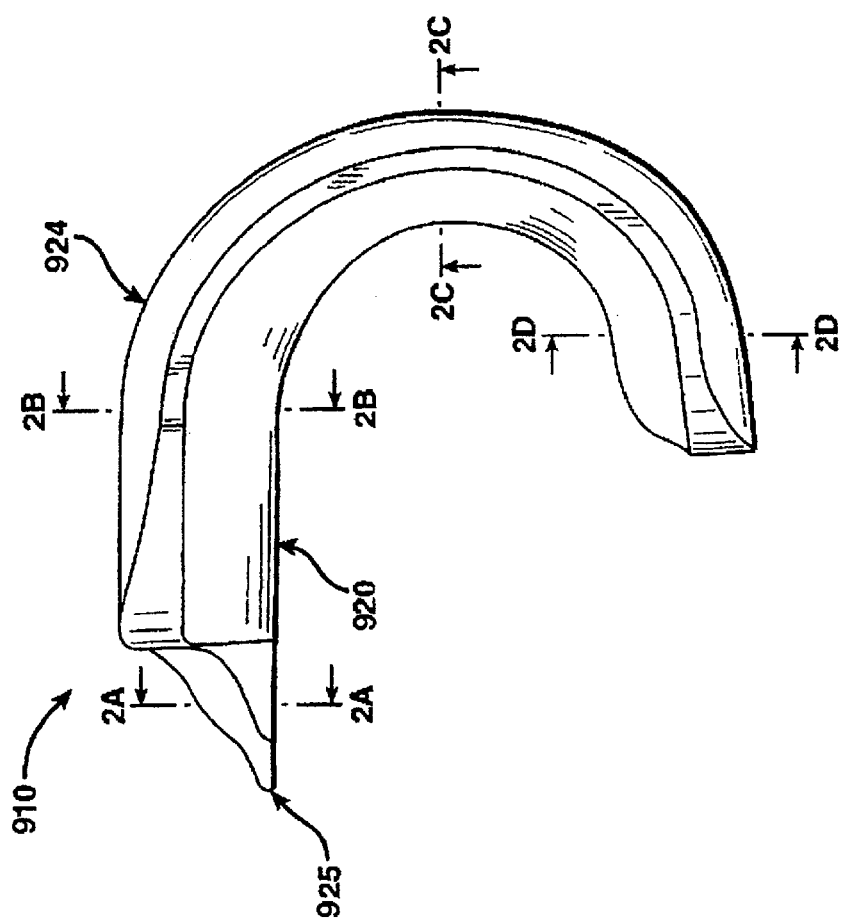
FIG. 48 is a side plan view of the femoral implant shown in FIG. 38, FIGS. 48A, 48B, 48C and 48D being sectional views taken along lines A-A, B-B, C-C and D-D of FIG. 48, respectively.
Figure 48A:
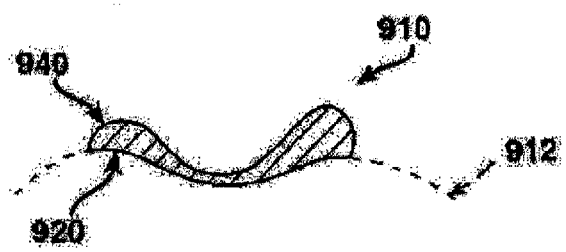
Figure 48B:
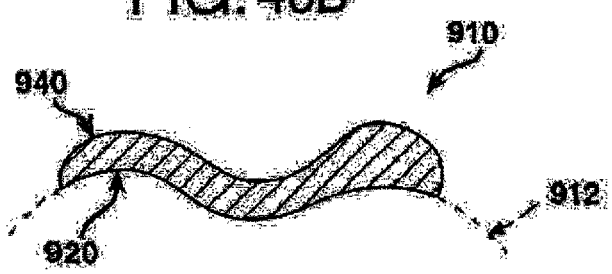
Figure 48C:
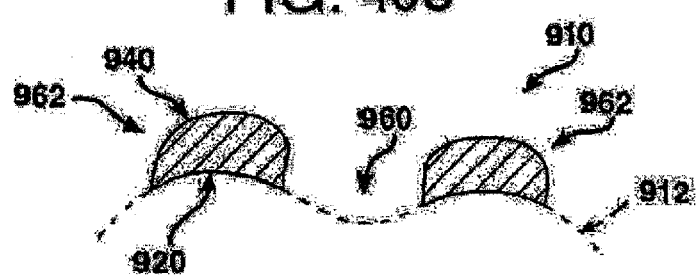
Figure 48D:
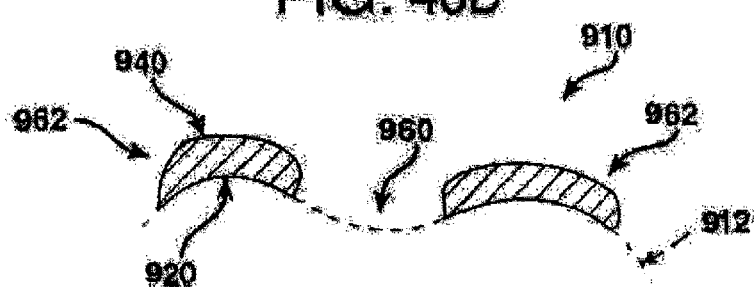

As shown generally in FIGS. 38 and 48, the implant apparatus of the present invention, generally indicated at 910, comprises curvilinear interior fixation surface 920 as well as curvilinear exterior bearing surface 940. Importantly, the implant of the present invention includes curvilinear surfaces extending from an anterior to a posterior area of the femur and/or implant, as is conventionally known, as well as curvilinear surfaces extending from a medial to a lateral area of the femur and/or implant to approximate the shape of natural femur. In other words, the fixation path (i.e., corresponding to the cutting path along which the milling bit rides to resect the femur; indicated by arrow A in FIG. 38) as well as the fixation profile (as one proceeds along the cutting profile orthogonally to the cutting path; indicated by arrow B in FIG. 38) are both predominantly curvilinear. As such, the cutting profile (arrow B) of the interior fixation surface 920 could include a curved or flat area 922 and another curved or flat area 924 therebetween. Preferably, the outer areas 922 are flat or relatively flat and the inner area 924 is curved to approximate the shape of a natural distal femur 912. It should be pointed out that the outer areas 922 could be curved, and the inner area 924 could also be curved, but embodying differing radii of curvature. Additionally, it should be pointed out that the geometry of the internal fixation surface 920 of the implant 910 could be varied as desired. As such, any combination of flat surfaces and curvilinear surfaces could be used. As shown in FIG. 48, and in more detail in FIGS. 48A, 48B, 48C and 48D, the cross-sectional thickness and mediolateral width of the implant of the present invention could vary along the implant 910. This variance results from merging a cutting tool to cut a bone, i.e., the implant 910 closely resembles in size and shape the material removed from the bone. Accordingly, the cut starts as a point 925 and grows in depth and width.

The curvilinear bone surfaces necessary for proper fixation of such an implant 910 may be generated through the use of the curvilinear milling bit or form cutter and the curvilinear cutting path means discussed in the previous related applications set forth herein, the entire disclosures of which are expressly incorporated herein by reference. Basically, the milling bit has a profile resulting in form cutter configuration which is concentric about its longitudinal axis to effect a curvilinear cutting profile for receiving the implant of the present invention. One embodiment of such a form cutter is shown in FIGS. 35 and 49. While it is possible to use multiple form cutters with differing geometries and therefore an implant 910 with an internal geometry that varies along the cutting path from the anterior to the posterior of a femur, for the sake of intraoperative time savings, a single anatomically optimal form cutter is preferable.

The form cutter shown in FIGS. 35 and 49 comprises a cutting guide 950 having cutting paths 952 interconnected by member 954. A milling bit 960 having cylindrical milling areas 962 at the ends, and a curved milling area 964 at the center could be used. Of course, the milling areas carry cutting teeth. Spindles 961 interconnected at each end of the milling bit 960 could engage and ride the cutting path 952 of the cutting guide 950. The milling bit 960 is then guided along the cutting path 952 by means of a handle. Importantly, the shape of the milling bit 960 could be varied as desired to create a resection having a desired cutting path as well as a desired cutting profile.

The mediolateral cross-sectional internal geometry of such an implant 910, and therefore the necessary resected bony surfaces of the femur, are consistent about the cutting path in a single form cutter system. It should be noted that the implant 910 may possess a notch 970 between members 972 (posterior femoral implant condyles) in the areas approximately between the distal and posterior femoral condylar areas to accommodate the posterior cruciate ligament, as well as for other reasons. Because of the notch 970 between the posterior femoral condyles, the form cutter may not cut any material in the notch 970.

Additionally, it may be advantageous to utilize a secondary form cutter as shown in FIG. 47 for use in creating a slot or slots in or near the distal area of the femur before or after it has been resected. Such a secondary cutter 790 would include engagement means 792 for engagement with driving means, and a shaft 794 carrying one or more cutters 796 for cutting slots into the femur through one or more of the resected surfaces thereof.

Figure 50:
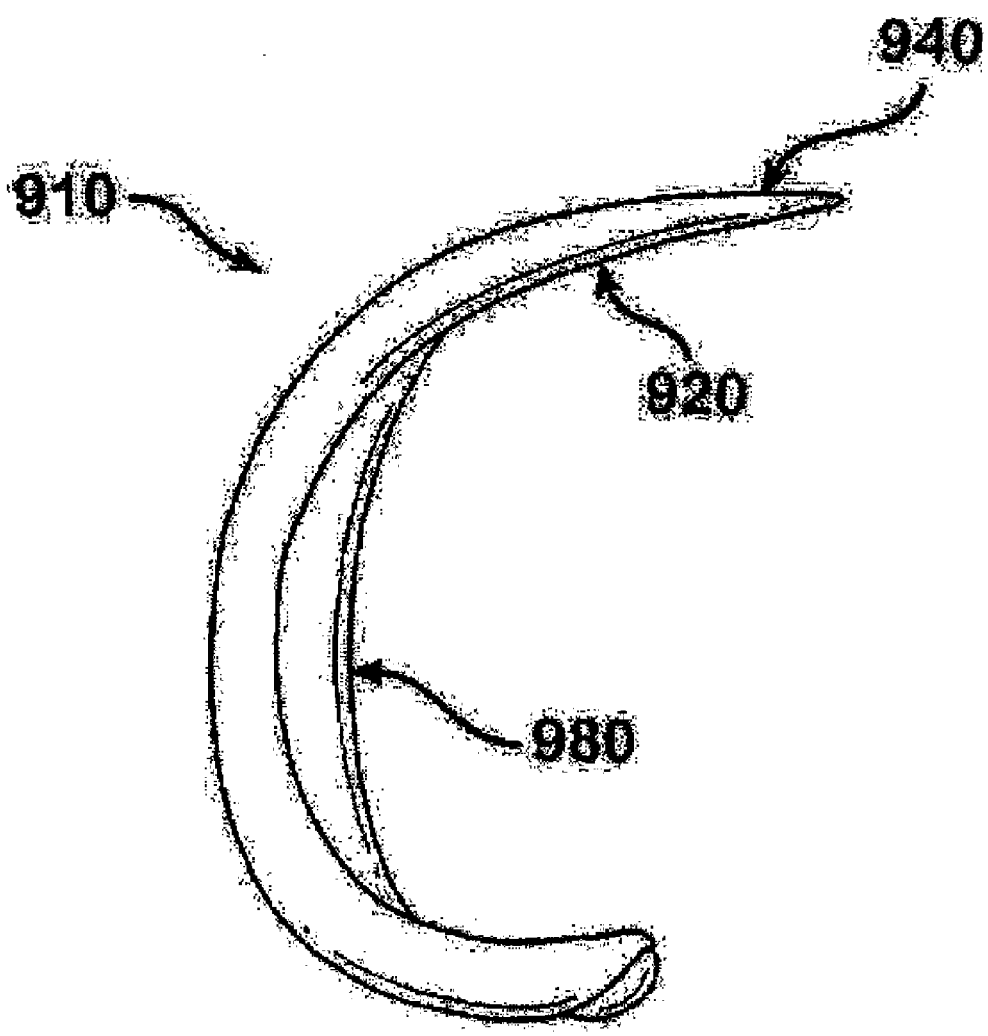
FIG. 50 is a side plan view of another embodiment of the femoral implant shown in FIG. 38.

Through the inclusion of an additional or adjunct cutting path in the pattern means, it would be advantageous to utilize the form cutter to create the aforementioned slots in the distal femur to accommodate the fixation fins which may be molded as an integral part of the interior surface of the implant 910. An implant with fixation fins is shown in FIG. 50. The fins 980 would provide mediolateral fixation stability in addition to that provided by the trochlear groove geometry of the implant 910. Further, the fins also provide for additional surface area for bony contact and ingrowth to increase implant fixation both in cemented and cementless total knee arthroplasty.

Figure 33B:
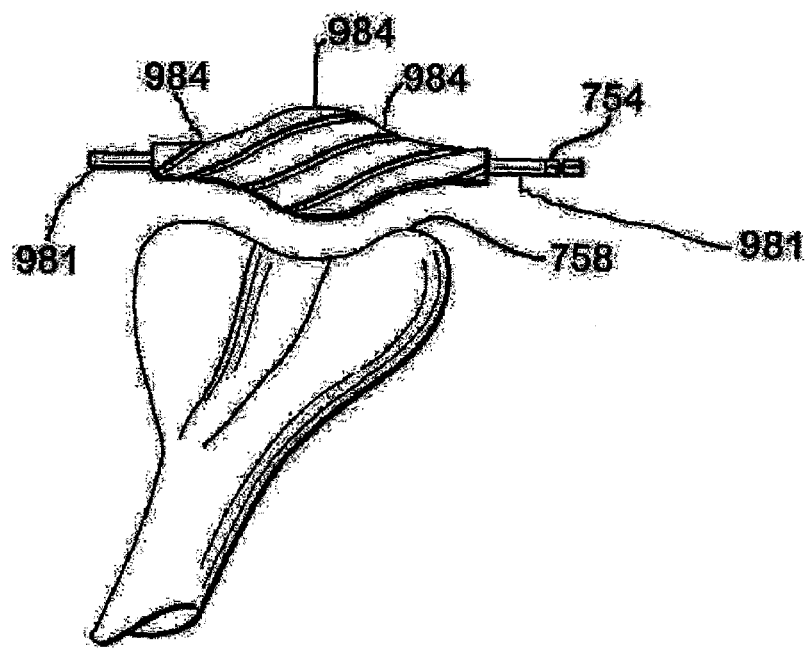

FIG. 33b shows another embodiment of a milling bit, generally indicated at 754 for creating a curvilinear cutting path and curvilinear cutting profile in femur 756. In this embodiment, the transition from a first cutting area 984 to a second cutting area 986 is continuous and smooth. This milling bit 754 also includes spindles 981 at the ends thereof for engagement with pattern means to guide the milling bit along a cutting path.

There are numerous advantages to the femoral component herein described. Foremost, it will allow for the thinnest implant cross-section possible (perhaps 3 mm to 6 mm in nominal thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint.

In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. The implant could have a relatively consistent cross-sectional thickness throughout the implant, or it could be varied as desired.

The curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e., when a cast is placed on a person's arm the muscles in that arm gradually weaken for lack of use.

Further, the curvilinear implant of the present invention could allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant would not only allow for the superior surface properties of ceramic, but also avoid the excessively thick cross-sections currently required for the use of the material.

The curvilinear implant of the present invention could result in a less expensive femoral implant because of the reduced amount of material needed for the implant, as well as an improved, more natural, and even stronger knee replacement. It may desirable to vary the cross-section of the implant to assist in seating the implant, to increase the joint kinematics and to increase the strength and fit of the implant. The implant of the present invention could be fabricated of metal, plastic, or ceramic or any other material or combination thereof. Further, the thickness of the implants and the material required to fabricate the implant could be reduced as the implants are adapted to increasingly curvilinear surfaces. Also, it should be pointed out that such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Importantly, by using a milling bit having a curved profile, one can cut a femur to resemble the natural shape of the femur, i.e., the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof, as shown in FIGS. 35 and 49, or alternatively, could have one or more bulges discretely formed along the length thereof.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. A method for a knee arthroplasty procedure comprising:

positioning at least one generally planar cutting guide surface that is adapted to interface with and guide a saw blade such that at least a portion of the at least one guide surface is positioned along one of a medial side or a lateral side and proximate an end of a long bone of a knee joint, the at least one guide surface also being positioned generally transverse to a long axis of the long bone with the portion of the at least one guide surface having a longer dimension generally along the at least one of the medial side or the lateral side and a shorter dimension generally transverse to the longer dimension;

using a cutting tool having a saw blade with a cutting edge at a distal end of a long axis of the saw blade to create at least a portion of one resected surface on the end of the long bone by guiding the saw blade with at least the portion of the at least one guide surface and moving the saw blade in a direction along the long axis of the saw blade, the direction of the long axis of the saw blade being generally parallel to the shorter dimension; and implanting a knee arthroplasty implant on the at least one resected surface.

2. The method of claim 1 wherein the long bone is the femur and the step of positioning the at least one planar guide surface is performed proximate a distal end of the femur.

3. The method of claim 2 wherein the step of using the cutting tool creates at least two resected surfaces, including a distal surface on the femur and an anterior surface on the femur.

4. The method of claim 1 wherein the long bone is a tibia and the step of positioning the at least one planar cutting guide surface is performed proximate a proximal end of the tibia.

5. A method for a knee implant procedure comprising:

positioning at least one generally planar cutting guide surface that is adapted to interface with and guide a saw blade such that at least a portion of the at least one guide surface is positioned along one of a medial side or a lateral side and proximate an end of a long bone of a knee joint, the at least one guide surface also being positioned generally transverse to a long axis of the long bone with the portion of the at least one guide surface having a longer dimension generally along the at least one of the medial side or the lateral side and a shorter dimension generally transverse to the longer dimension;

using a cutting tool having a saw blade with a cutting edge at a distal end of a long axis of the saw blade to create at least a portion of one resected surface proximate the end of the long bone by guiding the saw blade with at least the portion of the at least one guide surface and moving the saw blade in a direction along the long axis of the saw blade, the direction of the long axis of the saw blade being generally parallel to the shorter dimension; and implanting a knee implant on the at least one resected surface, wherein the at least one guide surface includes at least two portions, the portion located along the at least one of the medial side or the lateral side and an other portion located along an anterior side and proximate the end of the long bone and having a longer dimension generally along the at least anterior side and a shorter dimension generally transverse to the longer dimension, wherein the step of positioning the at least one guide surface is performed such the other portion extends to less than about one-half of a width of the anterior side.

6. A method for a knee implant procedure comprising:

operably positioning at least one generally planar cutting guide surface that is adapted to interface with and guide a saw blade such that at least a portion of the at least one guide surface is operably positioned along one of a medial side or a lateral side and proximate an end of a long bone of a knee joint, the at least one guide surface also being operably positioned generally transverse to a long axis of the long bone with the portion of the at least one guide surface having a longer dimension generally along the at least one of the medial side or the lateral side and a shorter dimension generally transverse to the longer dimension;

using an alignment mechanism operably coupled to the at least one planar cutting guide surface to align the at least one guide surface relative to the long bone in at least three degrees of freedom, at least one of the degrees of freedom being rotational; and locking the alignment mechanism to position the at least one guide surface in a desired location and orientation;

using a cutting tool having a saw blade with a cutting edge at a distal end of a long axis of the saw blade to create at least a portion of one resected surface proximate the end of the long bone by guiding the saw blade with at least the portion of the at least one guide surface and moving the saw blade in a direction along the long axis of the saw blade, the direction of the long axis of the saw blade being generally parallel to the shorter dimension; and implanting a knee implant on the at least one resected surface.

7. The method of claim 6 wherein the step of using the alignment mechanism is performed by moving the at least one guide surface through at least a portion of an infinitely adjustable range of motion for the at least one of the at least three degrees of freedom.

8. The method of claim 1 wherein the step of using the cutting tool is performed with a powered saw selected from the set consisting of an oscillating saw or a reciprocating saw.

9. A method for a knee arthroplasty procedure comprising:

providing a cutting guide having a slot adapted to receive and guide a cutting tool, the cutting tool having a saw blade with at least one cutting edge at a distal end of a long axis of the saw blade;

positioning the cutting guide in a position proximate an end of one of a femur or a tibia with at least a portion of the slot facing the end of the one of the femur or the tibia from one of a medial aspect or a lateral aspect;

extending the saw blade though the slot;

cutting the end of the one of the femur or the tibia by moving the cutting tool in a direction along the long axis, the direction of the long axis being at least one of a medial to lateral direction or a lateral to medial direction to create at least a portion of at least one resected surface; and implanting a knee arthroplasty implant on the at least one resected surface.

10. A method for a knee arthroplasty procedure comprising:

providing a cutting guide having a slot adapted to receive and guide a cutting tool, the cutting tool having a saw blade with at least one cutting edge at a distal end of a long axis of the saw blade;

positioning the cutting guide in a position proximate an end of one of a femur or a tibia with at least a portion of the slot facing the end of the one of the femur or the tibia from one of a medial aspect or a lateral aspect by:

using an alignment guide operably coupled to the cutting guide to align the slot relative to the one of the femur or the tibia in at least three degrees of freedom, at least one of the degrees of freedom being rotational; and locking the alignment guide to position the cutting guide in a desired location and orientation;

extending the saw blade though the slot;

cutting the end of the one of the femur or the tibia by moving the cutting tool along the long axis in at least one of a medial to lateral direction or a lateral to medial direction to create at least one resected surface; and implanting a knee arthroplasty implant on the at least one resected surface.

11. The method of claim 10 wherein the step of using the alignment guide moves the cutting guide though an infinitely adjustable range of motion.

12. The method of claim 9 wherein the cutting tool is a powered saw and the step of cutting is performed with the powered saw selected from the set consisting of an oscillating saw or a reciprocating saw.

13. A method for a knee implant procedure comprising:
providing implants and instrumentation for the knee implant procedure, the implants and instrumentation including at least:
a femoral implant;
a tibial implant;
a femoral intramedullary rod;
a femoral alignment guide extending at an angle to the femoral intramedullary rod;
a femoral cut guide mountable to the femoral alignment guide;
a tibial extramedullary alignment guide; and
a tibial cut guide;
resecting a distal end of a femur of a knee including at least:
inserting the femoral intramedullary rod into an intramedullary canal of the femur;
positioning the femoral alignment guide so that a surface on the femoral alignment guide contacts a distal femoral condyle;
operably connecting the femoral cut guide to the femoral alignment guide and positioning the femoral cut guide to extend toward and generally along at least one of a medial side or a lateral side of the knee; and
guiding a cutting tool having a saw blade with a cutting edge at a distal end of a long axis of the saw blade by using the femoral cut guide to create at least one resected surface on the distal end of the femur by guiding the long axis of the saw blade from the at least one of the medial side or the lateral side of the knee;
resecting a proximal end of a tibia of the knee including at least:
positioning the tibial extramedullary alignment guide;
operably connecting the tibial cut guide to the tibial extramedullary alignment guide and positioning the tibial cut guide generally adjacent at least a portion of an anterior side of the tibia and at least one of the medial side or the lateral side of the knee; and
guiding a cutting tool having a saw blade with a cutting edge at a distal end of a long axis of the saw blade by using the tibial cut guide to create at least one resected surface on the proximal end of the tibia by guiding the long axis of the saw blade from at least one of the medial side or the lateral side of the knee; and
implanting the implants by:
positioning the femoral implant with at least one fixation surface of the femoral implant generally adjacent the at least one resected surface of the femur; and
positioning the tibial implant with at least one fixation surface of the tibial implant generally adjacent to the at least one resected surface of the tibia.

14. The method of claim 13 wherein the step of positioning the femoral cut guide comprises:
using the femoral alignment guide operably to align the femoral cut guide relative to the femur in at least three degrees of freedom, at least one of the degrees of freedom being rotational; and
locking the femoral alignment guide to position the femoral cut guide in a desired location and orientation.

15. The method of claim 14 wherein the step of using the femoral alignment guide moves the femoral cut guide through an infinitely adjustable range of motion.

16. The method of claim 13 wherein the step of positioning the femoral cut guide positions the femoral cut guide to extend toward and generally along one of the medial side or the lateral side of the knee.

17. The method of claim 13 wherein the step of positioning the tibial cut guide comprises:
using the tibial alignment guide operably to align the tibial cut guide relative to the tibia in at least three degrees of freedom, at least one of the degrees of freedom being rotational; and
locking the tibial alignment guide to position the tibial cut guide in a desired location and orientation.

18. The method of claim 17 wherein the step of using the tibial alignment guide moves the tibial cut guide through an infinitely adjustable range of motion.

19. The method of claim 13 wherein the step of positioning the tibial cut guide positions the tibial cut guide to extend toward and generally along one of the medial side or the lateral side of the knee.

20. The method of claim 13 wherein the cutting tool for the step of resecting the distal end of the femur is the same as the cutting tool for the step of resecting the proximal end of the tibia and is a powered saw and each step is performed with the powered saw selected from the set consisting of an oscillating saw or a reciprocating saw.

21. A method for providing instrumentation, implants and information for a knee arthroplasty procedure comprising:
providing a knee arthroplasty implant and a cutting guide having at least one generally planar cutting guide surface that is adapted to interface with and guide a saw blade such that at least a portion of the at least one guide surface is adapted to be positioned along one of a medial side or a lateral side and proximate an end of a long bone of a knee joint, the at least one guide surface also being adapted to be positioned generally transverse to a long axis of the long bone with the portion of the at least one guide surface having a longer dimension generally along the at least one of the medial side or the lateral side and a shorter dimension generally transverse to the longer dimension; and
providing a surgeon with information on a method to perform the knee arthroplasty procedure using the cutting guide and the knee arthroplasty implant, the method including:
positioning the at least one generally planar cutting guide surface that is adapted to interface with and guide a saw blade such that at least a portion of the at least one guide surface is positioned along one of the medial side or the lateral side and proximate an end of a long bone of a knee joint, the at least one guide surface also being positioned generally transverse to a long axis of the long bone with the portion of the at least one guide surface having a longer dimension generally along the at least one of the medial side or the lateral side and a shorter dimension generally transverse to the longer dimension;
using a cutting tool having a saw blade with a cutting edge at a distal end of a long axis of the saw blade to create at least a portion of at least one resected surface on the end of the long bone by guiding the saw blade with at least the portion of the at least one guide surface and moving the saw blade in a direction along the long axis of the saw blade, the direction of the long axis of the saw blade being generally parallel to the shorter dimension; and implanting the knee arthroplasty implant on the at least one resected surface.

22. A method for providing instrumentation, implants and information for a knee arthroplasty procedure comprising:

providing a knee arthroplasty implant and a cutting guide having at least one generally planar cutting guide surface that is adapted to interface with and guide a saw blade such that at least a portion of the at least one guide surface is adapted to be positioned along one of a medial side or a lateral side and proximate an end of a long bone of a knee joint, the at least one guide surface also being adapted to be positioned generally transverse to a long axis of the long bone with the portion of the at least one guide surface having a longer dimension generally along the at least one of the medial side or the lateral side and a shorter dimension generally transverse to the longer dimension; and providing a surgeon with information on a method to perform the knee arthroplasty procedure using the cutting guide and the knee arthroplasty implant, the method including:

positioning the at least one generally planar cutting guide surface that is adapted to interface with and guide a saw blade such that at least a portion of the at least one guide surface is positioned along one of the medial side or the lateral side and proximate an end of a long bone of a knee joint, the at least one guide surface also being positioned generally transverse to a long axis of the long bone with the portion of the at least one guide surface having a longer dimension generally along the at least one of the medial side or the lateral side and a shorter dimension generally transverse to the longer dimension;

using a cutting tool having a saw blade with a cutting edge at a distal end of a long axis of the saw blade to create at least a portion of one resected surface proximate the end of the long bone by guiding the saw blade with at least the portion of the at least one guide surface moving the saw blade in a direction along the long axis of the saw blade, the direction of the long axis of the saw blade being generally parallel to the shorter dimension; and implanting the knee implant on the at least one resected surface, wherein the at least one guide surface includes at least two portions, the portion located along the at least one of the medial side or the lateral side and an other portion located along an anterior side and proximate the end of the long bone and having a longer dimension generally along the at least anterior side and a shorter dimension generally transverse to the longer dimension, wherein the step of positioning the at least one guide surface is performed such the other portion extends to less than about one-half of a width of the anterior side.

23. A method for providing instrumentation, implants and information for a knee arthroplasty procedure comprising:

providing a cutting guide having at least one generally planar cutting guide surface, an alignment mechanism operably coupled to the at least one planar cutting guide surface and a knee arthroplasty implant; and providing a surgeon with information on a method to perform the knee arthroplasty procedure using the cutting guide, the alignment mechanism and the knee arthroplasty implant, the method including:

operably positioning the at least one generally planar cutting guide surface that is adapted to interface with and guide a saw blade such that at least a portion of the at least one guide surface is operably positioned along one of a medial side or a lateral side and proximate an end of a long bone of a knee joint, the at least one guide surface also being operably positioned generally transverse to a long axis of the long bone with the portion of the at least one guide surface having a longer dimension generally along the at least one of the medial side or the lateral side and a shorter dimension generally transverse to the longer dimension;

using the alignment mechanism operably coupled to the at least one planar cutting guide surface to align the at least one guide surface relative to the long bone in at least thee degrees of freedom, at least one of the degrees of freedom being rotational; and locking the alignment mechanism to position the at least one guide surface in a desired location and orientation;

using a cutting tool having a saw blade with a cutting edge at a distal end of a long axis of the saw blade to create at least a portion of one resected surface proximate the end of the long bone by guiding the saw blade with at least the portion of the at least one guide surface and moving the saw blade in a direction along the long axis of the saw blade, the direction of the long axis of the saw blade being generally parallel to the shorter dimension; and implanting the knee implant on the at least one resected surface.

24. A method for providing instrumentation, implants and information for a knee arthroplasty procedure comprising:

providing a knee arthroplasty implant and a cutting guide having a slot adapted to receive and guide a cutting tool, the cutting tool having a saw blade with at least one cutting edge at a distal end of a long axis of the saw blade;

providing a surgeon with information on a method to perform the knee arthroplasty procedure using the cutting guide, the cutting tool and the knee arthroplasty implant, the method including:

positioning the cutting guide in a position proximate an end of one of a femur or a tibia with at least a portion of the slot facing the end of the one of the femur or the tibia from one of a medial aspect or a lateral aspect;

extending the saw blade through the slot;

cutting the end of the one of the femur or the tibia by moving the cutting tool in a direction along the long axis, the direction of the long axis being at least one of a medial to lateral direction or a lateral to medial direction to create at least a portion of at least one resected surface; and implanting the knee arthroplasty implant on the at least one resected surface.

25. A method for providing instrumentation, implants and information for a knee arthroplasty procedure comprising:

providing a knee implant, a cutting guide having a slot adapted to receive and guide a cutting tool, the cutting tool having a saw blade with at least one cutting edge at a distal end of a long axis of the saw blade and an alignment guide operably coupled to the cutting guide;

providing a surgeon with information on a method to perform the knee arthroplasty procedure using the cutting guide, the cutting tool and the knee arthroplasty implant, the method including:
  positioning the cutting guide in a position proximate an end of one of a femur or a tibia with at least a portion of the slot facing the end of the one of the femur or the tibia from one of a medial aspect or a lateral aspect by:
    using the alignment guide operably coupled to the cutting guide to align the slot relative to the one of the femur or the tibia in at least three degrees of freedom, at least one of the degrees of freedom being rotational; and
    locking the alignment guide to position the cutting guide in a desired location and orientation;
  extending the saw blade though the slot;
  cutting the end of the one of the femur or the tibia by moving the cutting tool along the long axis in at least one of a medial to lateral direction or a lateral to medial direction to create at least one resected surface; and
  implanting the knee arthroplasty implant on the at least one resected surface.

26. A method for providing implants, instrumentation and information for a knee implant procedure comprising:
  providing implants and instrumentation for the knee implant procedure, the implants and instrumentation including at least:
    a femoral implant;
    a tibial implant;
    a femoral intramedullary rod;
    a femoral alignment guide extending at an angle to the femoral intramedullary rod;
    a femoral cut guide mountable to the femoral alignment guide;
    a tibial extramedullary alignment guide; and
    a tibial cut guide;
  providing a surgeon with information for a method for performing the knee implant procedure comprising:
  resecting a distal end of a femur of a knee including at least:
    inserting the femoral intramedullary rod into an intramedullary canal of the femur;
    positioning the femoral alignment guide so that a surface on the femoral alignment guide contacts a distal femoral condyle;
    operably connecting the femoral cut guide to the femoral alignment guide and positioning the femoral cut guide to extend toward and generally along at least one of a medial side or a lateral side of the knee; and
    guiding a cutting tool having a saw blade with a cutting edge at a distal end of a long axis of the saw blade by using the femoral cut guide to create at least one resected surface on the distal end of the femur by guiding the long axis of the saw blade from the at least one of the medial side or the lateral side of the knee;
  resecting a proximal end of a tibia of the knee including at least:
    positioning the tibial extramedullary alignment guide;
    operably connecting the tibial cut guide to the tibial extramedullary alignment guide and positioning the tibial cut guide generally adjacent at least a portion of an anterior side of the tibia and at least one of the medial side or the lateral side of the knee; and
    guiding a cutting tool having a saw blade with a cutting edge at a distal end of a long axis of the saw blade by using the tibial cut guide to create at least one resected surface on the proximal end of the tibia by guiding the long axis of the saw blade from at least one of the medial side or the lateral side of the knee; and
  implanting the implants by:
    positioning the femoral implant with at least one fixation surface of the femoral implant generally adjacent the at least one resected surface of the femur; and
    positioning the tibial implant with at least one fixation surface of the tibial implant generally adjacent to the at least one resected surface of the tibia.

27. The method of claim 9 wherein positioning the cutting guide in a position proximate an end of one of a femur or a tibia includes fixing the cutting guide to the end of one of the femur or the tibia using a connection mechanism having a long axis that is oriented generally parallel to the resected surface and extends into one of the femur or the tibia from one of the medial aspect or the lateral aspect.

28. The method of claim 9 wherein positioning the cutting guide in a position proximate an end of one of a femur or a tibia further comprises:
  using an alignment mechanism operably coupled to the cutting guide to align the at least one guide surface relative to one of the femur or the tibia in at least three degrees of freedom, at least one of the degrees of freedom being rotational; and
  locking the alignment mechanism to position the cutting guide in a desired location and orientation.

29. The method of claim 28 wherein using the alignment mechanism is performed by moving the at least one guide surface though at least a portion of an infinitely adjustable range of motion for the at least one of the at least three degrees of freedom.

30. The method of claim 28 wherein using an alignment mechanism operably coupled to the cutting guide to align the at least one guide surface further includes adjusting the desired location and orientation of the cutting guide in each of varus-valgus, flexion-extension, internal-external rotation, anterior-posterior, medial-lateral, and proximal-distal degrees of freedom without invading an intra-medullary canal.

31. The method of claim 9 wherein cutting the end of the one of the femur or the tibia by moving the cutting tool in a direction along the long axis comprises plunging the saw blade through the slot to create the resected surface on both a medial portion or a lateral portion of the one of the femur or the tibia adjacent to the position of the cutting guide and a medial portion or a lateral portion of the one of the femur or the tibia across from and opposite to the position of the cutting guide.

32. The method of claim 9 wherein positioning the cutting guide is performed such that any portion of the slot facing the end of the one of the femur or the tibia from an anterior side extends to less than about one-half of a width of the at least one resected surface.

33. The method of claim 32 wherein cutting the end of the one of the femur or the tibia by moving the cutting tool in a direction along the long axis comprises plunging the saw blade through the slot to create the resected surface on both a medial portion or a lateral portion of the one of the femur or the tibia adjacent to the position of the cutting guide and a medial portion or a lateral portion of the one of the femur or the tibia across from and opposite to the position of the cutting guide.

34. The method of claim 9 wherein positioning the cutting guide comprises using a drill guide adapted to be manipulated in at least five of six degrees of freedom to create an aperture in the one of the femur or the tibia having a long axis substantially parallel to the resected surface, the long axis of the aperture dictating a location and orientation of the resected surface in one translational degree of freedom and one rotational degree of freedom when the cutting guide is connected in a predetermined location and orientation with respect to the long axis of the aperture.

35. The method of claim 13 wherein positioning the tibial cut guide locates the tibial cut guide generally medially and guiding the cutting tool having the saw blade with the cutting edge at the distal end of the long axis of the saw blade by using the tibial cut guide further includes cutting a lateral side of the tibia.

36. The method of claim 13 wherein positioning the tibial cut guide locates the tibial cut guide generally laterally and guiding the cutting tool having the saw blade with the cutting edge at the distal end of the long axis of the saw blade by using the tibial cut guide further includes cutting a medial side of the tibia.

37. The method of claim 13 wherein positioning the femoral cut guide locates the femoral cut guide generally medially and guiding the cutting tool having the saw blade with the cutting edge at the distal end of the long axis of the saw blade by using the femoral cut guide further includes cutting a lateral side of the femur.

38. The method of claim 13 wherein positioning the femoral cut guide locates the femoral cut guide generally laterally and guiding the cutting tool having the saw blade with the cutting edge at the distal end of the long axis of the saw blade by using the femoral cut guide further includes cutting a medial side of the femur.

39. The method of claim 16 wherein the femoral cut guide extends mediolaterally for a width less than one-half of a width of the femur and guiding the cutting tool having the saw blade with the cutting edge at the distal end of the long axis of the saw blade by using the femoral cut guide further includes cutting a contralateral compartment relative to the one of the medial side or the lateral side of the femur.

40. The method of claim 19 wherein the tibial cut guide extends mediolaterally for a width less than one-half of a width of the tibia and guiding the cutting tool having the saw blade with the cutting edge at the distal end of the long axis of the saw blade by using the tibial cut guide further includes cutting a contralateral compartment relative to the one of the medial side or the lateral side of the tibia.

41. The method of claim 24 wherein positioning the cutting guide in a position proximate an end of one of a femur or a tibia includes fixing the cutting guide to the end of one of the femur or the tibia using a connection mechanism having a long axis that is oriented generally parallel to the resected surface and extends into one of the femur or the tibia from one of the medial aspect or the lateral aspect.

42. The method of claim 24 wherein positioning the cutting guide in a position proximate an end of one of a femur or a tibia further comprises:
using an alignment mechanism operably coupled to the cutting guide to align the at least one guide surface relative to one of the femur or the tibia in at least three degrees of freedom, at least one of the degrees of freedom being rotational; and
locking the alignment mechanism to position the cutting guide in a desired location and orientation.

43. The method of claim 42 wherein using the alignment mechanism is performed by moving the at least one guide surface through at least a portion of an infinitely adjustable range of motion for the at least one of the at least three degrees of freedom.

44. The method of claim 42 wherein using an alignment mechanism operably coupled to the cutting guide to align the at least one guide surface further includes adjusting the desired location and orientation of the cutting guide in each of varus-valgus, flexion-extension, internal-external rotation, anterior-posterior, medial-lateral, and proximal-distal degrees of freedom without invading an intra-medullary canal.

45. The method of claim 24 wherein cutting the end of the one of the femur or the tibia by moving the cutting tool in a direction along the long axis comprises plunging the saw blade through the slot to create the resected surface on both a medial portion or a lateral portion of the one of the femur or the tibia adjacent to the position of the cutting guide and a medial portion or a lateral portion of the one of the femur or the tibia across from and opposite to the position of the cutting guide.

46. The method of claim 24 wherein positioning the cutting guide is performed such any portion of the slot facing the end of the one of the femur or the tibia from an anterior side extends to less than about one-half of a width of the at least one resected surface.

47. The method of claim 46 wherein cutting the end of the one of the femur or the tibia by moving the cutting tool in a direction along the long axis comprises plunging the saw blade through the slot to create the resected surface on both a medial portion or a lateral portion of the one of the femur or the tibia adjacent to the position of the cutting guide and a medial portion or a lateral portion of the one of the femur or the tibia across from and opposite to the position of the cutting guide.

48. The method of claim 24 wherein positioning the cutting guide comprises using a drill guide adapted to be manipulated in at least five of six degrees of freedom to create an aperture in the one of the femur or the tibia having a long axis substantially parallel to the resected surface, the long axis of the aperture dictating a location and orientation of the resected surface in one translational degree of freedom and one rotational degree of freedom when the cutting guide is connected in a predetermined location and orientation with respect to the long axis of the aperture.

49. The method of claim 26 wherein positioning the tibial cut guide locates the tibial cut guide generally medially and guiding the cutting tool having the saw blade with the cutting edge at the distal end of the long axis of the saw blade by using the tibial cut guide further includes cutting a lateral side of the tibia.

50. The method of claim 26 wherein positioning the tibial cut guide locates the tibial cut guide generally laterally and guiding the cutting tool having the saw blade with the cutting edge at the distal end of the long axis of the saw blade by using the tibial cut guide further includes cutting a medial side of the tibia.

51. The method of claim 26 wherein positioning the femoral cut guide locates the femoral cut guide generally medially and guiding the cutting tool having the saw blade with the cutting edge at the distal end of the long axis of the saw blade by using the femoral cut guide further includes cutting a lateral side of the femur.

52. The method of claim 26 wherein positioning the femoral cut guide locates the femoral cut guide generally laterally and guiding the cutting tool having the saw blade with the cutting edge at the distal end of the long axis of the saw blade by using the femoral cut guide further includes cutting a medial side of the femur.

53. The method of claim 26 wherein the step of positioning the femoral cut guide positions the femoral cut guide to extend toward and generally along one of the medial side or the lateral side of the knee and wherein the femoral cut guide extends mediolaterally for a width less than one-half of a width of the femur and guiding the cutting tool having the saw blade with the cutting edge at the distal end of the long axis of the saw blade by using the femoral cut guide further includes cutting a contralateral compartment relative to the one of the medial side or the lateral side of the femur.

54. The method of claim 26 wherein the step of positioning the tibial cut guide positions the tibial cut guide to extend toward and generally along one of the medial side or the lateral side of the knee and wherein the tibial cut guide extends mediolaterally for a width less than one-half of a width of the tibia and guiding the cutting tool having the saw blade with the cutting edge at the distal end of the long axis of the saw blade by using the tibial cut guide further includes cutting a contralateral compartment relative to the one of the medial side or the lateral side of the tibia.

* * * * *

UNITED STATES PATENT AND TRADEMARK OFFICE
CERTIFICATE OF CORRECTION

PATENT NO. : 7,344,541 B2  
APPLICATION NO. : 10/756817  
DATED : March 18, 2008  
INVENTOR(S) : Timothy G. Haines Page 1 of 1

It is certified that error appears in the above-identified patent and that said Letters Patent is hereby corrected as shown below:

Column 42, Claim 30, Line 39 "cuffing guide" should be --cutting guide--

Signed and Sealed this

First Day of July, 2008

JON W. DUDAS  
*Director of the United States Patent and Trademark Office*